United States Patent
Cnaan et al.

(10) Patent No.: US 11,997,455 B2
(45) Date of Patent: May 28, 2024

(54) SYSTEM AND METHOD FOR PROCESSING MULTI-DIRECTIONAL SIGNALS AND FEEDBACK TO A USER TO IMPROVE SLEEP

(71) Applicant: Koko Home, Inc., Palo Alto, CA (US)

(72) Inventors: Itay Cnaan, Palo Alto, CA (US); Eben James Bitonte, San Francisco, CA (US); Rosaria Mannino, Palo Alto, CA (US); Saurabh Gupta, Palo Alto, CA (US); Bradley Michael Eckert, San Francisco, CA (US)

(73) Assignee: Koko Home, Inc., Sunnyvale, CA (US)

( * ) Notice: Subject to any disclaimer, the term of this patent is extended or adjusted under 35 U.S.C. 154(b) by 243 days.

(21) Appl. No.: 17/401,737

(22) Filed: Aug. 13, 2021

(65) Prior Publication Data

US 2021/0377657 A1 Dec. 2, 2021

Related U.S. Application Data

(63) Continuation-in-part of application No. 17/388,688, filed on Jul. 29, 2021, which is a continuation of
(Continued)

(51) Int. Cl.
*A61B 5/00* (2006.01)
*H01Q 1/22* (2006.01)
(Continued)

(52) U.S. Cl.
CPC ........... *H04R 1/406* (2013.01); *A61B 5/4806* (2013.01); *A61B 5/4809* (2013.01);
(Continued)

(58) Field of Classification Search
CPC ... A61B 5/4806; A61B 5/4809; A61B 5/4815; H01Q 1/22; H01Q 21/061; H01Q 21/065;
(Continued)

(56) References Cited

U.S. PATENT DOCUMENTS 7,436,348 B2 10/2008 Nohmi
7,654,948 B2 2/2010 Kaplan et al.
(Continued)

FOREIGN PATENT DOCUMENTS

CN 207869389 9/2018
EP 2952927 12/2015
(Continued)

OTHER PUBLICATIONS

Search Report dated Mar. 19, 2020 for PCT Application No. PCT/US2019/062043.
(Continued)

*Primary Examiner* — Joseph H Feild
*Assistant Examiner* — Sharmin Akhter
(74) *Attorney, Agent, or Firm* — Schwegman Lundberg & Woessner, P.A.

(57) ABSTRACT

In an example, the present technique provides a method for processing signals from a human user in connection with a sleep state. Preferably, the method includes using information from the signals for digital cognitive behavioral therapy to improve a sleep state of the human user. In an example, the method generally includes sensing of human activities, processing information from such sensing, outputting a task to the user, monitoring a reaction from the user, and adjusting any one of the aforementioned, to improve a sleep state of the user.

39 Claims, 33 Drawing Sheets

Related U.S. Application Data application No. 16/937,348, filed on Jul. 23, 2020, now Pat. No. 11,218,800, which is a continuation of application No. 16/272,188, filed on Feb. 11, 2019, now Pat. No. 10,743,100.

(51) Int. Cl.
  *H01Q 21/06* (2006.01)
  *H04R 1/08* (2006.01)
  *H04R 1/32* (2006.01)
  *H04R 1/40* (2006.01)

(52) U.S. Cl.
  CPC .............. *A61B 5/4815* (2013.01); *H01Q 1/22* (2013.01); *H01Q 21/061* (2013.01); *H04R 1/083* (2013.01); *H04R 1/326* (2013.01); *H04S 2400/11* (2013.01)

(58) Field of Classification Search
  CPC ........ H01Q 21/28; H01Q 5/25; H01Q 21/205; H04R 1/406; H04R 1/083; H04R 1/326; H04R 2420/07; H04R 1/403; G08B 13/00; G08B 21/0423; G08B 21/0492; G08B 29/186; G08B 29/188; H04S 2400/11
  See application file for complete search history.

(56) References Cited

U.S. PATENT DOCUMENTS

| | | |
|---|---|---|
| 7,916,066 B1 | 3/2011 | Osterweil |
| 7,925,995 B2 | 4/2011 | Krumm et al. |
| 8,446,253 B2 | 5/2013 | Ramchandran et al. |
| 8,512,221 B2 | 8/2013 | Kaplan et al. |
| 8,562,526 B2 | 10/2013 | Heneghan et al. |
| 8,606,249 B1 | 12/2013 | Goodwin |
| 9,196,257 B2 | 11/2015 | Schultz-amling et al. |
| 9,309,782 B2 | 4/2016 | Kareff et al. |
| 9,311,802 B1 | 4/2016 | Chin et al. |
| 9,319,782 B1 | 4/2016 | Crump et al. |
| 9,807,725 B1 | 10/2017 | Vitus et al. |
| 9,972,917 B2 | 5/2018 | Vacanti et al. |
| 10,222,474 B1 | 3/2019 | Raring et al. |
| 10,457,161 B2 | 10/2019 | Lu-dac et al. |
| 10,568,565 B1 | 2/2020 | Kahn et al. |
| 10,574,945 B1 | 2/2020 | Seyfi et al. |
| 10,623,897 B1 | 4/2020 | Wu et al. |
| 10,743,100 B1 | 8/2020 | Eckert et al. |
| 10,810,850 B2 | 10/2020 | Eckert et al. |
| 10,928,498 B1 | 2/2021 | Li et al. |
| 10,936,880 B2 | 3/2021 | Eronen et al. |
| 11,004,567 B2 | 5/2021 | Eckert et al. |
| 11,043,038 B1 | 6/2021 | Ngai et al. |
| 11,143,743 B2 | 10/2021 | Eckert et al. |
| 11,163,052 B2 | 11/2021 | Eckert et al. |
| 11,175,393 B2 | 11/2021 | Eckert et al. |
| 11,184,738 B1 | 11/2021 | Rigazio et al. |
| 11,218,800 B2 | 1/2022 | Eckert et al. |
| 11,462,330 B2 | 10/2022 | Eckert et al. |
| 11,776,696 B2 | 10/2023 | Eckert et al. |
| 2005/0007269 A1 | 1/2005 | Carrara et al. |
| 2005/0154929 A1 | 7/2005 | Ahrens et al. |
| 2006/0053110 A1 | 3/2006 | Mcdonald et al. |
| 2006/0152404 A1 | 7/2006 | Fullerton et al. |
| 2006/0284791 A1 | 12/2006 | Chen et al. |
| 2006/0291473 A1 | 12/2006 | Chase et al. |
| 2007/0205937 A1 | 9/2007 | Thompson et al. |
| 2007/0219059 A1 | 9/2007 | Schwartz et al. |
| 2007/0297695 A1 | 12/2007 | Aratani et al. |
| 2009/0167862 A1 | 7/2009 | Jentoft et al. |
| 2009/0203972 A1 | 8/2009 | Heneghan et al. |
| 2009/0224963 A1 | 9/2009 | Nakanishi |
| 2009/0264715 A1 | 10/2009 | Auphan |
| 2010/0026479 A1 | 2/2010 | Tran |
| 2010/0048256 A1 | 2/2010 | Huppi et al. |
| 2010/0141506 A1 | 6/2010 | Gulden et al. |
| 2010/0152600 A1 | 6/2010 | Droitcour et al. |
| 2010/0321229 A1 | 12/2010 | Dwelly et al. |
| 2011/0077758 A1 | 3/2011 | Tran et al. |
| 2011/0187816 A1 | 8/2011 | Shimizu |
| 2011/0190594 A1* | 8/2011 | Heit ............... G16H 40/67 600/26 |
| 2011/0199254 A1 | 8/2011 | Bishop et al. |
| 2011/0242305 A1 | 10/2011 | Peterson et al. |
| 2012/0044355 A1 | 2/2012 | Jamtgaard et al. |
| 2012/0065944 A1 | 3/2012 | Nielsen et al. |
| 2012/0161968 A1 | 6/2012 | Bodapati et al. |
| 2012/0275236 A1 | 11/2012 | Hess et al. |
| 2013/0053653 A1 | 2/2013 | Cuddihy et al. |
| 2013/0207831 A1 | 8/2013 | Fullerton |
| 2013/0278416 A1 | 10/2013 | Button et al. |
| 2014/0022940 A1 | 1/2014 | Apte et al. |
| 2014/0155705 A1 | 6/2014 | Papadopoulos et al. |
| 2014/0207292 A1 | 7/2014 | Ramagem et al. |
| 2014/0316261 A1 | 10/2014 | Lux et al. |
| 2014/0335893 A1 | 11/2014 | Ronen |
| 2014/0375521 A1 | 12/2014 | Andujar Linares et al. |
| 2015/0022349 A1 | 1/2015 | Smith et al. |
| 2015/0079809 A1 | 3/2015 | Silva et al. |
| 2015/0182162 A1* | 7/2015 | Zhao ............... A61B 5/1118 600/595 |
| 2015/0233598 A1 | 8/2015 | Shikii et al. |
| 2015/0238137 A1 | 8/2015 | Eyal et al. |
| 2015/0245167 A1 | 8/2015 | Bobrow et al. |
| 2015/0265922 A1 | 9/2015 | Yamane et al. |
| 2015/0286948 A1 | 10/2015 | Luca et al. |
| 2015/0301167 A1 | 10/2015 | Sentelle et al. |
| 2015/0302323 A1 | 10/2015 | Connolly |
| 2015/0310726 A1 | 10/2015 | Sager et al. |
| 2016/0055332 A1 | 2/2016 | Jeansonne et al. |
| 2016/0151603 A1 | 6/2016 | Shouldice et al. |
| 2016/0249021 A1 | 8/2016 | Mcaleenan et al. |
| 2016/0337441 A1 | 11/2016 | Bloomquist et al. |
| 2016/0360362 A1 | 12/2016 | Do et al. |
| 2016/0377705 A1 | 12/2016 | Zack et al. |
| 2017/0005958 A1 | 1/2017 | Frenkel et al. |
| 2017/0038456 A1 | 2/2017 | Smith |
| 2017/0039517 A1 | 2/2017 | Amann et al. |
| 2017/0108581 A1 | 4/2017 | Morley |
| 2017/0328995 A1 | 11/2017 | Marschalkowski et al. |
| 2018/0012080 A1 | 1/2018 | Glaser et al. |
| 2018/0031374 A1 | 2/2018 | Hepler et al. |
| 2018/0043247 A1 | 2/2018 | Vandonkelaar |
| 2018/0050800 A1 | 2/2018 | Boykin et al. |
| 2018/0064388 A1* | 3/2018 | Heneghan ............ A61B 5/743 |
| 2018/0103859 A1 | 4/2018 | Provenzano |
| 2018/0116606 A1 | 5/2018 | Li et al. |
| 2018/0143320 A1 | 5/2018 | Steever et al. |
| 2018/0167140 A1 | 6/2018 | Brandt-pearce et al. |
| 2018/0202686 A1 | 7/2018 | Ahuja et al. |
| 2018/0204470 A1 | 7/2018 | Rezvani et al. |
| 2018/0245927 A1 | 8/2018 | Frish et al. |
| 2018/0295535 A1 | 10/2018 | Kavars et al. |
| 2018/0322351 A1 | 11/2018 | Shaker |
| 2018/0351775 A1 | 12/2018 | Zhang et al. |
| 2018/0357871 A1 | 12/2018 | Siminoff |
| 2018/0374143 A1 | 12/2018 | Williamson et al. |
| 2019/0019295 A1 | 1/2019 | Lehtiniemi et al. |
| 2019/0033440 A1 | 1/2019 | Boolos et al. |
| 2019/0043466 A1 | 2/2019 | Masterson et al. |
| 2019/0053707 A1 | 2/2019 | Lane et al. |
| 2019/0057777 A1 | 2/2019 | Joshi et al. |
| 2019/0069838 A1 | 3/2019 | Xin et al. |
| 2019/0072669 A1 | 3/2019 | Duque Biarge et al. |
| 2019/0088098 A1 | 3/2019 | Gangumalla et al. |
| 2019/0108913 A1 | 4/2019 | Coke et al. |
| 2019/0146077 A1 | 5/2019 | Kravets et al. |
| 2019/0158494 A1 | 5/2019 | Nakayama et al. |
| 2019/0159960 A1 | 5/2019 | Nakata et al. |
| 2019/0197866 A1 | 6/2019 | Mukundala et al. |
| 2019/0207650 A1 | 7/2019 | Kearney et al. |
| 2019/0219403 A1 | 7/2019 | Hu |
| 2019/0278555 A1 | 9/2019 | Carvajal et al. |

(56) References Cited

U.S. PATENT DOCUMENTS

| | | | |
|---|---|---|---|
| 2019/0279479 A1 | 9/2019 | Reunamaki et al. |
| 2019/0289417 A1 | 9/2019 | Tomlin et al. |
| 2019/0302252 A1 | 10/2019 | Santra et al. |
| 2019/0317239 A1 | 10/2019 | Olsson et al. |
| 2019/0347925 A1 | 11/2019 | Faltaous et al. |
| 2019/0372363 A1 | 12/2019 | Cutcher et al. |
| 2019/0375103 A1 | 12/2019 | Cui et al. |
| 2020/0022646 A1 | 1/2020 | Brown |
| 2020/0053574 A1 | 2/2020 | Hasan et al. |
| 2020/0054236 A1 | 2/2020 | Qi et al. |
| 2020/0079363 A1 | 3/2020 | Frederick et al. |
| 2020/0088870 A1 | 3/2020 | Tsiklauri et al. |
| 2020/0097006 A1 | 3/2020 | Liu et al. |
| 2020/0097092 A1 | 3/2020 | Tzadok |
| 2020/0103486 A1 | 4/2020 | Knaappila |
| 2020/0103513 A1 | 4/2020 | Knaappila |
| 2020/0103516 A1 | 4/2020 | Kim et al. |
| 2020/0143123 A1 | 5/2020 | Shen et al. |
| 2020/0158819 A1 | 5/2020 | Joshi et al. |
| 2020/0158849 A1 | 5/2020 | Joshi et al. |
| 2020/0168339 A1 | 5/2020 | Correnti |
| 2020/0196110 A1 | 6/2020 | Jakobsson |
| 2020/0204541 A1 | 6/2020 | Nair et al. |
| 2020/0234030 A1 | 7/2020 | Baheti et al. |
| 2020/0256972 A1 | 8/2020 | Eckert et al. |
| 2020/0260180 A1 | 8/2020 | Eckert et al. |
| 2020/0264278 A1 | 8/2020 | Eckert et al. |
| 2020/0265698 A1 | 8/2020 | Eckert et al. |
| 2020/0271747 A1 | 8/2020 | Wu et al. |
| 2020/0272268 A1 | 8/2020 | Shin et al. |
| 2020/0310749 A1 | 10/2020 | Miller et al. |
| 2020/0397310 A1 | 12/2020 | Gu et al. |
| 2021/0011121 A1 | 1/2021 | Arbabian et al. |
| 2021/0033724 A1 | 2/2021 | Zhang et al. |
| 2021/0035425 A1 | 2/2021 | Eckert et al. |
| 2021/0037315 A1 | 2/2021 | Eckert et al. |
| 2021/0046650 A1 | 2/2021 | Deyle et al. |
| 2021/0055385 A1 | 2/2021 | Rimini et al. |
| 2021/0063214 A1 | 3/2021 | Li et al. |
| 2021/0065891 A1 | 3/2021 | Li et al. |
| 2021/0096216 A1 | 4/2021 | Rigazio et al. |
| 2021/0150873 A1 | 5/2021 | Shouldice et al. |
| 2021/0194206 A1 | 6/2021 | Raring et al. |
| 2021/0197834 A1 | 7/2021 | Shaker et al. |
| 2021/0249140 A1 | 8/2021 | Eckert et al. |
| 2021/0358637 A1 | 11/2021 | Devdas |
| 2021/0360344 A1 | 11/2021 | Eckert et al. |
| 2022/0016519 A1 | 1/2022 | Van Der Steen et al. |
| 2022/0051677 A1 | 2/2022 | Park et al. |
| 2022/0075051 A1 | 3/2022 | Woo et al. |
| 2022/0236395 A1 | 7/2022 | Eckert et al. |
| 2022/0268916 A1 | 8/2022 | Nagpal |
| 2022/0384047 A1 | 12/2022 | Eckert et al. |
| 2023/0386673 A1 | 11/2023 | Eckert et al. |
| 2023/0388749 A1 | 11/2023 | Rigazio et al. |
| 2024/0004054 A1 | 1/2024 | Rigazio et al. |

FOREIGN PATENT DOCUMENTS

| | | |
|---|---|---|
| GB | 2520169 | 5/2015 |
| KR | 101536249 | 7/2015 |
| WO | 2007143535 | 12/2007 |
| WO | 2016193972 | 12/2016 |
| WO | 2020102813 | 5/2020 |

OTHER PUBLICATIONS

Ganis, "A Portable 3D Imaging FMCW MIMO Radar Demonstrator with a 24×24 Antenna Array for Medium Range Applications", (2018), 15 pgs.

Hannun, Awni, "Sequence-tosequence speech recognition with time-depth separable convolutions", arXiv:1904.02619, (Apr. 2019), 5 pgs.

He, Kaiming, "Deep Residual Learning for Image Recognition", arXiv preprint, arXiv:1512.03385v1 [cs.CV], (Dec. 10, 2015), 12 pgs.

Lee, "Design and Performance of a 24-GHz Switch-Antenna Array FMCW Radar System for Automotive Applications", (2010), 8 pgs.

Lien, Jaime, "Soli: Ubiquitous Gesture Sensing with Millimeter Wave Radar", ACM Transactions on Graphics (TOG), vol. 35 Issue 4, Article 142, (Jul. 2016), 19 pgs.

Ravanelli, M, "Speech and Speaker Recognition from Raw Waveform with SincNet", arXiv:1812.05920v2, (Feb. 15, 2019), 5 pgs.

Sherman, "An FPS-115 PAVE PAWS Radar", (2000), 4 pgs.

Tian, Yonglong, "RF-Based Fall Monitoring Using Convolutional Neural Networks", Proc. ACM Interact. Mob. Wearable Ubiquitous Technol., vol. 2, No. 3, Article 137, (Sep. 2018), 24 pgs.

Tokoro, S, "Electronically scanned millimeter-wave radar for pre-crash safety and adaptive cruise control system", In IEEE IV2003 Intelligent Vehicles Symposium, (Jun. 2003), 6 pgs.

Yang, "Vital Sign and Sleep Monitoring Using Millimeter Wave", ACM Transactions on Sensor Networks, vol. 13, No. 2, Artical 14, (Apr. 2017), 32 pgs.

Rahman, Tauhidur, "A Contactless Unobtrusive Sleep Sensing System Using Short-Range Doppler Radar", UBICOMP '15, Osaka, Japan, (Sep. 7-11, 2015), 12 pgs.

"U.S. Appl. No. 16/272,188, Non Final Office Action mailed Dec. 23, 2019", 18 pgs.

"U.S. Appl. No. 16/272,188, Response filed Mar. 19, 2020 to Non Final Office Action mailed Dec. 23, 2019", 12 pgs.

"U.S. Appl. No. 16/272,188, Notice of Allowance mailed Apr. 9, 2020", 13 pgs.

"U.S. Appl. No. 16/937,348, Non Final Office Action mailed Jul. 21, 2021", 8 pgs.

"U.S. Appl. No. 16/937,348, Response filed Aug. 4, 2021 to Non Final Office Action mailed Jul. 21, 2021", 10 pgs.

"U.S. Appl. No. 16/937,348, Notice of Allowance mailed Aug. 25, 2021", 5 pgs.

Chen, "Google Translation of CN207869389", (Sep. 2018), 5 pgs.

"U.S. Appl. No. 16/279,949, Examiner Interview Summary mailed Jan. 11, 2023", 2 pgs.

Khan, "A Detailed Algorithm for Vital Sign Monitoring of a Stationary Non-Stationary Human Through IR-UWB Radar", Sensors 2017, (Feb. 4, 2017), 15 pgs.

Suzuki, "An Approach to a Non-Contact Vital Sign Monitoring Using Dual-Frequency Microwave Radars for Elderly Care", J. Biomedical Science and Engineering 6, (2013), 704-711.

"International Application Serial No. PCT US2022 039857, International Search Report mailed Jan. 3, 2023", 3 pgs.

"International Application Serial No. PCT US2022 039857, Written Opinion mailed Jan. 3, 2023", 5 pgs.

Wang, Zhihua, "A Review of Wearable Technologies for Elderly Care that Can Accurately Track Indoor Position, Recognize Physical Activities and Monitor Vital Signs in Real Time", (Feb. 10, 2017), 36 pgs.

"FCC Equipment Test Report of 10.525 GHz field disturbance sensor in SleepScore Max Bedside Monitor", Compliance Engineering Ireland LTD, (Sep. 20, 2013), 25 pgs.

Cippitelli, E, et al., "Radar and RGB-Depth Sensors for Fall Detection: A Review", in IEEE Sensors Journal, vol. 17, No. 12, (Jun. 15, 2017), 3585-3604.

Li, et al., "Radar Remote Monitoring of Vital Signs", IEEE Microwave Magazine, (Feb. 2009), 47-56.

Li, et al., "Through-Wall Detection of Human Being's Movement by UWB Radar", IEEE GeoScience and Remote Sensing Letters, vol. 9, No. 6, (Nov. 2012), 1079-1083.

Oladimeji, Onalaja, "Advances in UWB-Based Indoor Position Estimation and Its Application in Fall Detection", Ph.D. Degree Thesis, London South Bank University, (Jun. 2015), 190 pgs.

* cited by examiner

| Chip parameters | Setting |
| --- | --- |
| Pulses Per Step | 1 |
| Iterations | 236 |
| DAC Min | 994 |
| DAC Max | 1054 |
| DAC Step | 1 |
| PRF Div | 16 |
| DAC Settle | 1 |
| Frame rate (fps) | 330 |
| Total frame time (ms) | 1.013465021 |
| X4 max FPS (Hz) | 986.7138773 |
| X4 duty cycle (%) | 33.44434568 |

FIG. 10

| Parameter | Description | Value | Unit |
|---|---|---|---|
| fc | Center frequency | 24.125 | GHz |
| fStart | Start frequency | 24.000 | GHz |
| fStop | Stop frequency | 24.250 | GHz |
| TRamp Up | Up chirp duration | 32/64/128/256 | µs |
| TRampDo | Down chirp duration | 16/32/64/128 | µs |
| Tp | Chirp repetition interval | <= 1 | ms |
| Np | Number of chirps per Tp | 1 ('ExtTrigUp' mode) | |
| N | Number of samples for one chirp | 64/128 | |

Note : with the above combination of settings max Fs needed is 4 MHz, however if there is significant cost savings we can reduce Fs to minimum 1 MHz.

FIG. 16

FIGURE 25
Button # 1 : Press the Button to make an Outgoing call
Button # 2 : Press the Button to receive the Incoming Call or Mute the AIC Audio Codec
Button # 3 : Volume up for AIC Audio Codec
Button # 3 : Volume Down for AIC Audio Codec
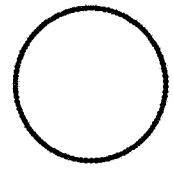 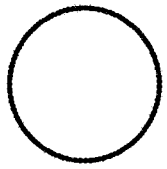 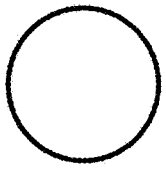 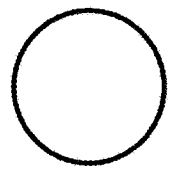

FIGURE 27: LTE Interface of TAP

SYSTEM AND METHOD FOR PROCESSING MULTI-DIRECTIONAL SIGNALS AND FEEDBACK TO A USER TO IMPROVE SLEEP

CROSS-REFERENCE TO RELATED APPLICATIONS

The present application is a continuation-in-part of U.S. application Ser. No. 17/388,688, filed Jul. 29, 2021, which is a continuation of U.S. application Ser. No. 16/937,348, filed Jul. 23, 2020, which is a continuation of U.S. application Ser. No. 16/272,188, filed Feb. 11, 2019, and issued as U.S. Pat. No. 10,743,100 on Aug. 11, 2020, and is related to U.S. application Ser. No. 16/103,829, filed on Aug. 14, 2018, U.S. application Ser. No. 16/194,155, filed on Nov. 16, 2018, and U.S. application Ser. No. 16/194,166, filed Nov. 16, 2018, each of which is hereby incorporated by reference in its entirety.

BACKGROUND

The present invention relates to techniques, including a method, and system, for processing audio, motion, ultra wide band ("UWB") and frequency modulated continuous wave ("FMCW") signals using a plurality of antenna array, and other conditions and events. More particularly, the present techniques can be combined with feedback for digital cognitive behavioral therapy for improving sleep, as an example. Merely by way of examples, various applications can include daily life, sleep, and others.

Various conventional techniques exist for monitoring people within a home or building environment. Such techniques include use of cameras to view a person. Other techniques include a pendant or other sensing device that is placed on the person to monitor his/her movement. Examples include Personal Emergency Response Systems (PERS) devices such as LifeAlert® and Philips® Life-Line—each of which are just panic buttons for seniors to press in case of an emergency. Other techniques have been proposed to monitor sleep. Unfortunately, all of these techniques have limitations. That is, each of these techniques fails to provide a reliable and high quality signal to accurately detect a key human activities of the person being monitored. Additionally, many of the techniques fail to provide meaningful feedback or counter measures to counteract any undesirable events.

From the above, it is seen that techniques for identifying and monitoring a person is highly desirable.

SUMMARY

According to the present invention, techniques related to a method, and system, for processing audio, UWB, FMCW signals using a plurality of antenna array, and other signals and events are provided. More particularly, the present techniques can be combined with feedback for digital cognitive behavioral therapy for improving sleep, as an example. Merely by way of examples, various applications can include daily life, sleep, and others.

In an example, the present technique provides a method for processing signals from a human user in connection with a sleep state. Preferably, the method includes using information from the signals for digital cognitive behavioral therapy to improve a sleep state of the human user. In an example, the method generally includes sensing of human activities, processing information from such sensing, outputting a task to the user, monitoring a reaction from the user, and adjusting any one of the aforementioned, to improve a sleep state of the user.

The above examples and implementations are not necessarily inclusive or exclusive of each other and may be combined in any manner that is non-conflicting and otherwise possible, whether they be presented in association with a same, or a different, embodiment or example or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above examples implementations are illustrative, rather than limiting.

BRIEF DESCRIPTION OF THE DRAWINGS

FIG. 10 is a simplified diagram of electrical parameters according to an example for the ultra-wide band module in the present invention.

FIG. 16 is a table illustrating device parameters according to examples of the present invention.

FIG. 25 is a simplified diagram of a user interface according to an example of the present invention.

DETAILED DESCRIPTION OF THE EXAMPLES

According to the present invention, techniques related to a method, and system, for processing UWB and FMCW signals using a plurality of antenna array are provided. In an example, the plurality of antenna array, including a receiving antenna array and a transmitting antenna array configured to capture and transmit signals in an omni-directional manner. Merely by way of examples, various applications can include daily life, sleep, and others.

Figure 1:
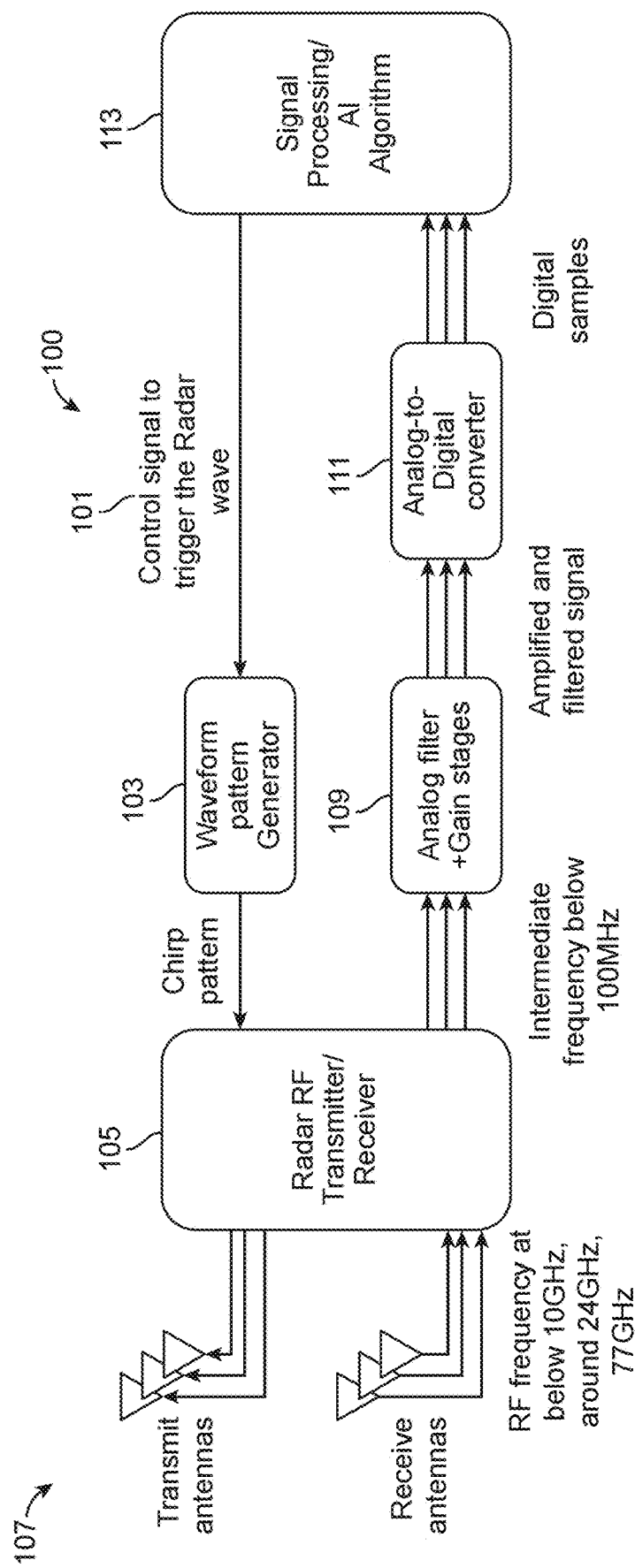
FIG. 1 is a simplified diagram of a radar/wireless back-scattering sensor system according to an example of the present invention.

FIG. 1 is a simplified diagram of a radar/wireless backscattering sensor system 100 according to an example of the present invention. This diagram is merely an example, which should not unduly limit the scope of the claims herein. In an example, the system is a wireless backscattering detection system. The system has a control line 101 coupled to a processing device. The control line is configured with a switch to trigger an initiation of a wireless signal. In an example, the system has a waveform pattern generator 103 coupled to the control line. The system has an rf transmitter 105 coupled to the waveform pattern generator. The system has transmitting and receiving antenna 107. In an example, the system has a transmitting antenna coupled to the rf transmitter and an rf receiver 105, which is coupled to an rf receiving antenna. In an example, the system has an analog front end comprising a filter 109. An analog to digital converter 111 coupled to the analog front end. The system has a signal-processing device 113 coupled to the analog to digital converter. In a preferred example, the system has an artificial intelligence module 113 coupled to the signal-processing device. The module is configured to process information associated with a backscattered signal captured from the rf receiving antenna. Further details of the present system can be found throughout the specification and more particularly below.

Antenna

In an example, multiple aspects of antenna design can improve the performance of the activities of daily life ("ADL") system. For example in scanning mode the present technique continuously looks for moving human targets (or user) to extract ADL or fall. Since these can happen anywhere in the spatial region of a home, the present system has antennas that have wide field of view. Once the human target is identified, the technique focuses signals coming only from that particular target and attenuate returns from all other targets. This can be done by first estimating location of the target from our technique using wide field of view antennas and then focusing RF energy on the specific target of interest once it has been identified. In an example, the technique can either electronically switch a different antenna that has narrow field of view or could use beam forming techniques to simultaneously transmit waves from multiple transmit antenna and control their phase such that the RF energy constructively builds around the target of interest where as it destructively cancels everywhere else. This return will be much cleaner and can boost the performance of our ADL+ fall+vital sign sensors.

In another example considers the layout of the antennas itself. In an example, the technique places transmit and receive antennas in various different physical configurations (ULA, circular, square, etc.), that can help us establish the direction from which the radar signal returns, by comparing phases of the same radar signal at different receiving antennas. The configurations can play a role because different configurations enable direction of arrival measurement from different dimensions. For example, when the human target falls the vertical angle of arrival changes from top to bottom, therefore a vertical ULA is better suited to capture that information. Likewise during walking horizontal angle of arrival of the signal varies more therefore it makes sense to use horizontal ULA is more sensitive and therefor can provide additional information for our algorithm. Of course, there can be other variations, modifications, and alternatives.

RF Unit

In an example, the wireless RF unit can be either pulsed doppler radar or frequency modulated continuous wave (FMCW) or continuous wave doppler (CW). In an example, on the transmit side it will have standard RF units like VCO, PLL, among others. On the receive side it can have matched filter, LNA, mixer, and other elements. The multiple antennas can be either driven by a single transmit/receive chain by sharing it in time or have one each chain for each of the antennas.

Waveform Unit

In an example, waveform pattern generator generates control signals that define the type of radar signal that is generated by the radar RF unit. For example for FMCW, it can generate triangular wave of specific slope and period, which will linearly sweep the frequency of the RF unit according to this parameter. For a pulsed doppler radar, the technique will hold generate pulse of specific width and period, which will modulate the RF output accordingly.

Baseband Unit

In an example, the gain and filter stage filters the radar returns to remove any unwanted signals and then amplifies the remaining signal with different techniques. For example, the present artificial intelligence or AI technique can determine what target is desirably tracked and provide feedback to the AI technique, that will filter out radar return from any and all other signals except for the signal that is desirably tracked. If human target is moving the return signal will be fluctuating, in that case, the technique applies automatic gain control (AGC) to find the optimal gain, so that entire dynamic range of ADC in the subsequent stage is satisfied. In an example, the return signal is converted to digital samples by analog-to-digital converters (ADC), among other front-end elements.

Figure 2:
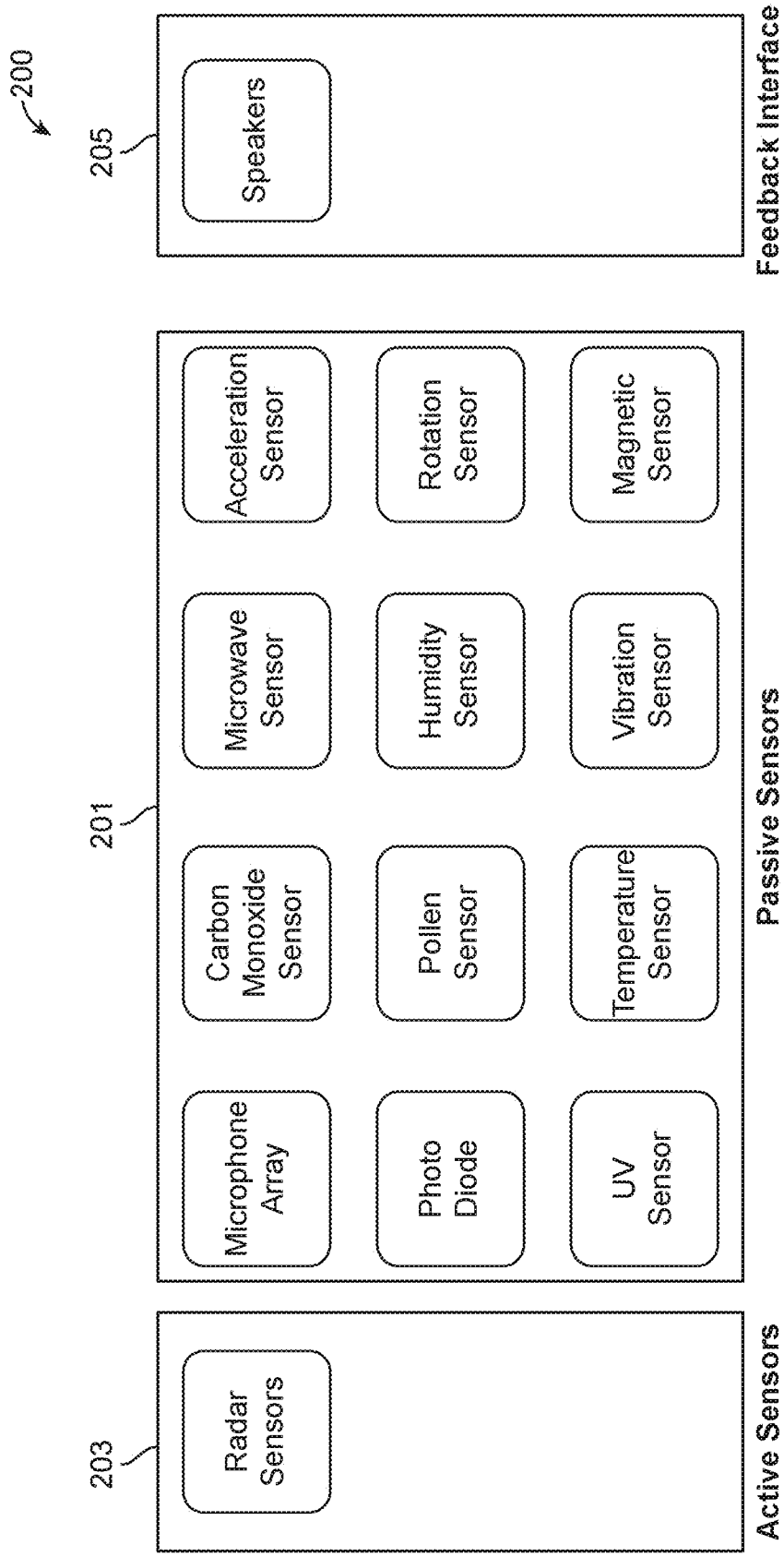
FIG. 2 is a simplified diagram of a sensor array according to an example of the present invention.

FIG. 2 is a simplified diagram of a sensor array 200 according to an example of the present invention. This diagram is merely an example, which should not unduly limit the scope of the claims herein. Shown is a sensor array. The sensor array includes a plurality of passive sensors 201. In an example, the plurality of passive sensors are spatially disposed in spatial region of a living area. The sensor array has active sensors, such as one or more radar sensors 203. Additionally, the array has a feedback interface 205, such as a speaker for calling out to a human target in the spatial region of the living area.

In an example, the present technique is provided to identify various activities in home using non-wearable. In an example, the technique is at least privacy intrusive as possible, and will use sensors that are less intrusive. Examples of sensors can include, without limitation, a wireless backscatter (e.g., radar, WiFi.), audio (e.g., microphone array, speaker array), video (e.g., PTZ mounted, stereo), pressure mats, infrared, temperature, ultraviolet, humidity, pressure, smoke, any combination thereof, and others.

Active Sensor for RADAR

In an example, the technique can use wireless backscattering to measure motion of human, a location, and an environmental state, such as door opening/closing, or other environmental condition. In an example, the wireless backscattering can also be used to measure a vital sign, such as a heart rate and respiration rate, among others. In an example, the wireless techniques can work in non-line of sight, and is non-intrusive compared to camera or microphone, or others. In an example, the technique can use radar\backscatter sensor for two purposes (1) to find the location of an action; and (2) sense different activities associated with the action. Of course, there can be other variations, modifications, and alternatives.

In an example, the present technique and system includes a radar system that operates on multiple frequency bands, such as below 10 GHz, around 24 GHz, 60 GHz, 77-81 GHz, among others. In an example, different frequency interacts differently with various objects in our environment. In an example, available signal bandwidth and permissible signal power are also regulated differently at different frequency bands. In an example, the present techniques optimally combine reflections coming from a reflector from multiple frequency bands to achieve large coverage, and/or improve accuracy. Of course, there can be other variations, modifications, and alternatives.

In an example, each radar is working at a particular frequency band will be using multiple transmit and receive antennas, as shown. In an example, using these multiple transmitters, the technique can perform transmit beam forming to concentrate radar signal on a particular target. In an example, the technique uses multiple receivers to collect reflected signals coming from various reflectors (e.g., human body, walls). After further processing this will allow us to find the direction of the reflector with respect to the radar. In an example, the technique also uses multiple transmitter and receiver to form virtual array, this will allow emulate the radar array with large element by using small number of transmitter and receiver chains. The main benefit is to improve the angle resolution without using a large array, saving space and component cost. In an example, different antenna array configurations to improve coverage (using beam forming) or add 3D localization capability (using 2-D array) are included.

In an example using standard radar signal modulation techniques, such as FMCW/UWB, on MIMO radar, the technique will first separate signals coming from different range and angle. The technique will then identify static reflectors, such as chairs, walls, or other features, from moving ones, such as human targets, pets, or the like. For moving objects that are tracked, the technique will further process signals for each of the reflectors. As an example, the technique will use different techniques to extract raw motion data (e.g., like spectrogram). In an example, the technique will apply various filtering process to extract periodic signals generated by vital signs, such as heart rate, respiration rate, among others. In an example, both the raw motion data and extracted vital signs will be passed to a downstream process, where they are combined with data from other sensors, such as radar outputs operating at different frequency or completely different sensors to extract higher insights about the environment. Of course, there can be other variations, modifications, and alternatives.

Audio Sensor

In an example, the present technique uses a sensor array that has a multiple microphone array. In an example, these microphones will be used to ascertain the direction of arrival of any audio signal in the environment. In an example, the microphone in conjunction with other sensors, such as radar, will be vital in performing two tasks: 1st it will augment radar signal to identify various activities (walking produces a different sound than sitting), if the target is watching TV it is much easier to ascertain it with audio signal; and 2nd in case of emergency like fall, the technique can use the radar signal to identify the location of the fall and then beam form microphone array towards that location, so that any audio signal produced by the target can be captured. Of course, there can be other variations, modifications, and alternatives.

Sensor Fusion and Soft Sensors

In addition to a radar sensor, which is consider as active sensors the present sensor system (e.g., box, boxes) will also have additional passive sensors that captures the sound, chemical signature, environmental conditions. Each of these of the sensors captures different context about the home that the human being tracking is living in or occupying. In an example, the UV sensor can monitor how often the sunlight comes in the room. In an example, light sensors determine a lighting condition of the human's home or living area.

In an example, a microphone array can have many functions, such as use to sense sound in the room, to figure out how long the human has spent watching TV, or how many time they went to bathroom by listening to the sound of toilet flushing or other audio signature. In an example, the present technique can use creative solutions where it can use the active sensor to find the location of the person and then tune the microphone array to enhance the sound coming from that location only, among other features. In an example, the technique can call the sensors that are derived from the hardware sensors using specific algorithms as software sensors or soft sensors. So the same hardware sensors can be used for many different applications by creating different software sensors. Here the software sensors can combine signals from one or more sensors and then apply sensor fusion and AI techniques to generate the desired output. Of course, there can be other variations, modifications, and alternatives.

Soft Sensor for Detecting Cooking and Eating Habits

In example, radar sensors can determine information about a human's location within a home, like if they are in kitchen area, or other. In an example, when the human target turns on the microphone oven, it generates specific RF signature that can be tracked. In an example, the technique can combine this information to infer if the human target walked to the kitchen and turned on the microphone. Likewise, when the human target prepares food in kitchen he/she can make lot of specific noise like utensils clattering, chopping, or other audio signature. So if a human target goes to kitchen spends sometime time in the kitchen, and the present microphone pick these sounds, the technique can infer that food is cooking or other activity.

Soft Sensor for Detecting Bathroom Habits

In an example, toileting frequency can be a very valuable indication of one's wellness. The present technique can track if a human went to the bathroom using the radar or other sensing techniques. In an example, additionally, the technique can pick sound signature of toilet flushing. In an example, the technique combines these two pieces of information, which can be correlated to toileting frequency. In an example, similarly, bathing is a unique activity that requires 4-5 minutes of specific movements. By learning those patterns, the technique can figure out ones bathing routines.

Soft Sensor for Detecting Mobile Habits

In an example, different sensors are triggered by different motion of a human target. In an example, radar can detect human fall by looking at micro doppler patterns generating by different part of the target during falls. In an example, the technique can also simultaneously hear a fall from microphone arrays and vibration sensors. In an example, the technique can also detect how pace of movement changes for an individual over a long duration by monitoring the location information provided by radar or other sensing technique. In an example, likewise, the technique can gather unstable transfers by analyzing the gait of the target. In an example, the technique can find front door loitering by analyzing the radar signal pattern. In an example, the technique can figure out immobility by analyzing the radar return. In this case, the technique can figure out the target's presence by analyzing the target's vital signs, such as respiration rate or heart rate or by keeping track of the bread crumb of the target's location trace.

In any and all of the above cases, the technique can also learn about the exact environmental condition that triggered a particular state. For example, the technique can figure out whether a human target was immobile because the target was watching TV or a video for long duration or the target was simply spending a lot of time in their bed. And these can be used to devise incentives to change the target's behavioral pattern for better living.

Soft Sensor for Detecting Vital Signs

In an example, the technique can estimate vital signs of a person by sensing the vibration of the target's body in response to the breathing or heart beat, each of the actions results in tiny phase change in the radar return signals, which can be detected. In an example, the technique will use several signal processing techniques to extract them. Of course, there can be other variations, modifications, and alternatives.

In an example, different frequency radio wave interact with environment differently. Also phase change due to vital signs (HR,RR) differs by frequency, for example phase change for a 77 GHz radar is much higher than for a 10 GHz radar. Thus 77 GHz is more appropriate for estimating heart-beat more accurately. But higher frequency typically attenuates much more rapidly with distance. Therefore, lower frequency radar can have much larger range. By using multi-frequency radar in the present technique can perform these vital trade-offs.

Soft Sensor for Detecting Sleeping Habits

In an example, the present radar sensors can detect motions that are generated during sleep, such as tossing and turning. In an example, radar sensors can also sense vital signs like respiration rate and heart rate as described earlier. In an example, now combining the pattern of toss and turn and different breathing and heart beat pattern, the technique can effectively monitor the target's sleep. Additionally, the technique can now combine results from passive sensors, such as a thermometer, UV, photo diode, among others, to find correlation between certain sleep pattern and the environmental conditions. In an example, the technique can also use the sleep monitor soft sensor to learn about day/night reversal of sleep, and the associated environmental condition by looking at different passive sensors. In an example, the techniques can be valuable in providing feedback to improve the human target's sleep. For example, the technique can determine or learn that certain environmental condition results in better sleep and prescribe that to improve future sleep. Further details of a sleep process can be found throughout the present specification and more particularly below.

Soft Sensor for Security Applications

In an example, the technique can repurpose many of the sensors described before for security applications. For a security application, the technique determines where one or more person is located, which can be detected using a presence detection sensor that is built on top of radar signals. In an example, the technique can eliminate one or many false positive triggered by traditional security systems. For example, is a window is suddenly opened by a wind the technique (and system) will look at presence of human in the vicinity before triggering the alarm. Likewise, combination of vital signs, movement patterns, among others, can be used a biometric to identify any human target. If an unknown human target is detected in the vicinity at certain time of the day, the technique can trigger an alarm or alert.

In an example, any one of the above sensing techniques can be combined, separated, or integrated. In an example, in addition to radar and audio sensors, other sensors can be provided in the sensor array. Of course, there can be other variations, modifications, and alternatives.

Figure 3:
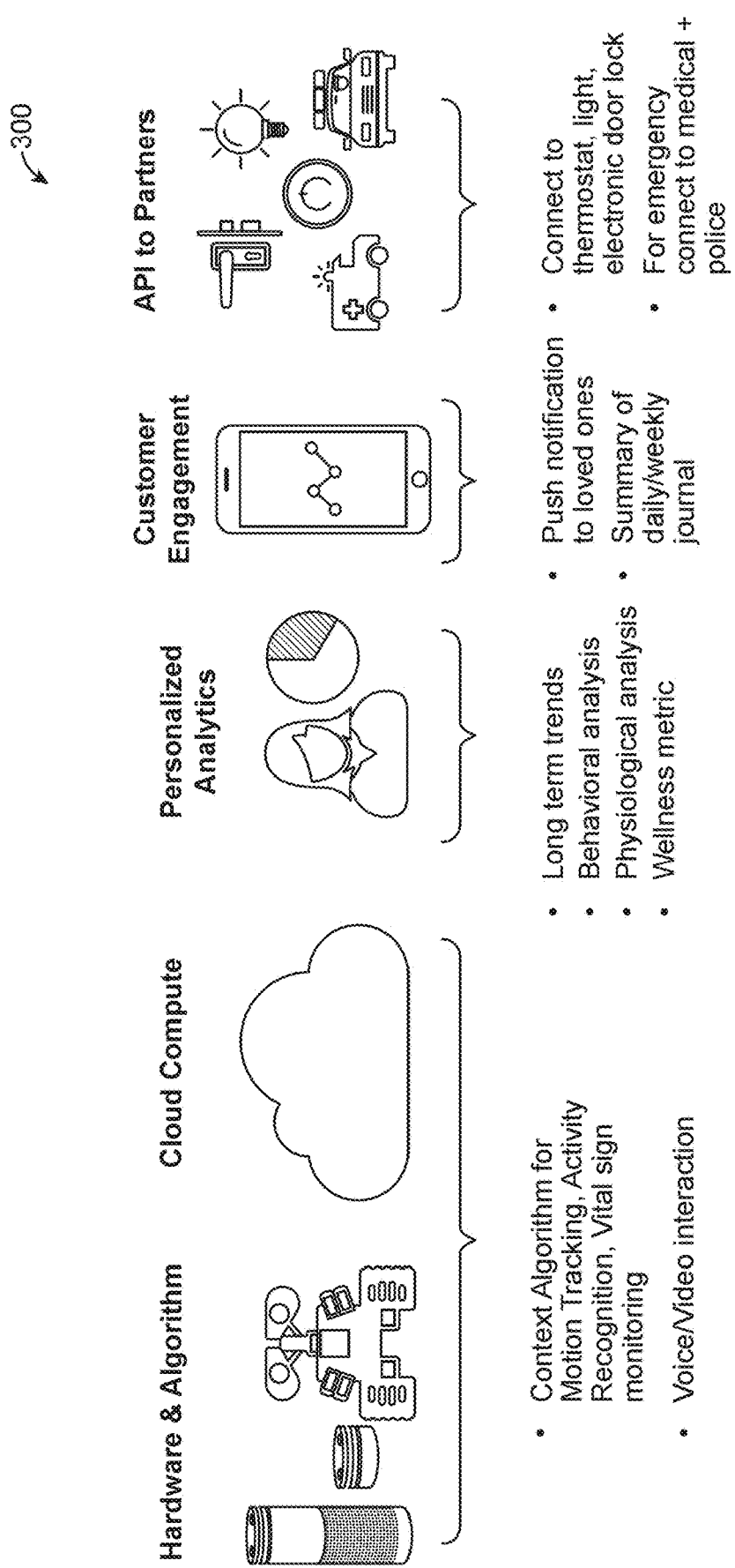
FIG. 3 is a simplified diagram of a system according to an example of the present invention.

FIG. 3 is a simplified diagram of a system 300 according to an example of the present invention. This diagram is merely an example, which should not unduly limit the scope of the claims herein. As shown, the system has hardware and method (e.g., algorithm), cloud computing, personalized analytics, customer engagement, and an API to various partners, such as police, medical, and others. Further details of the present system can be found throughout the present specification and more particularly below.

Figure 4:
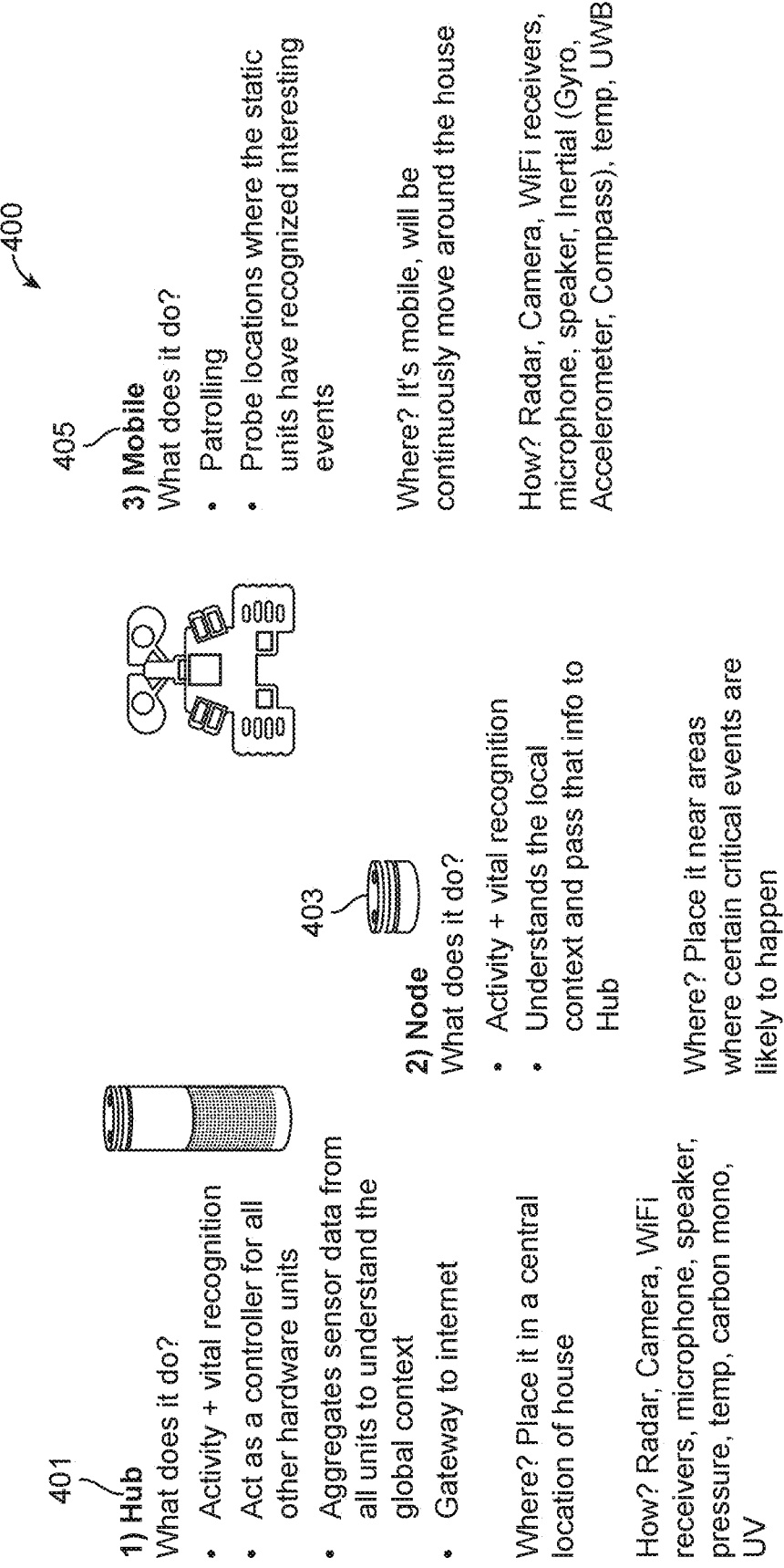
FIG. 4 is a detailed diagram of hardware apparatus according to an example of the present invention.

FIG. 4 is a detailed diagram 400 of hardware apparatus according to an example of the present invention. This diagram is merely an example, which should not unduly limit the scope of the claims herein. As shown, the hardware units include at least a hub device 401, node 403, and mobile node 405, each of which will be described in more detail below.

In an example, the hub includes various sensing devices. The sensing devices, include, among others, a radar, a WiFi, a Bluetooth, a Zigbee sniffer, a microphone and speakers, a smoke detector, a temperature detector, a humidity detector, a UV detector, a pressure detector, MEMS (e.g., accelerometer, gyroscope, and compass), a UWB sensors (for finding locations of all the deployed elements relative to each other), among others. In an example, the hub is a gateway to interne via WiFi, GSM, Ethernet, landline, or other technique. The hub also connects to other units (Mini Node /Mobile Node) via Bluetooth, WiFi, Zigbee, UWB and coordinates them with each other. In an example, certain data processing, such as noise removal, feature extraction to reduce amount of data uploaded to cloud is included. In an example, the hub alone can be sufficient to cover a small living space. In an example, the hub is deployed as a single device somewhere in a desirable location (e.g., middle of the living space) so that it has good connectivity to all other units. An example of such deployment is provided in the Figure below.

Figure 5:
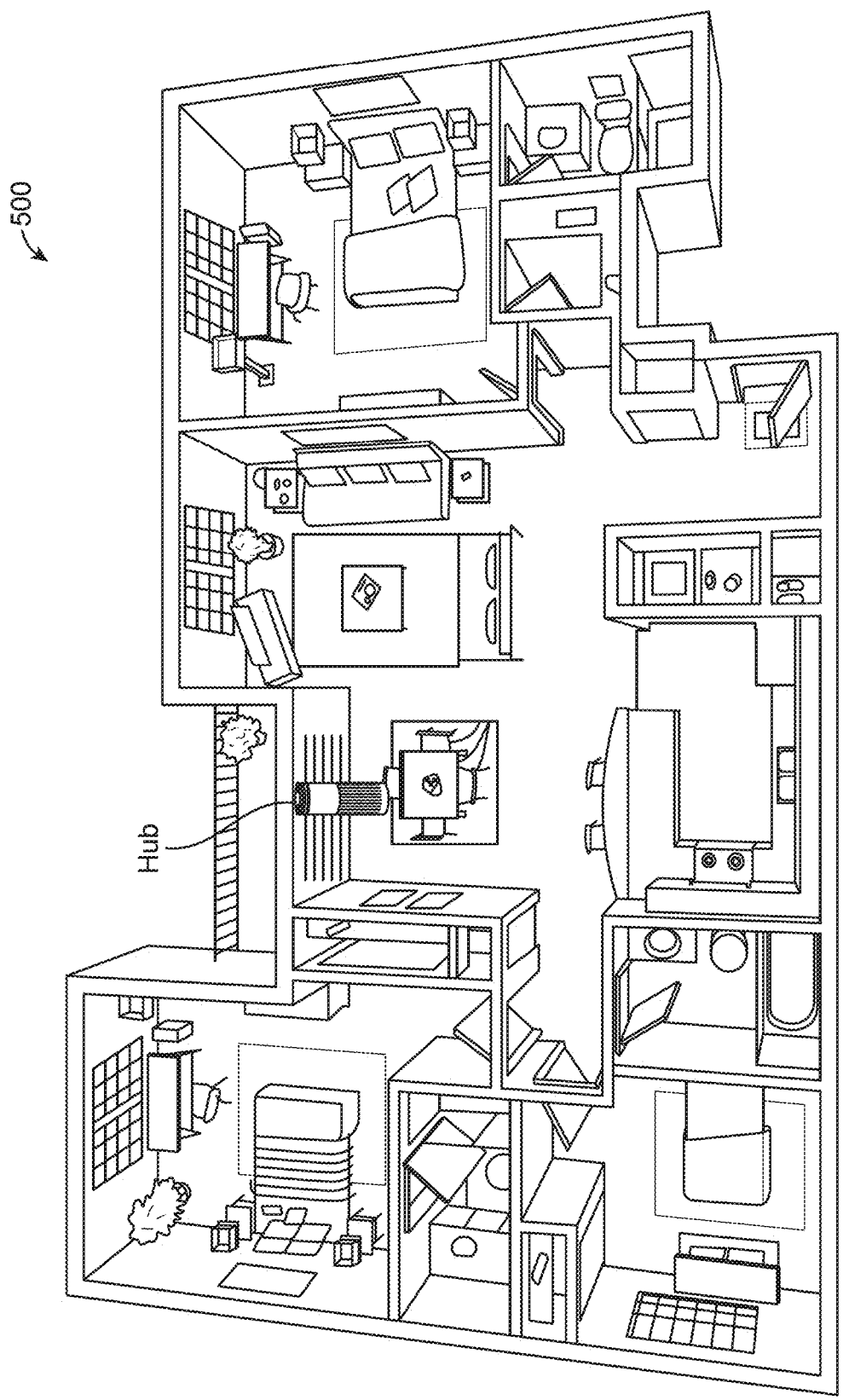
FIG. 5 is a simplified diagram of a hub in a spatial region according to an example of the present invention.

FIG. 5 is a simplified diagram 500 of a hub in a spatial region according to an example of the present invention. This diagram is merely an example, which should not unduly limit the scope of the claims herein. As shown, the hub is deployed in the middle of the living space in a house.

Figure 6:
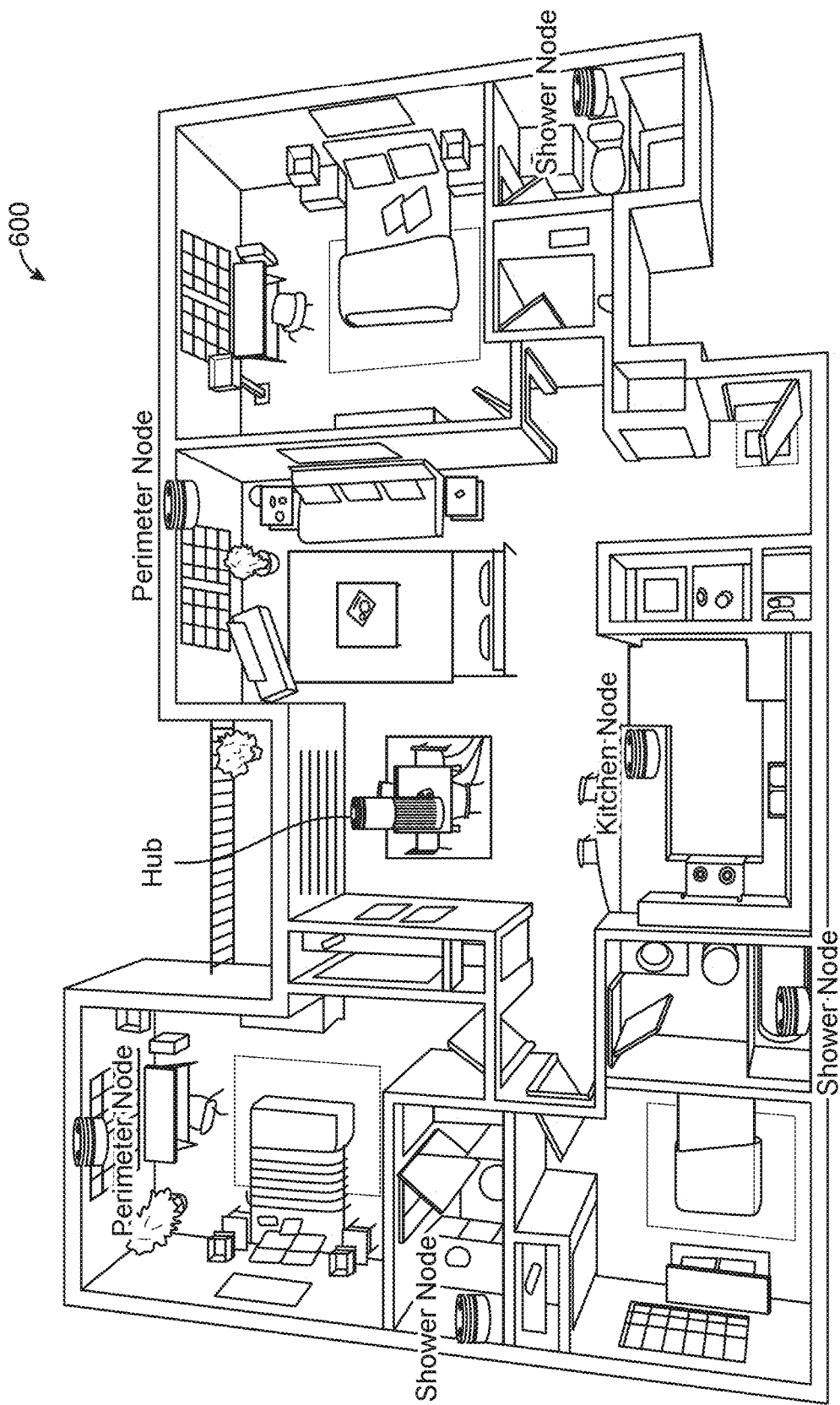
FIG. 6 is a simplified diagram of a mini mode in a spatial region according to an example of the present invention.

In an example, as shown in FIG. 6, the system 600 has sensors, which is a subset of sensors in the hub. The sensors are configured to in various spatial locations to improve coverage area and improve accuracy for detection of critical events (e.g., fall, someone calling for help). The sensors also communicate with the hub via WiFi, Bluetooth, ZigBee or UWB, or other technique. Additionally, the sensors or each mini node is deployed in a bathrooms, where chances of fall is high, a kitchen, where we can learn about eating habits by listening to sounds, RF waves, vibrations, or a perimeter of the living space, that will allow us to learn approximate map of the space under consideration, among other locations. Additionally, each of the mini nodes can save power and costs by adding more complexity on the hub. This can even enable us to operate on battery for extended periods. For example, each of the nodes can have only single antenna WiFi and hub could have multiple antennas, for WiFi based sensing. Additionally, each of the nodes use simpler radar (e.g., single antenna doppler) vs MIMO FMCW in the HUB. Additionally, each node can be configured with a single microphone whereas the hub can have array of microphone. Of course, there can be other variations, modifications, and alternatives. As shown, each node is configured in a kitchen, shower, perimeter, or other location.

Figure 7:
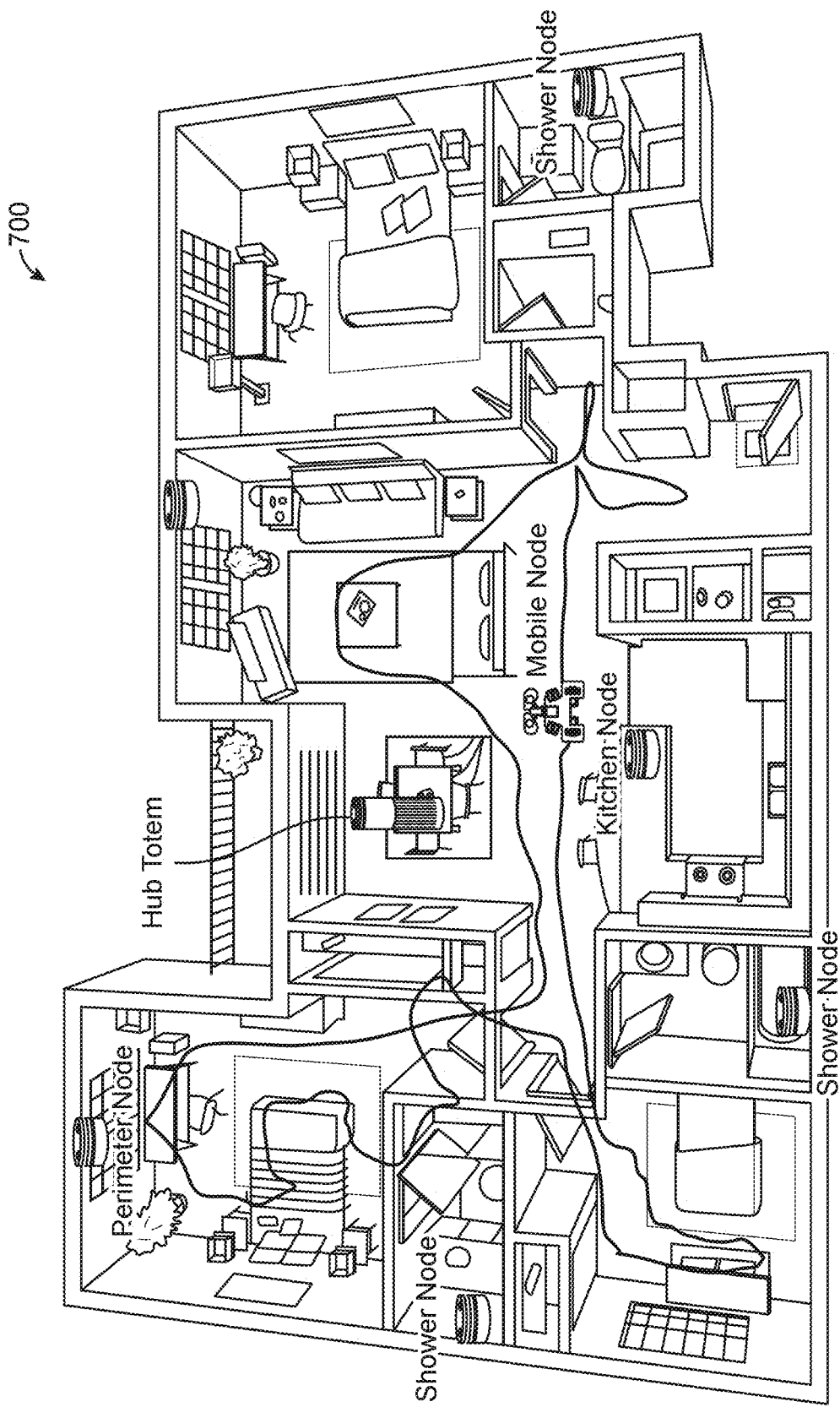
FIG. 7 is a simplified diagram of a mobile mode in a spatial region according to an example of the present invention.

FIG. 7 is a simplified diagram 700 of a mobile node according to an example of the present invention. This diagram is merely an example, which should not unduly limit the scope of the claims herein. In an example, each mobile node is a subset of sensors in the hub. The mobile node sensors include a camera such as RGB or IR. In an example, each of the nodes and hub collaboratively figure out interesting events, and pass that information to the mobile node. The technique then goes to the location and probes further. In an example, the camera can be useful to visually find what is going on in the location. In an example, freewill patrolling can be used to detect anything unusual or to refine details of the map created based on perimeter nodes. In an example, onboard UWB can enable precise localization of the mobile node, which can also enable wireless tomography, where the precise RGB and wireless map of the living space is determined. As shown, the mobile node, such as a mobile phone or smart phone or other movable device, can physically move throughout the spatial location. The mobile node can also be a drone or other device. Of course, there can be other variations, modifications, and alternatives. Further details of an example of a hub device can be found throughout the present specification and more particularly below.

Figure 8:
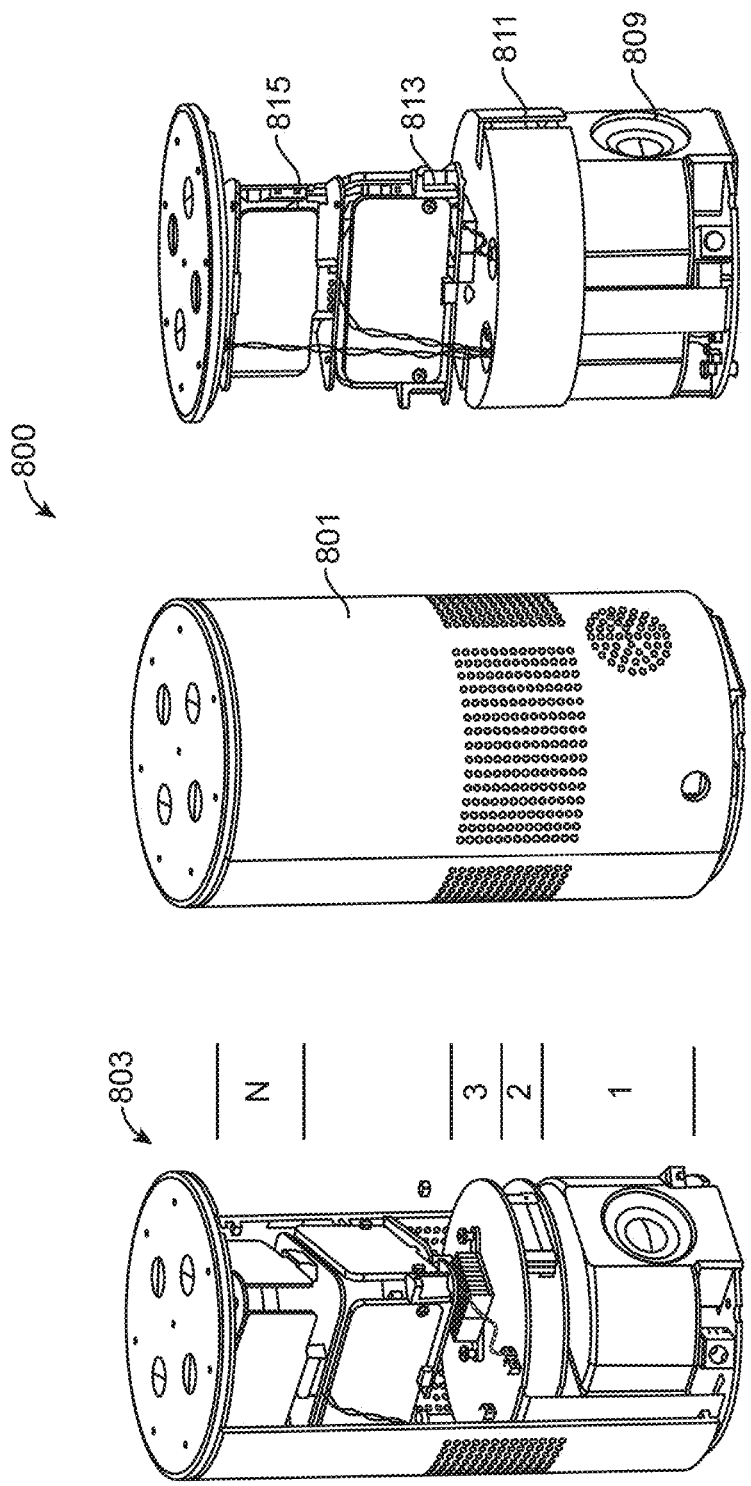
FIG. 8 is a simplified diagram of a hub device according to an example.

FIG. 8 is a simplified diagram of a hub device 800 according to an example of the present invention. As shown, the hub device has a cylindrical housing 801 having a length and a diameter. The housing has an upper top region and a lower bottom region in parallel arrangement to each other. In an example, the housing has a maximum length of six to twenty four inches and width of no longer than six inches, although there can be other lengths and widths, e.g., diameters. In an example, the housing has sufficient structural strength to stand upright and protect an interior region within the housing.

In an example, the housing has a height characterizing the housing from a bottom region to a top region. In an example, a plurality of levels 803 are within the housing numbered from 1 to N, wherein N is an integer greater than two, but can be three, four, five, six, seven, and others.

As shown, various elements are included. A speaker device 809 configured within the housing and over the bottom region, as shown. The hub device also has a compute module 811 comprising a processing device (e.g., microprocessor) over the speaker device. The device has an artificial intelligence module configured over the compute module, a ultra-wide band ("UWB") module 813 comprising an antenna array configured over the artificial intelligence module, and a frequency modulated continuous wave ("FMCW") module 815 with an antenna array configured over the UWC module. In an example, the FMCW module being configured to process electromagnetic radiation in a frequency range of 24 GHz to 24.25 GHz. In an example, the FMCW module outputs an FMCW signal using a transmitter, and receives back scattered signals using a receiver, such as a receiver antenna. The device has an audio module configured over the FMWC module and an inertial measurement unit ("IMU") module configured over the FMCW module. In an example, the audio module comprises a microphone array for detecting energy in a frequency range of sound for communication and for detecting a sound energy. In an example, the IMU module comprises at least one motion detection sensor consisting of one of a gyroscope, an accelerometer, a magnetic sensor, or other motion sensor, and combinations thereof.

As shown, the speaker device, the compute module, the artificial intelligence module, the UWB module, the FMCW module, the audio module, and the IMU module are arranged in a stacked configuration and configured, respectively, in the plurality of levels numbered from 1 to N. In an example, the speaker device comprises an audio output configured to be included in the housing. As shown, the speaker device is spatially configured to output energy within a 360 degree range from a midpoint of the device.

In an example, the compute module comprises a microprocessor based unit coupled to a bus. In an example, the compute module comprises a signal processing core, a microprocessor core for an operating system, a synchronizing processing core configured to time stamp, and synchronize incoming information from each of the FMCW module, IMU module, and UWB module.

In an example, the device further comprises a real time processing unit configured to control the FMCW switch or the UWB switch or other switch requiring a real time switching operation of less than ½ milliseconds of receiving feedback from a plurality of sensors.

In an example, the device has a graphical processing unit configured to process information from the artificial intelligence module. In an example, the artificial intelligence module comprises an artificial intelligence inference accelerator configured to apply a trained module using a neural net based process. In an example, the neural net based process comprises a plurality of nodes numbered form 1 through N. Further details of the UWB module can be found throughout the specification and more particularly below.

Figure 9:
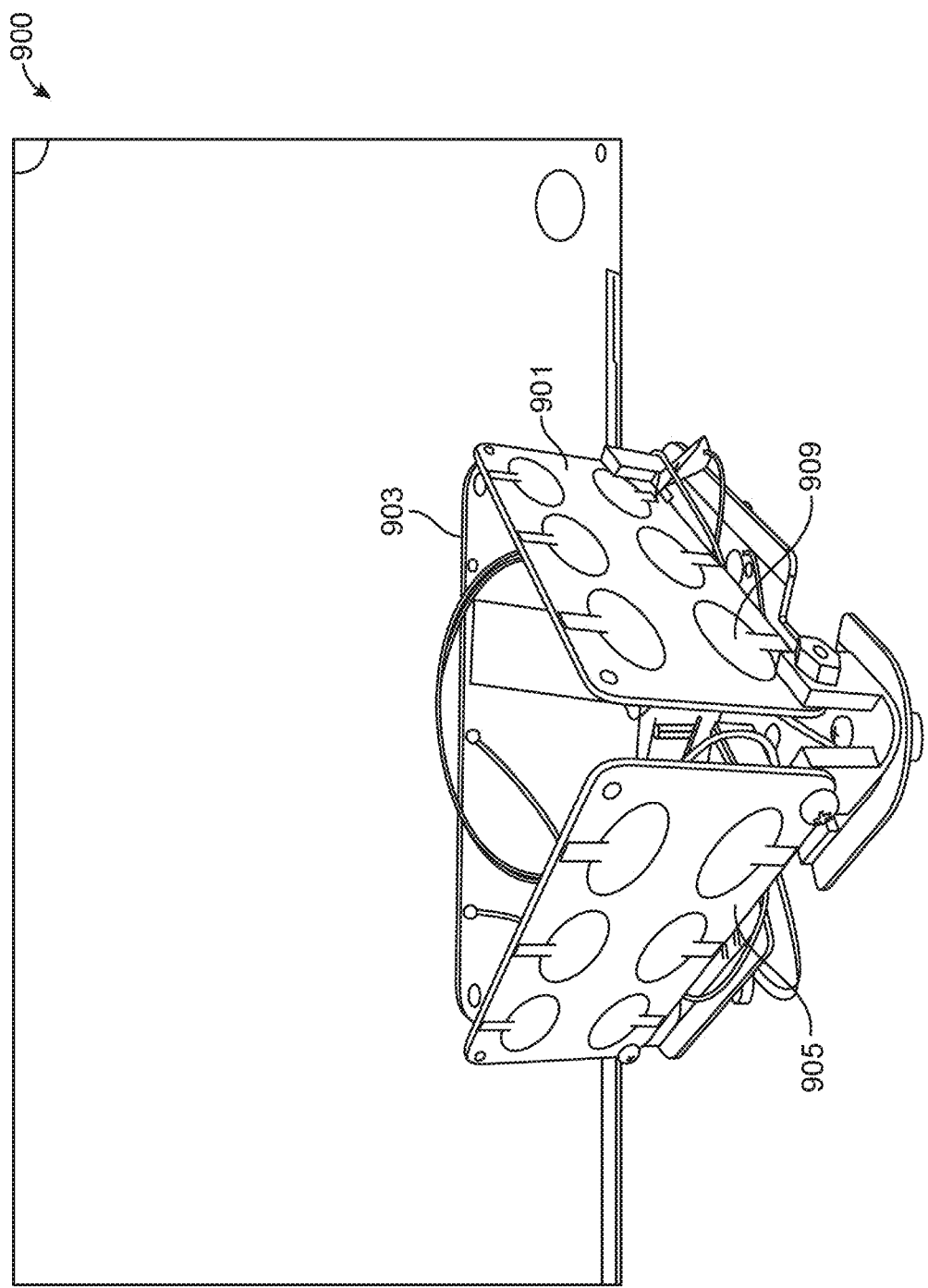
FIG. 9 is a simplified diagram of an ultra-wide band module for the hub according to an example of the present invention.

FIG. 9 is a simplified diagram of an ultra-wide band module 900 for the hub according to an example of the present invention. As shown is ultra-wide band rf sensing apparatus or module. In an example, the apparatus has at least three antenna arrays 901, 903, 905 configured to sense a back scatter of electromagnetic energy from spatial location of a zero degree location in relation to a mid-point of the device through a 360 degrees range where each antenna array is configured to sense a 120 degree range. As shown, each of the three antenna arrays comprises a support member, a plurality of transmitting antenna 909 spatially configured on a first portion of the support member. The support member also has a transmitting integrated circuit coupled to each of the plurality of transmitting antenna and configured to transmit an outgoing UWC signal. Each of the antenna array also has a plurality of receiving antenna spatially configured on second portion of the support member. The support member also has a receiving integrated circuit coupled to each of the plurality of receiving antenna and configured to receive an incoming UWB signal and configured to convert the UWC signal into a base band.

In an example, the device has a triangular configuration comprising a first antenna array, a second antenna array, and a third antenna array included in the at least three antenna arrays. The three arrays provide a 360 degree visibility range as measured from a horizontal plane, and a 80 degree visibility range as measured from a vertical plane normal to the horizontal plane. As previously noted, the three arrays are enclosed in a housing that provides mechanical support. In an example, each of the sensor arrays is provided on a substrate member to be configured in the triangular configuration. The substrate member has a face arranged in a normal manner in a direction to each of the support members.

In an example, the UWB module can operate at a center frequency of 7.29 GHz and a bandwidth of ~1.5 GHz with multiple antenna arrays to achieve the FCC/ETSI compliance standard. In an example, the module has a combined horizontal field-of-view of 360 degrees about a center point of the module. In an example, the module has a range greater than 10 meters, but can be shorter and longer. In an example, the module is configured to achieve a transmission and a receive rate of frames per second (FPS) equal to or greater than 330 per Tx-Rx. In an example, the module has a combined horizontal field of view of 360 degrees achieved using three (3) antenna arrays, each of which covering 120 degrees. In an example, each antenna array comprises of 1-TX and 4-RX. Each antenna array is configured to complete the acquisition of a frame within 1 millisecond or less. Accordingly, a total of three (3) milliseconds covers all three (3) sectors, achieving a frame rate of 330 fps per sector (per Tx-Rx) in an example. In an example, the module has programmability of various parameters similar to Novelda X4M03 module. In an example, the module is a hybrid architecture that has four by four radar integrated circuit devices in MIMO configuration that switches between the three antenna arrays. The configuration is capable of simultaneous capturing of all four Rx frames in an antenna array. Further details of the present UWB module is provided throughout the present specification and more particularly below.

FIG. 10 is a simplified diagram 1000 of electrical parameters according to an example for the ultra-wide band module. In an example, various parameters are as listed in the table. Each of the parameters listed are suggested and can be adjusted to minimize cost and complexity, while still achieving performance. In an example, the module has a data transfer of 3.2 MBps (e.g., 330 fps×200 frame length×2 bytes×2×4 receivers×3 modules. In an example, the module can include a micro controller unit to communicate with X4 SoC through an SPI interface. In an example, a central processing unit communicates with a compute module through a serial interface such as a universal serial bus, i.e., USB. The micro controller is configured on a board with sufficient memory to store raw data. In an example, the memory has a capacity of greater than 128 MB such as a 128 MB SDRAM. Further details of the electrical parameters configured within a system diagram are provided below.

Figure 11:
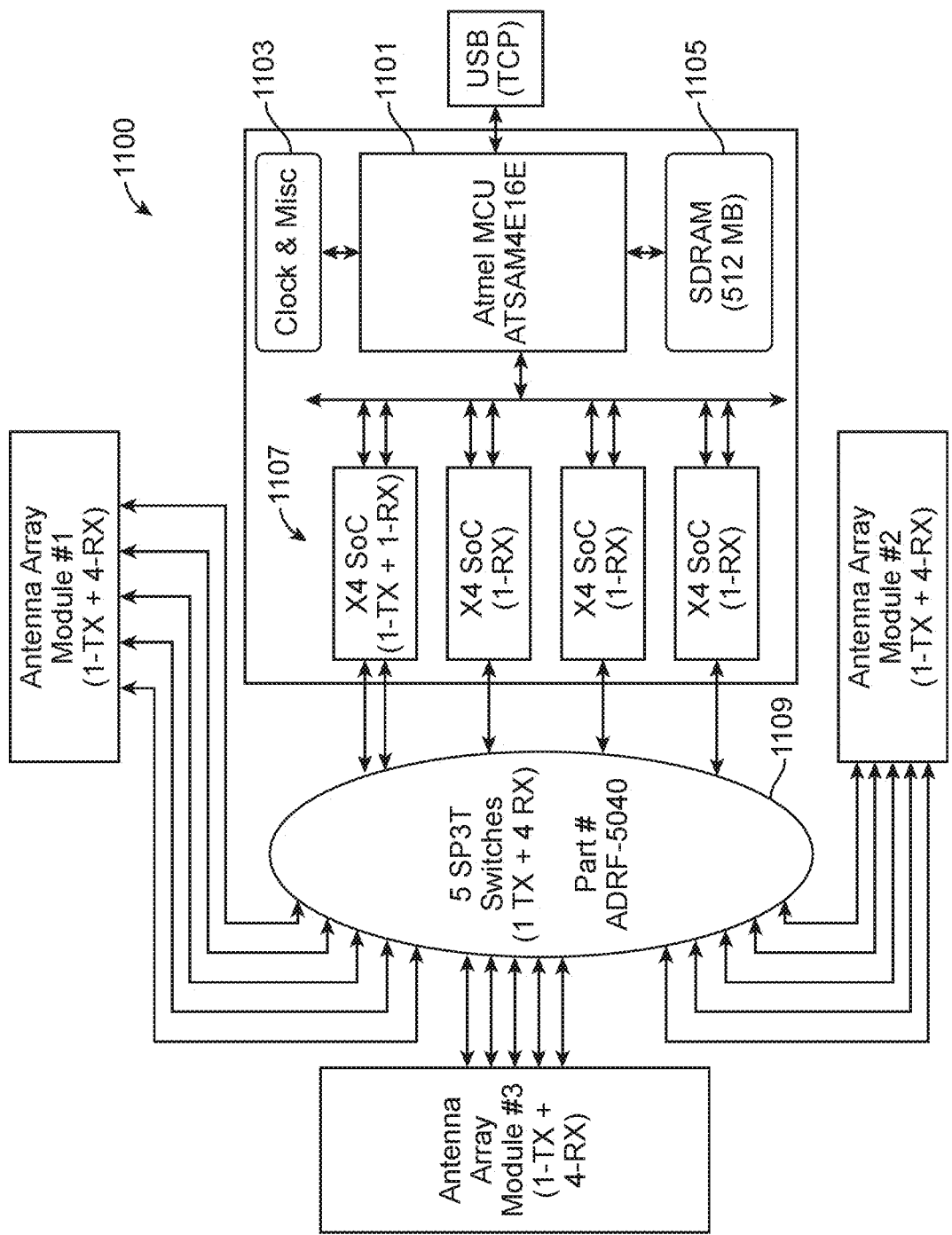
FIG. 11 is a simplified system diagram of the ultra-wide band module according to an example of the present invention.

FIG. 11 is a simplified system diagram 1100 of the ultra-wide band module according to an example of the present invention. As shown, the system has a micro controller 1101, such as an integrated circuit known as ATSAM4E16E by Microchip Technology Inc. of 2355 West Chandler Blvd., Chandler, Arizona, USA 85224-6199. The micro controller has a serial interface, such as the universal serial interface, USB. The controller is coupled to random access memory 1105 for storing raw data, and a clock and other miscellaneous circuits 1103. In an example, the output of the controller communicates 1107 with four XETHRU X4 SoCs manufactured by Novelda AS of Norway.

In an example, the basic components of the X4 SoC are a transmitter, a receiver, and related control circuits. The system is controlled by a system controller and is configurable through a 4(6)-wire serial peripheral interface (SPI). In an example, the X4 receive path (RX) consists of a low noise amplifier (LNA), a digital-to-analog converter (DAC), 1536 parallel digital integrators as well as an output memory buffer, accessible through the SPI. The RX is tightly integrated with the transmitter (TX) and is designed for coherent integration of the received energy. The X4 transmit path (TX) consists of a pulse generator capable of generating pulses at a rate of up to 60.75 MHz. The output frequency and bandwidth are designed to fit worldwide regulatory requirements. The radar transceiver is able to operate completely autonomously and can be programmed to capture data at predefined intervals and then alert or wake up a host MCU or DSP through dedicated interrupt pins. A power management unit controls the on-chip voltage regulators and enables low-power applications to use efficient duty cycling by powering down parts of the circuit when they are not needed. The system can be configured to consume less than 1 mW in idle mode when all analog front end components are turned off. As shown, each of the four X4 SoCs is coupled in parallel to a switch.

In an example, the switch 1109 is coupled to each antenna array as shown. In an example, the switch can be one listed under HMC241/HMC7992/ADRF5040 SP4T RF Switches of Analog Devices, Inc. The switches are non-reflective RF switches from DC to 12 GHz for 4G cellular, milcom, and radio applications. Examples of HMC241, HMC7992, and ADF5040 are radio frequency (RF) nonreflective/absorptive single pull, quad throw (SP4T) switches that can interface with 3.3 V, TTL, LVTTL, CMOS, and LVCMOS logic. The switches operate from DC to 12 GHz frequency range. The HMC241 is a GaAs MMIC RF switch that operates in the DC to 4 GHz range. The switch takes a single supply at +5 V. The HMC7992 has a 100 MHz to 6 GHz frequency range. The ESD rating is for this switch 2 kV (HBM) class 2. The HMC7992 takes a single voltage supply from ±3.3 V to +5 V. The ADRF5040 comes in a small 4 mm×4 mm LFCSP package and requires a dual ±3.3 V supply. The switch operates in the 9 kHz to 12 GHz range. The ADRF5040 has the added benefit of being 4 kV (HBM) ESD rating. HMC241, HMC7992, and ADF5040 are ideal for 4G cellular infrastructure such as base stations and repeaters as well as military communications and industrial test and measurement applications. Of course, there can be other variations, modifications, and alternatives.

In an example, the UWC module comprises a switch configured between a plurality of UWC transceivers. The switch is configured to select one of the three antenna arrays to sense the back scatters while the other two antenna arrays are turned off. In an example, the switch is an rf switch such as the one listed under part number ADRF-5040 manufactured by Analog Devices, Inc. In an example, the UWC module also has a controller configured to control the switch and the three antenna array. In an example, the controller cycles through a predetermined process to decide which one of the three antenna array to activate while the other two antenna arrays are turned off.

In an example, the at least three antenna array are configured to sense electromagnetic energy ranging from 6 to 8 GHz in frequency. As noted, the sensing apparatus is spatially positioned within a center of a geographic location of a room to detect movement of human user.

In an example, the present invention provides a method processing an electromagnetic signal generated from an ultra wide band rf signal to detect an activity of a human user. Referring to FIG. 11, the method includes generating a base band outgoing UWC signal from a transmitting integrated circuit, which is coupled to a micro controller device. The method includes transferring and then receiving the base band outgoing UWC signal at a switch device, which is coupled to the micro controller. The switch is configured to direct the outgoing UWC signal using the switch device to one of three antenna arrays. In an example, the three antenna array have been configured in a triangular configuration to transmit the outgoing UWC signal from spatial location of a zero degree location in relation to a midpoint of the device through a 360 degrees visibility range where each antenna array is configured to sense a 120 degree range in a horizontal plane. Each of the antenna array is configured to sense and transmit at least an 80 degree visibility range as measured from a vertical plane that is normal to the horizontal plane. In an example, each of the three antenna arrays comprise a support member, a plurality of transmitting antenna spatially configured on a first portion of the support member, a transmitting integrated circuit coupled to each of the plurality of transmitting antenna and configured to transmit the outgoing UWC signal. Each of the antenna array also has a plurality of receiving antenna spatially configured on second portion of the support member. The antenna array also has a receiving integrated circuit coupled to each of the plurality of receiving antenna and configured to receive an incoming UWB signal and configured to convert the UWC signal into a base band. In an example, the method also receives a back scattered electromagnetic signal caused by an activity of a human user redirecting the outgoing UWB signal. In an example, the received signals are processed, using the artificial intelligence module to form an output. Of course, there can be other variations, modifications, and alternatives.

Figure 12:
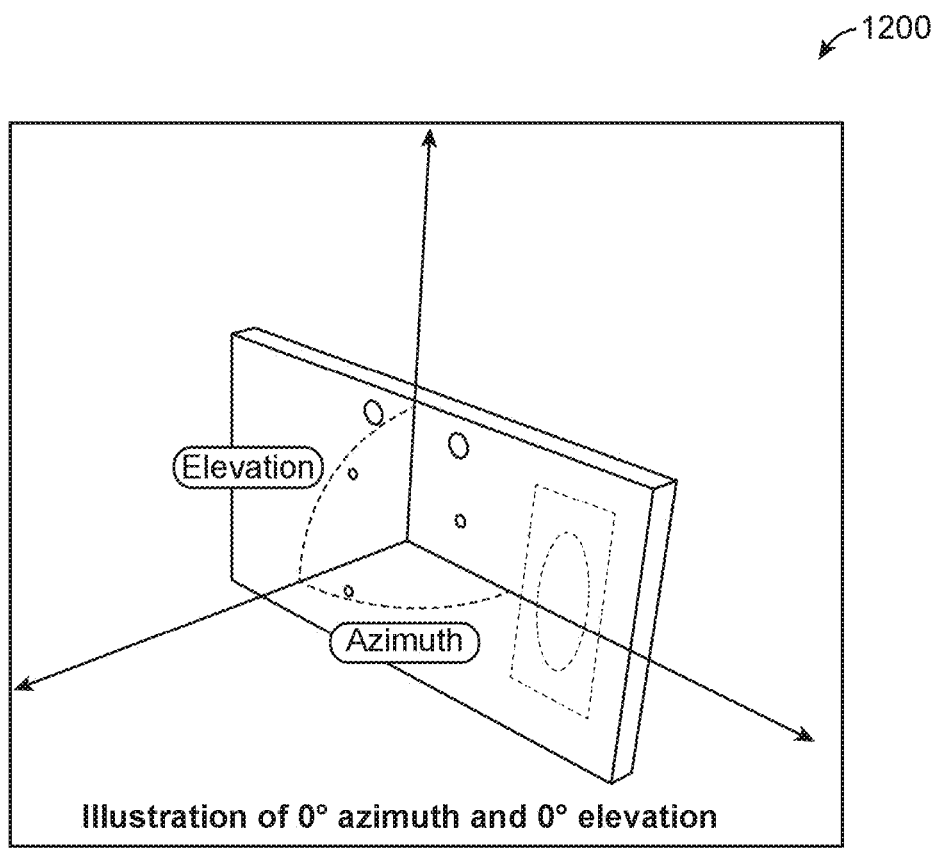
FIG. 12 is an example of antenna array parameters for the ultra-wide band module according to the present invention.

FIG. 12 is an example 1200 of antenna array parameters for the ultra-wide band module according to the present invention. As shown, each antenna array has one 1-Tx and four 4-Rx. Each Tx/Rx is designed to cover 120 degree azimuth field of view and maximize elevation field of view as desirable. In an example, serial fed patch antennas can be used. In an example, the antennas are fabrication using material such as a Rogers 4350 substrate. In an example, the antennas can be an integrated WiFi filter, if desired, optimized for frequencies between 6.0 and 8.5 GHz. In an example, the antenna is designed for FCC/ETSI Compliant for TX Center frequency. Of course, there can be other variations, modifications, and alternatives.

Figure 13:
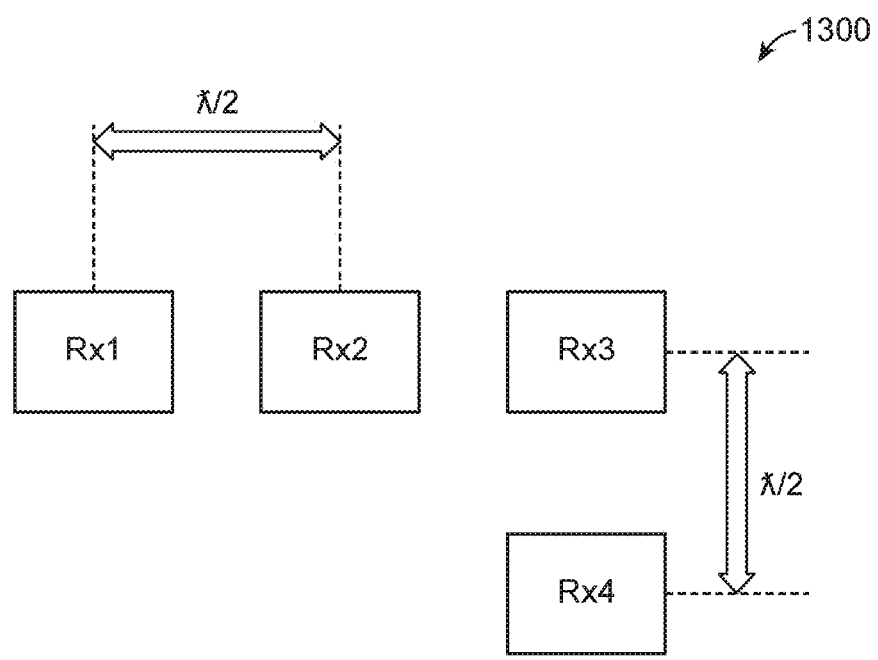
FIG. 13 is an example of antenna array configuration for the ultra-wide band module according to the present invention.

FIG. 13 is an example of antenna array configuration 1300 for the ultra-wide band module according to the present invention. As shown, the antenna array is spatially provided on a support member, such as a board. The antenna array comprises four (4) Rx in an antenna array that are in a two-dimensional (2D) configuration as shown. The Rx4 is aligned with Rx1, Rx2 or Rx3, and separated by lambda over two, as shown. Each of the antennas is separated by lambda over two, as shown. Of course, there can be other variations, modifications, and alternatives.

In an example, the present invention provides a method processing an electromagnetic signal generated from an ultra wide band rf signal to detect an activity of a human user. In an example, the method includes generating a base band outgoing UWC signal. The method also includes receiving the base band outgoing UWC signal at a switch device and directing the outgoing UWC signal using the switch device to one of three antenna arrays configured in a triangular configuration to transmit the outgoing UWC signal from spatial location of a zero degree location in relation to a midpoint of the device through a 360 degrees visibility range where each antenna array is configured to sense a 120 degree range in a horizontal plane. Each of the antenna array is configured to sense and transmit at least an 80 degree visibility range as measured from a vertical plane that is normal to the horizontal plane.

In an example, each of the three antenna arrays has a support member, e.g., board, printed circuit board. In an example, each array has a plurality of transmitting antenna spatially configured on a first portion of the support member, a transmitting integrated circuit coupled to each of the plurality of transmitting antenna and configured to transmit the outgoing UWC signal, a plurality of receiving antenna spatially configured on second portion of the support member, and a receiving integrated circuit coupled to each of the plurality of receiving antenna and configured to receive an incoming UWB signal and configured to convert the UWC signal into a base band signal. In an example, the method includes receiving a back scattered electromagnetic signal caused by an activity of a human user redirecting the outgoing UWB signal.

The apparatus of claim 11 wherein the UWB module comprises a micro controller unit coupled to a memory resource, and a clock circuit, the micro controller unit being configured with a universal serial bus interface coupled to the compute module; wherein the compute module is configured with the artificial intelligence module to process information from the back scattered electromagnetic signal from the base band signal to detect the activity of the human entity.

In an example, the support member comprises a major plane positioned normal to a direction of gravity.

In an example, the antenna array comprises at least three antenna array spatially arranged in a triangular configuration comprising a first antenna array, a second antenna array, and a third antenna array included in the at least three antenna arrays to provide a 360 degree visibility range as measured from a horizontal plane, and a 80 degree visibility range as measured from a vertical plane normal to the horizontal plane. In an example, the antenna array comprises at least three antenna array spatially arranged in a triangular configuration comprising a first antenna array, a second antenna array, and a third antenna array included in the at least three antenna arrays to provide a 360 degree visibility range as measured from a horizontal plane, and a 80 degree visibility range as measured from a vertical plane normal to the horizontal plane, and further comprising a controller configured to control a switch coupled with each of the three antenna array, the controller cycles through a predetermined process to decide which one of the three antenna array to activate while the other two antenna arrays are turned off.

In an example, each antenna array comprises 1-TX and 4-RX.

In an example, the system has a switch device coupled between each of the antenna array and four receive lanes each of which is coupled to the receiving integrated circuit device, one transmit lane coupled to a transmitting integrated circuit device, and a micro controller unit coupled to a bus coupled to the receiving integrated circuit device and the transmitting integrated circuit device, the micro controller unit coupled to a memory resource configured with the micro controller to store raw data from information derived from four receive lanes, the micro controller unit being coupled to a clock.

In an example, each antenna array comprises 1 TX and four RX. In an example, the system has a switch device coupled between each of the three antenna arrays and four receive lanes each of which is coupled to the receiving integrated circuit device, one transmit lane coupled to a transmitting integrated circuit device, and a micro controller unit coupled to a bus coupled to the receiving integrated circuit device and the transmitting integrated circuit device, the micro controller unit coupled to a memory resource configured with the micro controller to store raw data from information derived from four receive lanes, the micro controller unit being coupled to a clock.

Figure 14:
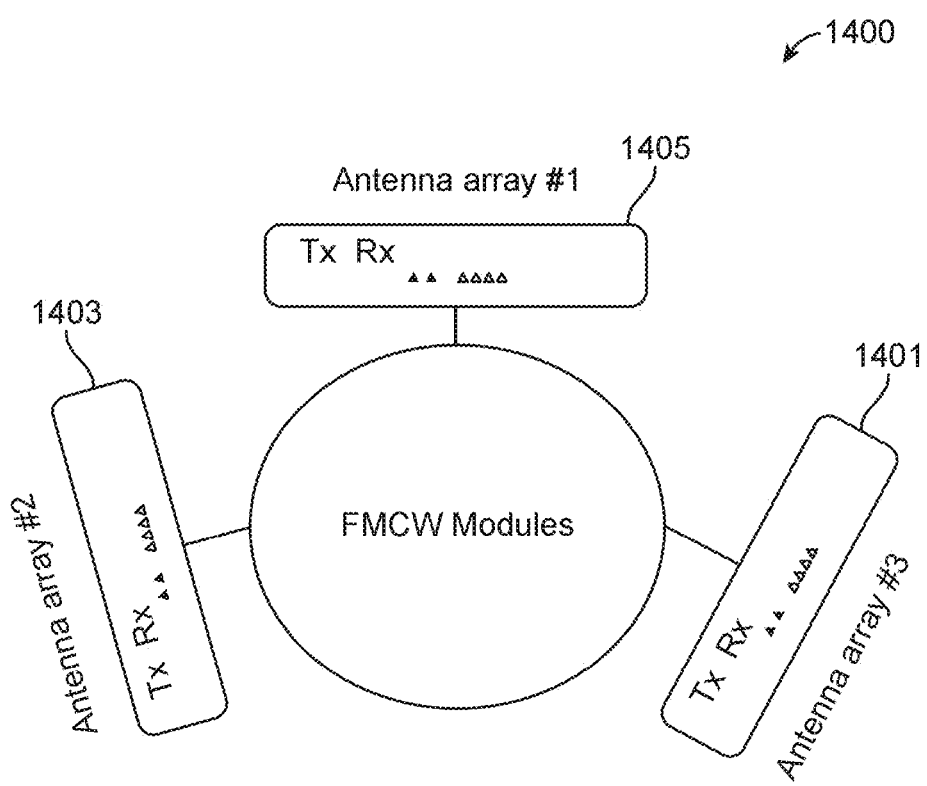
FIG. 14 is a simplified diagram of FMCW modules and antenna arrays according to examples of the present invention.

In an example, the present techniques include a method, apparatus, and device for processing signals. As shown 1400 in FIG. 14, the present FMCW device operates at 24 GHz ISM band with multiple antenna arrays 1401, 1403, 1405. In an example, the device has various capabilities, such as a combined horizontal field-of-view of 360 degrees, a range of ≥12 meters, a FPS equal to or greater than 1000 per Tx-Rx, programmability of various parameters, among other elements. In an example, each of the antenna array including TX and RX communicates to FMCW modules, as shown. The three antenna array are arranged in a triangular configuration, each of which has a viewing range of 120 Degrees.

Figure 15:
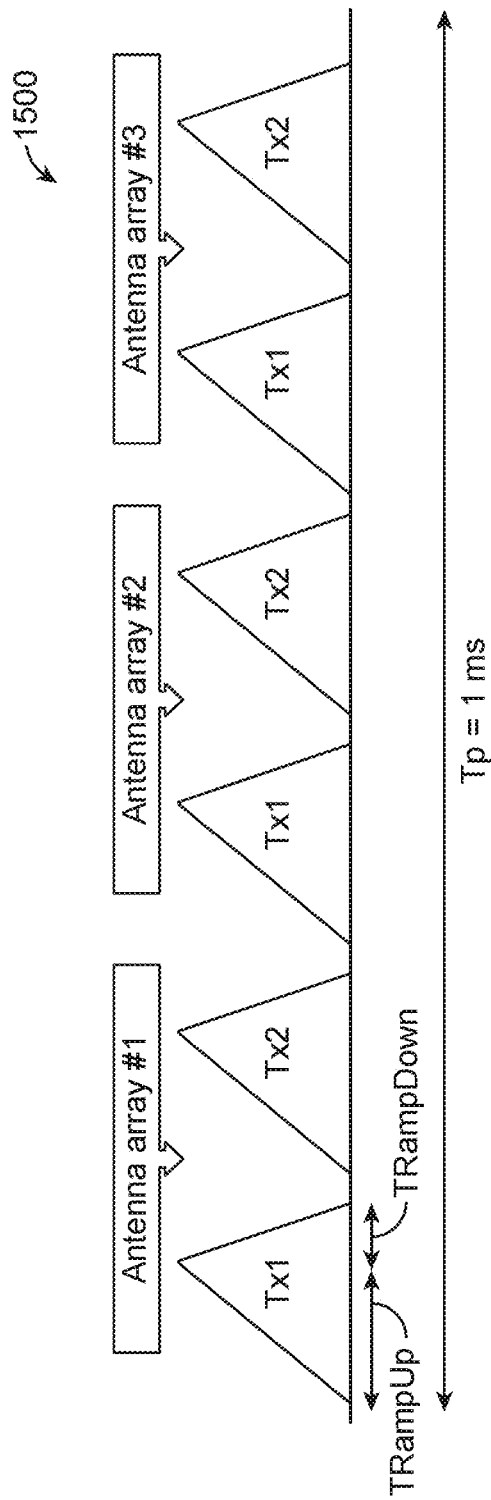
FIG. 15 is a simplified illustration of three antenna arrays according to examples of the present invention.

Referring now to FIG. 15, the device 1500 has various elements, such as antenna array 1, antenna array 2, and antenna array 3. In an example, the device has a 360 degree horizontal field-of-view to be achieved using three sets of antenna arrays, each covering 120 degrees (as wide vertical field-of-view as possible). In an example, each antenna array consists of 2 TX and 4 RX. In an example, the device has an fps of 1000 per TX-RX is achieved by generating 6 chirps for the 6 TX sequentially within 1 milliseconds. Of course, there can be other variations, modifications, and alternatives.

As shown in the Table in FIG. 16, various device parameters are described. In an example, the parameters listed are suggested and can be modified or replaced to minimize cost and complexity, while achieving desired performance. In an example, sampled radar data are accessed via USB interface by a compute module, which is part of the overall system. In an example, the device has a data transfer rate of 6.14 MBps (e.g., 1000 fps×128 samples/frame×2 bytes×8 antenna×3 modules.) In an example, the device has a microcontroller, such as a one from Cypress Semiconductor, including a memory resource to store raw radar data. In an example, the device has a memory that has a capacity of 2 gigabits or greater. In an example, multiple configurations are described throughout the present specification and more particularly below.

Figure 17:
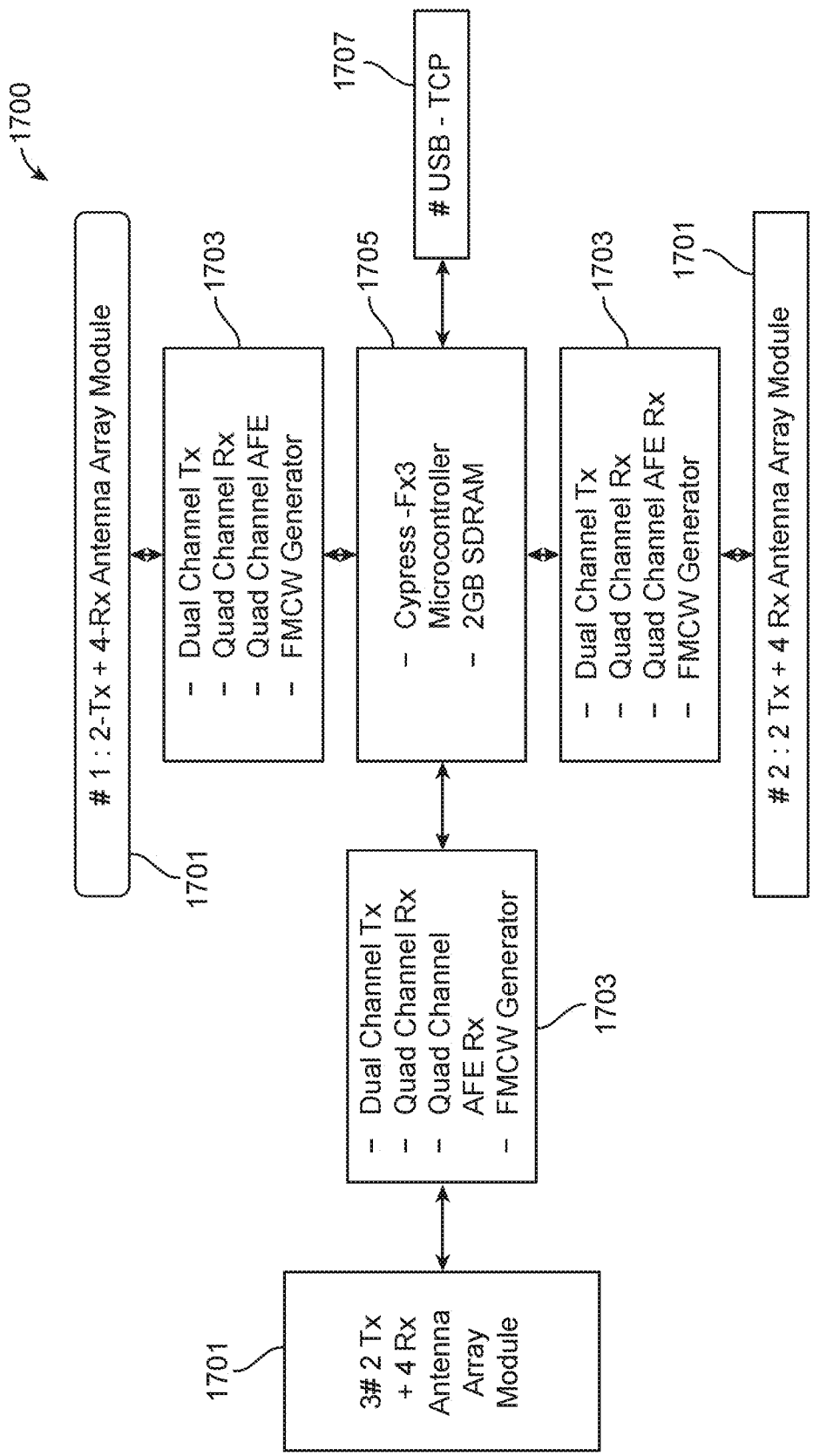
FIG. 17 is a simplified diagram of a system architecture for an FMCW device according to an example of the present invention.

In an example, FIG. 17 illustrates a simplified diagram 1700 of a system architecture for the FMCW device according to an example of the present invention. In an example, the present system has three antenna array 1701 each of which has 2-TX plus 4-RX (i.e., 8 virtual array). Each antenna array is coupled to a dual channel TX, quad channel RX, quad channel AFE RX, and FMCW frequency generator 1703. In an example, the system has a radio frequency (RF) module including a dual channel TX under part number ADF5901 by Analog Devices, Inc. In an example, the system has a quad channel RX listed under part number ADF5904 by Analog Devices. The system also has a quad channel AFE RX listed under part number ADAR7251 by Analog Devices. Additionally, the system has a FMCW generator listed under ADF4159 by Analog Devices. The system has a microcontroller 1705 listed under part number Cypress Microcontroller CYYSB301X, which is coupled to system memory, such as 2 GB—SDRAM, a SPI interface control between RF module and microcontroller. The system also has the microcontroller connected to TCP via a universal serial bus, USB 1707. Of course, there can be other variations, modifications, and alternatives.

Figure 18:
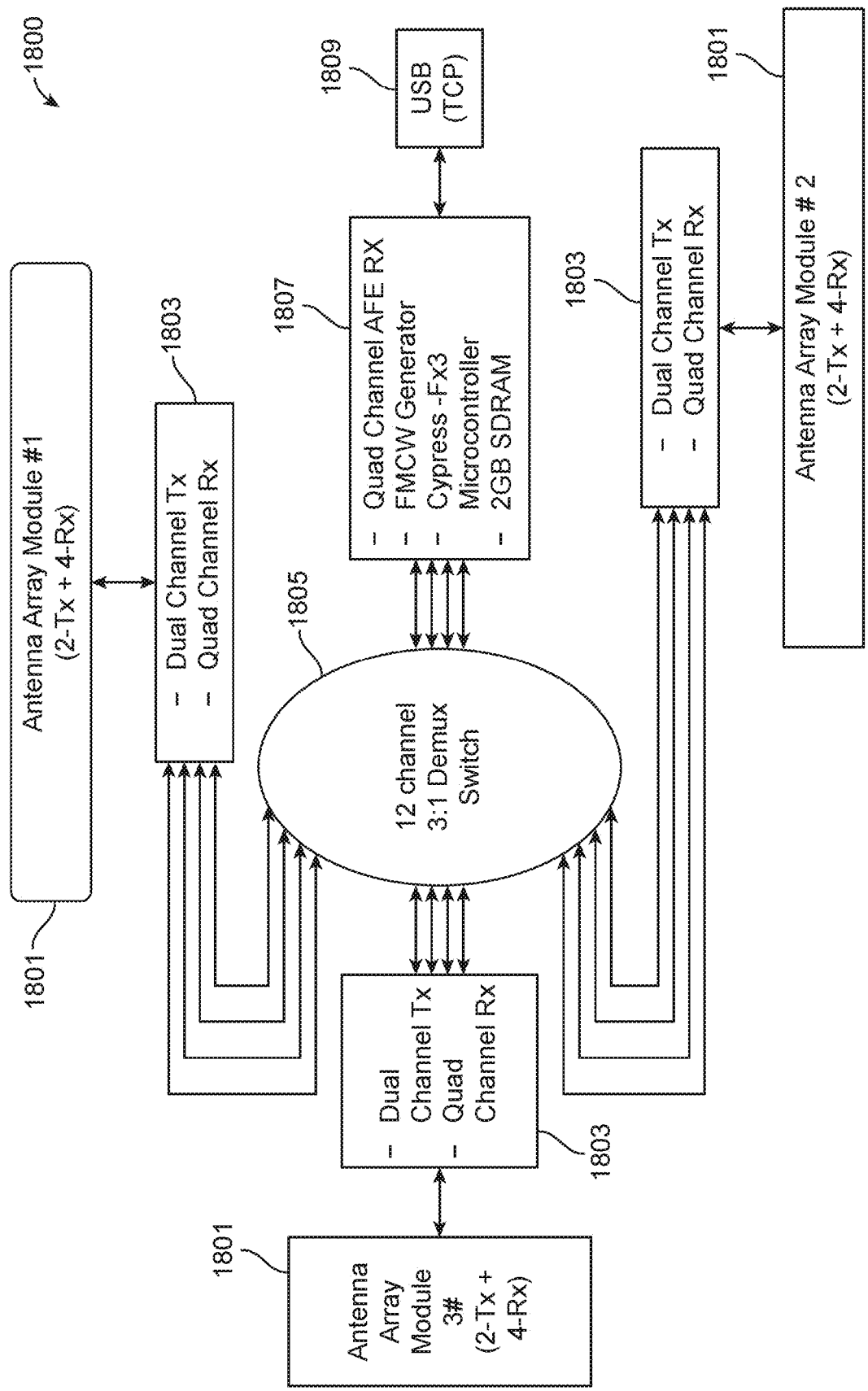
FIG. 18 is a simplified diagram of an alternative system architecture for an FMCW device according to an example of the present invention.

In an example, FIG. 18 illustrates a simplified diagram 1800 of a system architecture for the FMCW device according to an example of the present invention. In an example, the system has three antenna arrays 1801, each of which has 2-TX+4-RX (i.e., 8 virtual array). In an example, the system has an radio frequency module, RF module 1803. The RF module has a dual channel TX listed under part number ADF5901 by Analog Devices, Inc. The module has a quad channel RX listed under ADF5904 by Analog Devices.

In an example, the system has a processing and acquisition module 1807. The module has a quad channel AFE RX listed under ADAR7251 by Analog Devices, and a FMCW generator listed under ADF4159. The module is coupled to and communicates with a 12 channel—3:1 demux switches 1805 listed under TS3DV621 by Texas Instruments Incorporated. The system has a microcontroller such as a Cypress Microcontroller listed under part number CYYSB301X, which is coupled to a memory resource, such as a 2 GB SDRAM. The system has a SPI Interface control between RF module and microcontroller. A USB interface is coupled to TCP 1809. Of course, there can be other variations, modifications, and alternatives. Further details can be found in a more detailed diagram 1850 of FIG. 18A, as described below.

Figure 18A:
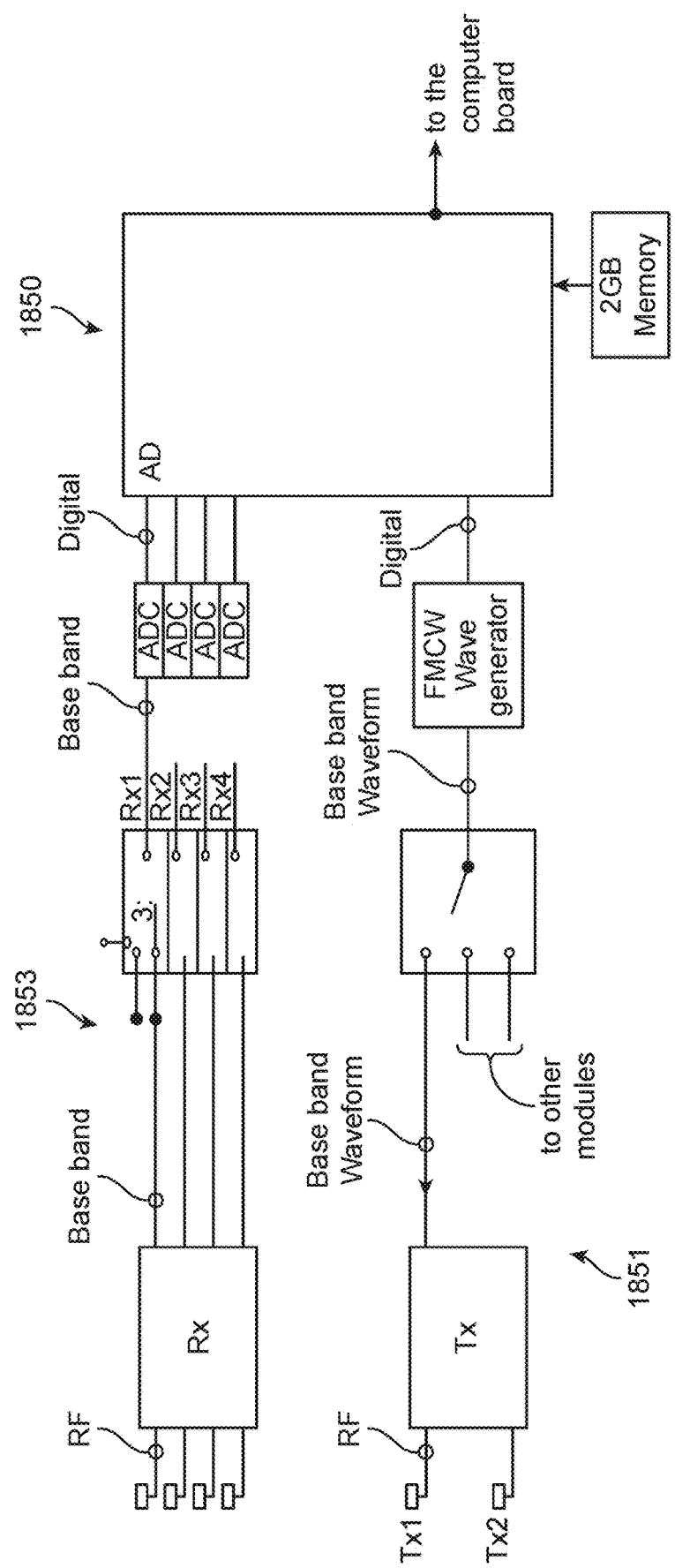
FIG. 18A is a simplified diagram of various elements in a micro controller module according to an example of the present invention.

In an example on a transmit lane 1851 referring to FIG. 18A, the microcontroller is coupled to a wave form generator to output a digital signal (e.g., in a register programming) that is converted in an analog to digital converter to a base band analog signal, which is fed to the switch. The switch is an analog switch that selects between one of the three arrays. The base band analog in transmitted to an RF integrated circuit that configures the base band analog into the FMCW rf signal to be transmitted via the TX antenna.

In an example on a receive lane 1853, four FMCW signals are received from four RX antenna. The four signals are received in parallel, and fed to and processed in the Rf integrated circuit to output corresponding four base band analog signals, each of which is fed to the switch. The switch allows signals from one of the three antenna array to be transferred to corresponding analog to digital converters, each of which are in parallel. Each analog to digital converter is coupled to the microcontroller. Each analog to digital converter configures incoming base band signal into digital, which is fed to the microcontroller. Of course, there can be other variations, modifications, and alternatives.

Figure 19:
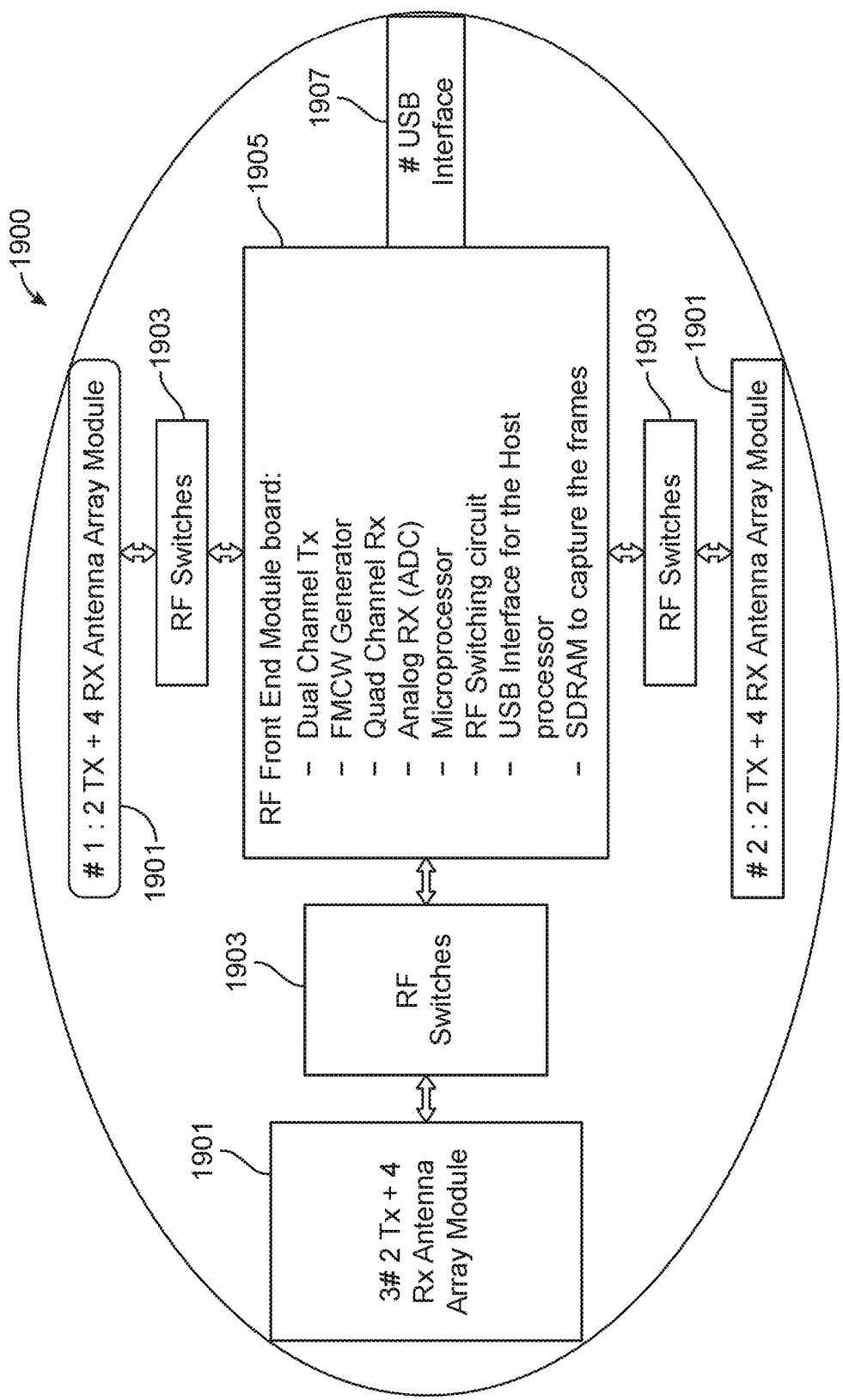
FIG. 19 is a simplified diagram of an alternative system architecture for an FMCW device according to an example of the present invention.

In an example, FIG. 19 illustrates a simplified diagram 1900 of a system architecture for the FMCW device according to an example of the present invention. The system has three antenna arrays 1901, each of which has 2-TX+4-RX (i.e., 8 virtual array). The system has an RF switch 1903 to switch between any one of the antenna arrays. In an example the system has an rf module and acquisition module 1905. The RF module and the acquisition module has a dual channel TX listed under ADF5901 by Analog Devices. The module has a quad channel RX listed under ADF5904 by Analog Devices, a quad Channel AFE RX listed under ADAR7251 by Analog Devices, and a FMCW generator listed under ADF4159 by Analog Devices. The module has a microcontroller such as the Cypress Microcontroller listed under CYYSB301X by Cypress Semiconductor, Inc. The microcontroller is coupled to a memory resource such as a 2 GB—SDRAM device. The system also has an interface such as a SPI Interface control 1907 between RF module and Cypress microcontroller. The system also has a serial interface such as the USB interface to connect to TCP. Of course, there can be other variations, modifications, and alternatives.

Figure 20:
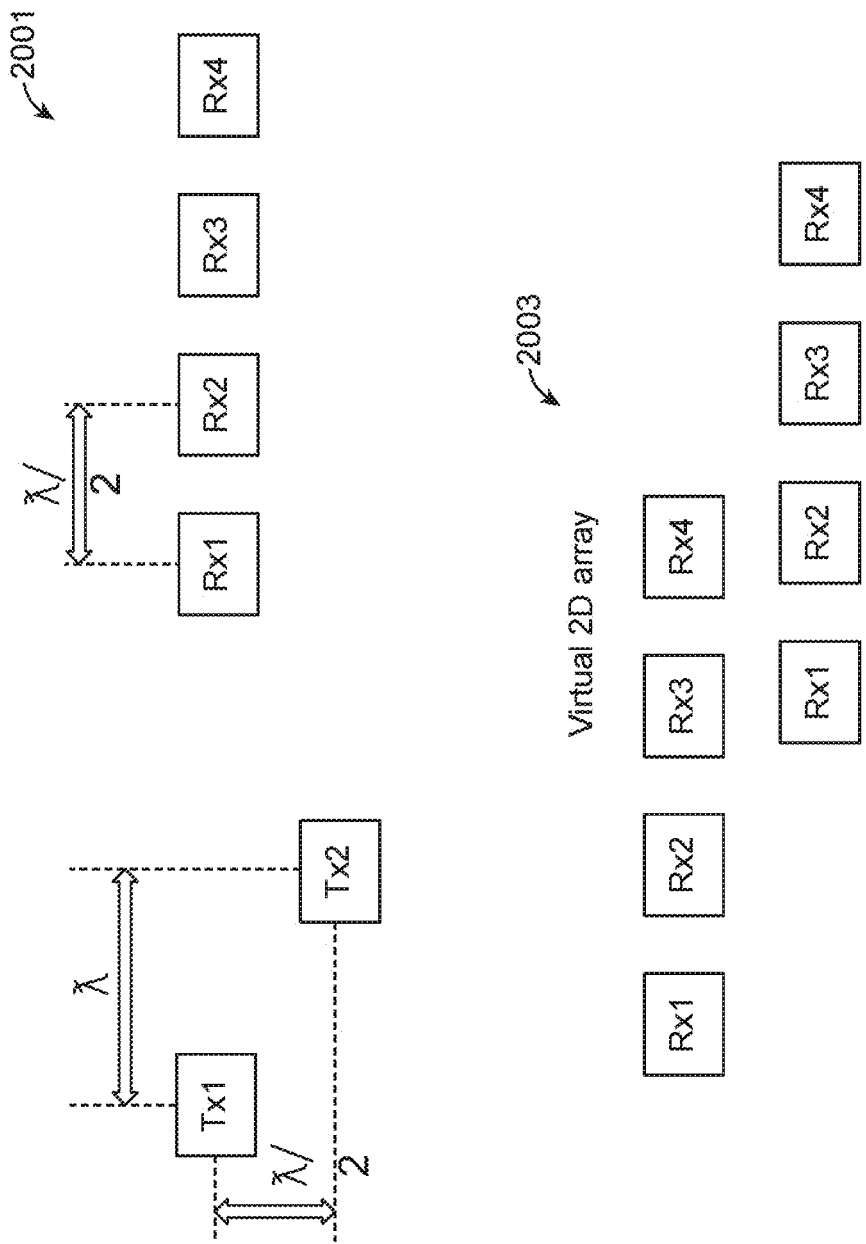
FIG. 20 is a simplified illustration of each antenna in an array according to examples of the present invention.

FIG. 20 is a simplified example of an antenna array according to an embodiment of the present invention. As shown, serial fed patch antennas can be included. In an example, each antenna array 2001 has 2 TX and 4 RX, or can have variations. In an example, each RX covers 120 degrees horizontal field-of-view. In an example, the Rx has a desirable wide vertical field-of-view. In an example, the antenna array has four (4) RX in an antenna array that are equally spaced by lambda over two horizontally.

In an example, each antenna array has two (2) TX in an antenna array that are spaced by lambda apart horizontally and lambda over two vertically to form a virtual 2D array with the 4 RX 2003. In an example, the present virtual antenna mapping is provided to achieve the goal of power balancing the physical channels across the multiple physical antennas especially when multiple input multiple output is deployed in the downlink. In an example, virtual antenna mapping gives an illusion that there are actually lesser antennas at the base station than it actually has. The unbalanced balanced power across two transmits paths are transformed into balanced power at physical antenna ports by virtual antenna mapping. This is achieved using phase and amplitude coefficients. Thus both the power amplifiers are optimally used even for signals transmitted on the first antenna. Of course, there can be other variations, modifications, and alternatives.

In an example, use of higher power with FMCW can be used to capture more granular features, such as breathing, heart rate, and other small scale features. In an example, lower power and UWB is desirable for more gross features, which has lower frequency. Lower frequency can also penetrate walls, and other physical features.

In an example, the present invention provides an FMCW sensor apparatus. The apparatus has at least three transceiver modules. Each of the transceiver modules has an antenna array to be configured to sense a back scatter of electromagnetic energy from spatial location of a zero degree location in relation to a midpoint of the device through a 360 degrees range where each antenna array is configured to sense a 120 degree range. In an example, each of the antenna array has a support member, a plurality of receiving antenna, a receiver integrated circuit coupled to the receiving antenna and configured to receive an incoming FMCW signal and covert the incoming FMCW signal into a base band signal, and a plurality of transmitting antenna. Each antenna array has a transmitter integrated circuit coupled to the transmitting antenna to transmit an outgoing FMCW signal. The apparatus has a virtual antenna array configured from the plurality of receiving antenna and the plurality of transmitting antenna to form a larger spatial region using the virtual antenna array, than a physical spatial region of the plurality of receiving antenna. In an example, the apparatus has a triangular configuration comprising a first antenna array, a second antenna array, and a third antenna array included in the at least three antenna arrays to provide a 360 degree visibility range as measured from a horizontal plane, and a 80 degree visibility range as measured from a vertical plane normal to the horizontal plane. The apparatus has a master control board coupled to each of the support members, and configured in a normal directional manner with reference to each of the support members. The apparatus has a housing enclosing the at least three transceiver modules.

In an example, the FMCW sensor apparatus comprises a switch configured between a plurality of FMCW transceivers, such that the switch is configured to select one of the three antenna arrays to sense the back scatters while the other two antenna arrays are turned off. In an example, the antenna array is configured to process electromagnetic radiation in a frequency range of 24 GHz to 24.25 GHz.

In an example, apparatus has a controller configured to control the switch and the three antenna array. In an example, the controller cycles through a predetermined process to decide which one of the three antenna array to activate while the other two antenna arrays are turned off. In an example, the three antenna array are configured to sense electromagnetic energy in a 24 GHz to 24.25 GHz frequency band. In an example, the sensing apparatus is spatially positioned within a center of a geographic location of a room to detect movement of human user. In an example, each of the sensor arrays is provided on a substrate member to be configured in the triangular configuration.

In an example, the apparatus has a housing. The housing has a maximum length of six to twenty four inches and width of no longer than six inches. In an example, the housing has sufficient structural strength to stand upright and protect an interior region within the housing.

In an example, the apparatus has a height characterizing the housing from a bottom region to a top region, a plurality of levels within the housing numbered from 1 to N, and a speaker device configured within the housing and over the bottom region. In an example, the apparatus has a compute module comprising a processing device over the speaker device, an artificial intelligence module configured over the compute module, a ultra-wide band ("UWB") module comprising an antenna array configured over the artificial intelligence module, and an audio module configured over the FMWC module. The apparatus has an inertial measurement unit ("IMU") module configured over the FMCW module.

In an example, the speaker device, the compute module, the artificial intelligence module, the UWB module, the FMCW module, the audio module, and the IMU module are arranged in a stacked configuration and configured, respectively, in the plurality of levels numbered from 1 to N.

In an example, the speaker device comprises an audio output configured to be included in the housing, the speaker device being configured to output energy within a 360 degree range from a midpoint of the device.

In an example, the compute module comprises a microprocessor based unit coupled to a bus. In example, the compute module comprises a signal processing core, a microprocessor core for an operating system, a synchronizing processing core configured to time stamp, and synchronize incoming information from each of the FMCW module, IMU module, and UWB module.

In an example, the apparatus has a real time processing unit configured to control the FMCW switch or the UWB switch or other switch requiring a real time switching operation of less than ½ milliseconds of receiving feedback from a plurality of sensors. In an example, the apparatus has a graphical processing unit configured to process information from the artificial intelligence module.

In an example, the artificial intelligence module comprises an artificial intelligence inference accelerator configured to apply a trained module using a neural net based process, the neural net based process comprising a plurality of nodes numbered form 1 through N.

In an example, the FMCW module comprises at least three antenna arrays to be configured to sense a back scatter of electromagnetic energy from spatial location of a zero degree location in relation to a midpoint of the device through a 360 degrees range where each antenna array is configured to sense a 120 degree range.

In an example, each of the antenna arrays comprises a FMCW transceiver and a switch configured between each of the FMCW transceiver and a controller, such that the switch is configured to select one of the three antenna arrays and the FMWC transceiver to sense the back scatters while the other two antenna arrays are turned off, and further comprising a serial interface.

In an example, the audio module comprises a micro phone array for detecting energy in a frequency range of sound for communication and for detecting a sound energy.

In an example, the UMU module comprises a support substrate, an electrical interface provided on the support structure, an accelerometer coupled to the electrical interface, a gyroscope coupled to the electrical interface, a compass coupled to the electrical interface, a UV detector configured to detect ultraviolet radiation coupled to the interface, a pressure sensor coupled to the interface, and an environmental gas detector configured and coupled to the interface to detect a chemical entity.

In an example, the present invention provides an apparatus for processing activities of a human user. The apparatus has an audio module and a compute module coupled to the audio module. The apparatus has a transceiver module coupled to the compute module. In an example, the transceiver module has an antenna array to be configured to sense a back scatter of electromagnetic energy in a frequency range of 24 GHz to 24.25 GHz from spatial location of a zero degree location in relation to a midpoint of the device through a 360 degrees range where each antenna array is configured to sense a 120 degree range.

In an example, the antenna array comprises a support member, a plurality of receiving antenna, a receiver integrated circuit coupled to the receiving antenna and configured to receive an incoming frequency modulated continuous wave (FMCW) signal and covert the incoming FMCW signal into a base band signal, a plurality of transmitting antenna, a transmitter integrated circuit coupled to the transmitting antenna to transmit an outgoing FMCW signal.

In an example, the apparatus has a virtual antenna array configured from the plurality of receiving antenna and the plurality of transmitting antenna to form a larger spatial region using the virtual antenna array, than a physical spatial region of the plurality of receiving antenna. In an example the apparatus has a master control board coupled to the support member, and configured in a normal directional manner with reference to the support member and a housing enclosing the transceiver modules, the compute module, and the audio module.

In an example, the present invention has methods using the apparatus, device, and systems. In an example, the method is for processing signals from human activities. The method includes generating an rf signal using a transceiver module coupled to a compute module and emitting the rf signal using one of three antenna array and sensing using one of the three antenna array configured from spatial location of a zero degree location in relation to a midpoint of the three antenna array through a 360 degrees range where each antenna array is configured to sense a 120 degree range to capture a back scatter of electromagnetic energy in a frequency range of 24 GHz to 24.25 GHz associated with a human activity.

In an example, the present invention provides an alternative radio frequency (RF) sensing apparatus. The apparatus has an ultra wide band (UWB) module comprising at least three ultra wide band (UWB) antenna arrays configured in a triangular arrangement to sense a back scatter of electromagnetic energy from a spatial location such that the triangular arrangement allows for sensing from a zero degree location in relation to a midpoint of the triangular arrangement through a 360 degree visibility range as measured from a horizontal plane, and a 80 degree visibility range as measured from a vertical plane that is normal to the horizontal plane where each UWB antenna array is configured to sense at least a 120 degree range.

In an example, each of the UWB antenna arrays comprises a support member, a plurality of transmitting antenna spatially configured on a first portion of the support member, a transmitting integrated circuit coupled to each of the plurality of transmitting antenna and configured to transmit an outgoing UWB signals, a plurality of receiving antenna spatially configured on second portion of the support member, and a receiving integrated circuit coupled to each of the plurality of receiving antenna and configured to receive an incoming UWB signal and configured to convert the UWB signal into a base band signal.

In an example, the apparatus has a frequency modulated continuous wave module comprising at least three frequency modulated continuous wave (FMCW) transceiver modules. Each of the FMCW transceiver modules has a FMCW antenna array. In an example, the three FMCW transceiver modules are configured in a triangular arrangement to sense a back scatter of electromagnetic energy from spatial location such that the triangular arrangement allows for sensing from a zero degree location in relation to a midpoint of the triangular arrangement through a 360 degree visibility range as measured from a horizontal plane, and a 80 degree visibility range as measured form a vertical plane that is normal to the horizontal plane where each FMCW antenna array is configured to sense at least a 120 degree range.

In an example, each of the FMCW antenna array comprises a support member, a plurality of receiving antenna, a receiver integrated circuit coupled to the receiving antenna and configured to receive an incoming FMCW signal and covert the incoming FMCW signal into a base band signal, a plurality of transmitting antenna, a transmitter integrated circuit coupled to the transmitting antenna to transmit an outgoing FMCW signal, and a virtual antenna array configured from the plurality of receiving antenna and the plurality of transmitting antenna to form a larger spatial region using the virtual antenna array, than a physical spatial region of the plurality of receiving antenna.

In an example, the apparatus has a master control board coupled to each of the support members, and configured in a normal directional manner with reference to each of the support members and a housing enclosing the at least three FMCW transceiver modules and the at least three UWB antenna arrays.

In an example, the apparatus has a FMCW switch configured between a plurality of FMCW transceivers, such that the FMCW switch is configured to select one of the three FMCW antenna arrays to sense the back scattered signal while the other two FMCW antenna arrays are turned off; wherein each of the FMCW antenna array is configured to process electromagnetic radiation in a frequency range of 24 GHz to 24.25 GHz.

In an example, the apparatus has a FMCW controller configured to control the FMCW switch and the three FMCW antenna array, the FMCW controller cycles through a predetermined process to decide which one of the three FMCW antenna array to activate while the other two FMCW antenna arrays are turned off. In an example, the three FMCW antenna array are configured to sense electromagnetic energy in a 24 GHz to 24.25 GHz frequency band. In an example, the RF sensing apparatus is spatially positioned within a center of a geographic location of a room to detect movement of human user using either the outgoing FMCW signal or the outgoing UWB signal.

In an example, the apparatus has a UWB switch configured between a plurality of UWC transceivers, such that the UWB switch is configured to select one of the three UWB antenna arrays to sense the back scatters while the other two UWB antenna arrays are turned off. In an example, the apparatus has a UWB controller configured to control the UWB switch and the UWB three antenna array, the UWB controller cycles through a predetermined process to decide which one of the three UWB antenna array to activate while the other two UWB antenna arrays are turned off In an example, the at least three UWB antenna array are configured to sense electromagnetic energy ranging from 6 to 8 GHz in frequency.

In an example, the housing has a maximum length of six to twenty four inches and width of no longer than six inches, the housing having sufficient structural strength to stand upright and protect an interior region within the housing; a height characterizing the housing from a bottom region to a top region; a plurality of levels within the housing numbered from 1 to N. The apparatus can also have a speaker device configured within the housing and over the bottom region, a compute module comprising a processing device over the speaker device, an artificial intelligence module configured over the compute module, an audio module, and an inertial measurement unit ("IMU") module.

In an example, the present invention has an alternative radio frequency (RF) sensing apparatus. The apparatus has an ultra wide band (UWB) antenna array configured in a spatial arrangement to sense a back scatter of electromagnetic energy from a spatial location such that the spatial arrangement allows for sensing from a first location in relation to a second location. In an example, the UWB antenna array comprises a support member, a plurality of transmitting antenna spatially configured on a first portion of the support member, a transmitting integrated circuit coupled to each of the plurality of transmitting antenna and configured to transmit an outgoing UWB signal, a plurality of receiving antenna spatially configured on second portion of the support member, and a receiving integrated circuit coupled to each of the plurality of receiving antenna and configured to receive an incoming UWB signal and configured to convert the UWB signal into a base band signal.

In an example, the apparatus has a frequency modulated continuous wave (FMCW) transceiver module. In an example, the FMCW transceiver modules has a FMCW antenna array. In an example, the FMCW transceiver module is configured to sense a back scatter of electromagnetic energy from the first location in relation to a second location.

In an example, the FMCW antenna array comprises a support member, a plurality of receiving antenna, a receiver integrated circuit coupled to the receiving antenna and configured to receive an incoming FMCW signal and covert the incoming FMCW signal into a base band signal, a plurality of transmitting antenna; a transmitter integrated circuit coupled to the transmitting antenna to transmit an outgoing FMCW signal, and a virtual antenna array configured from the plurality of receiving antenna and the plurality of transmitting antenna to form a larger spatial region using the virtual antenna array, than a physical spatial region of the plurality of receiving antenna.

In an example, the apparatus has a master control board coupled to each of the support members, and configured in a normal directional manner with reference to each of the support members and a housing enclosing the FMCW transceiver module and the UWB antenna array.

In an example, the apparatus has a FMCW switch configured to the FMCW transceiver, such that the FMCW switch is configured to select the FMCW antenna array to sense the back scattered signal; the FMCW antenna array is configured to process electromagnetic radiation in a frequency range of 24 GHz to 24.25 GHz. In an example, the apparatus has a FMCW controller configured to control the FMCW switch and the FMCW antenna array, the FMCW controller cycles through a predetermined process to decide when the FMCW antenna array is activated. In an example, the FMCW antenna array is configured to sense electromagnetic energy in a 24 GHz to 24.25 GHz frequency band.

In an example, the RF sensing apparatus is spatially positioned within a center of a geographic location of a room to detect movement of human user using either the outgoing FMCW signal or the outgoing UWB signal. In an example, the apparatus has a UWB switch configured to the UWC transceiver, such that the UWB switch is configured to select the UWB antenna array to sense the back scattered signal. In an example the apparatus has a UWB controller configured to control the UWB switch and the UWB antenna array, the UWB controller cycles through a predetermined process to decide when the UWB antenna array is activated. In an example, the UWB antenna array is configured to sense electromagnetic energy ranging from 6 to 8 GHz in frequency.

In an example, the housing has a maximum length of six to twenty four inches and width of no longer than six inches, the housing having sufficient structural strength to stand upright and protect an interior region within the housing; a height characterizing the housing from a bottom region to a top region; a plurality of levels within the housing numbered from 1 to N. In an example, the apparatus can have a speaker device configured within the housing and over the bottom region, a compute module comprising a processing device over the speaker device, an artificial intelligence module configured over the compute module, an audio module, and an inertial measurement unit ("IMU") module.

In an example, the present invention also has an apparatus for monitoring a human user. The apparatus has a movable housing. In an example, the housing has a maximum length of six to twenty four inches and width of no longer than six inches. In an example, the housing has sufficient structural strength to stand upright and protect an interior region within the housing. The housing has a height characterizing the housing from a bottom region to a top region; a plurality of levels within the housing numbered from 1 to N. In an example, each of the levels has a module selected from at least one of:

an ultra wide band (UWB) antenna array configured in a spatial arrangement to sense a back scatter of electromagnetic energy from a spatial location such that the spatial arrangement allows for sensing from a first location in relation to a second location, the UWB antenna array comprising:
  a support member;
  a plurality of transmitting antenna spatially configured on a first portion of the support member;
  a transmitting integrated circuit coupled to each of the plurality of transmitting antenna and configured to transmit an outgoing UWB signal;
  a plurality of receiving antenna spatially configured on second portion of the support member;
  a receiving integrated circuit coupled to each of the plurality of receiving antenna and configured to receive an incoming UWB signal and configured to convert the UWB signal into a base band signal; and
a frequency modulated continuous wave (FMCW) transceiver module, the FMCW transceiver modules having a FMCW antenna array, the three FMCW transceiver module being configured to sense a back scatter of electromagnetic energy from the first location in relation to a second location, the FMCW antenna array comprising:
  a support member;
  a plurality of receiving antenna;
  a receiver integrated circuit coupled to the receiving antenna and configured to receive an incoming FMCW signal and covert the incoming FMCW signal into a base band signal;
  a plurality of transmitting antenna;
  a transmitter integrated circuit coupled to the transmitting antenna to transmit an outgoing FMCW signal;
  a virtual antenna array configured from the plurality of receiving antenna and the plurality of transmitting antenna to form a larger spatial region using the virtual antenna array, than a physical spatial region of the plurality of receiving antenna;
a master control board coupled to each of the support members, and configured in a normal directional manner with reference to each of the support members;
a speaker device configured within the housing and over the bottom region;
a compute module comprising a processing device over the speaker device;
an artificial intelligence module configured over the compute module;
an audio module; and
an inertial measurement unit ("IMU") module.

wherein the FMCW antenna array is configured to sense electromagnetic energy in a 24 GHz to 24.25 GHz frequency band; and the UWB antenna array is configured to sense electromagnetic energy ranging from 6 to 8 GHz in frequency.

Of course, there can be other variations, modifications, and alternatives.

Figure 21:
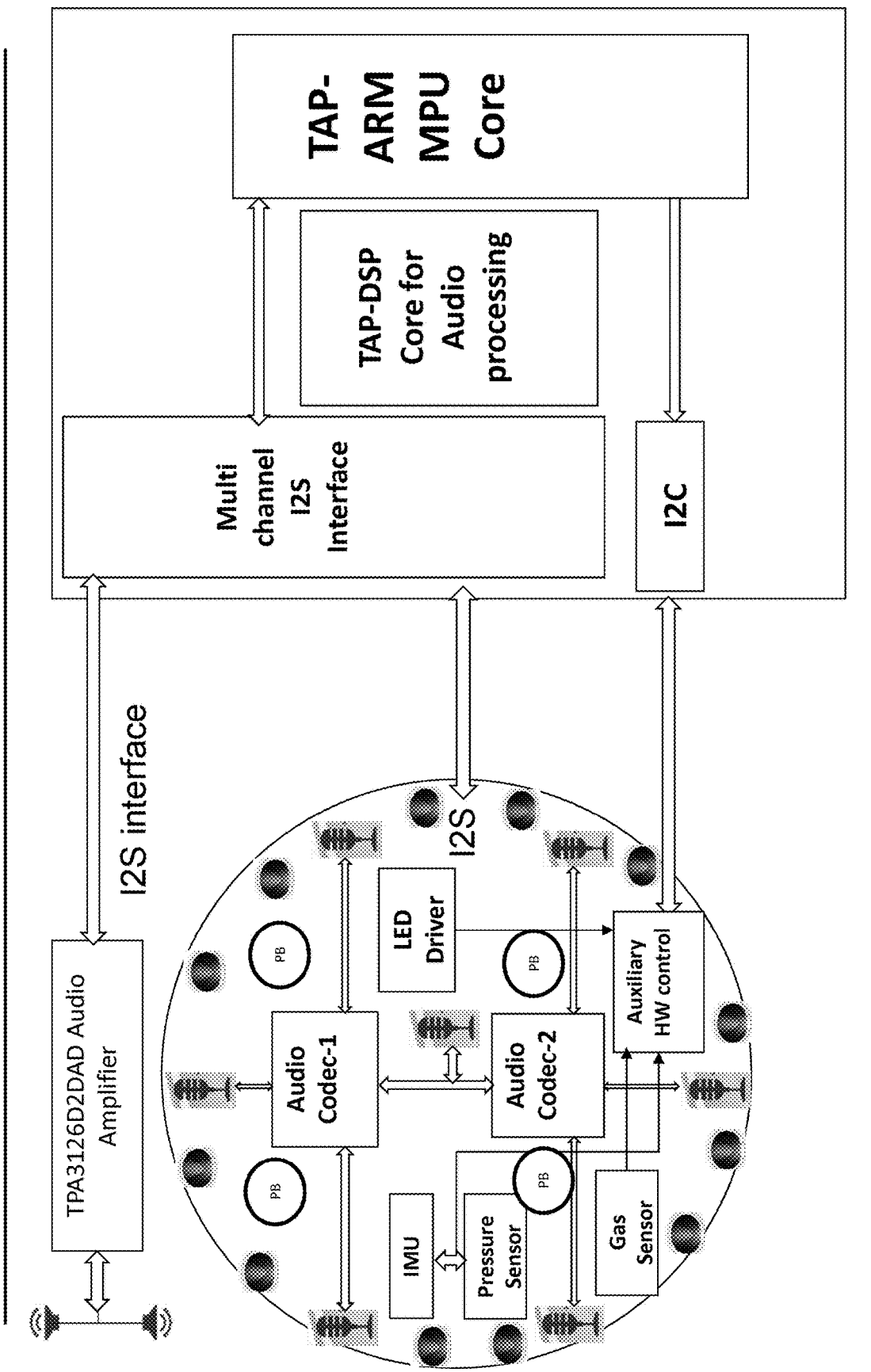
FIG. 21 is a simplified top-view diagram of an audio module according to an example of the present invention.

FIG. 21 is a simplified top-view diagram of an audio module according to an example of the present invention. In an example, the apparatus has an audio module, as represented by circularly shaped substrate member. The audio module has a microphone array comprising seven microphones, including six peripheral microphones and one center microphone configured and arranged in circular array, although there can be other configurations, quantities, and spatial layouts of the microphones. In an example, each of the microphones is electrically connect to a dual four (4) channel analog to digital converter (ADC) with 103 db of signal to noise ratio, or other suitable designs.

In an example, the analog to digital converter uses a bus to connect to a processing system, including a processing device, a signal processor, and other elements. In an example, the ADC uses an I2S interface. In an example, the I2S interface has been developed by Philips Semiconductor (known today as NXP Semiconductors). In an example, the interface uses a push pull data signal, width of one data line (SD)+2 clock lines (SCK, WS), and a serial protocol. In an example as defined in Wikipedia.com, the "I²S" (Inter-IC Sound), pronounced eye-squared-ess, is an electrical serial bus interface standard used for connecting digital audio devices together. In an example, I2S communicates pulse coded modulation ("PCM") audio data between integrated circuits in an electronic device. In an example, the I²S bus separates clock and serial data signals, resulting in simpler receivers than those required for asynchronous communications systems that need to recover the clock from the data stream.

In an example, the processing system has a digital signal processing (DSP) core, which receives digital audio and performs a beam-forming operation, including deploying an adaptive spectral noise reduction process and the multiple source selection (MSS) process to enhance the audio quality. In an example, the processing devices, including microprocessing unit and audio signal processing unit are provided in a separate compute module, or other hardware device.

In an example, the multiple source selection processes inputs audio information from the plurality of microphones, each of which is sensing an audio signal from a spatial region, in the array directly to the DSP core, without transferring such data into the processing device, for faster detection and selection of at least one of the microphone devices in the array that has the highest audio signal therefrom. Once the microphone has been selected, the audio information from the selected microphone is outputted or further processed using the processing system. In an example, the multiple source selection processes achieves at least a few milliseconds of time off standard processing times, which often run through the processor, where the audio information traverses through the processing device. As shown, audio signals are captured from surroundings, converted to digital signals via A/D converter, transmitted to the digital processing device for audio processing, without traversing the signals through the ARM micro-processing unit core, as shown.

In an example, the ADC for the audio module has a dedicated I2S channel that is also interfaced to drive an audio amplifier coupled to a speaker. In an example, multiple speakers such as dual speakers are integrated into the apparatus. In an example, the audio amplifier can be one listed under part number TPA3126D2DAD manufactured by Texas Instruments Incorporated, among others. In an example, the driver can be a 50-W, stereo, low-idle-current Class-D amplifier in a thermally enhanced package. In an example, the driver has a hybrid modulation scheme, which dynamically reduces idle current at low power levels to extend the battery life of portable audio systems (e.g., Bluetooth speakers, and others). In an example, the Class-D amplifier integrates full protection features including short circuit, thermal shutdown, overvoltage, under voltage, and DC speaker protection. Faults are reported back to the processor to prevent devices from being damaged during overload conditions. Other features can also be included.

In an example, the audio module can also include other sensing devices. As an example, the audio module includes an inertial measurement device, a pressure sensor, a gas sensor, and a plurality of LED devices, each of which is coupled to an LED driver. Each of the devices is coupled to auxiliary control hardware, which communicates to a microprocessing unit core using a bus, such as the I2C bus, but can be others.

Figure 22:
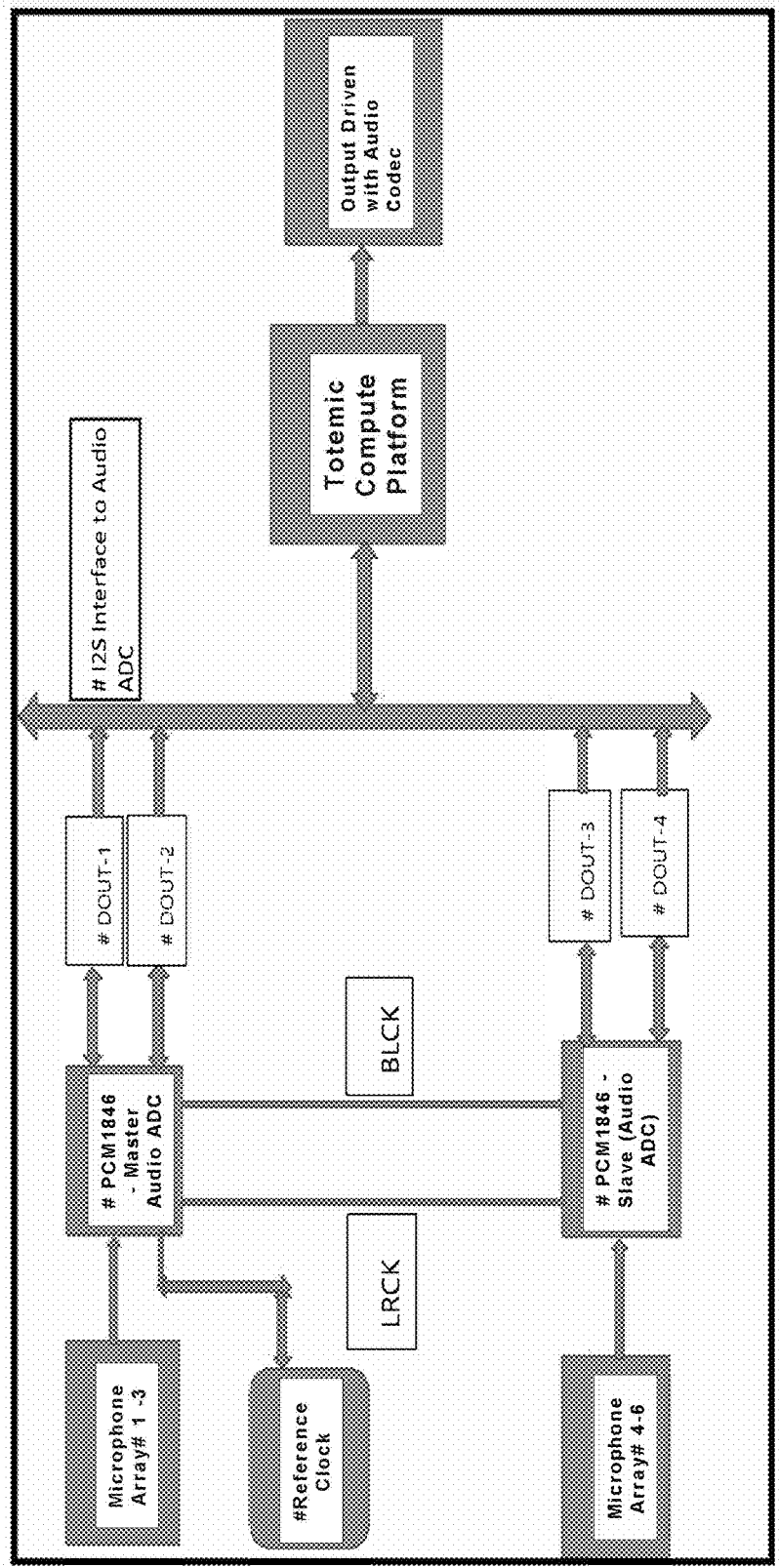
FIGS. 22 and 23 are respectively a simplified circuit diagram and microphone array arrangement according to an example of the present invention.
Figure 23:
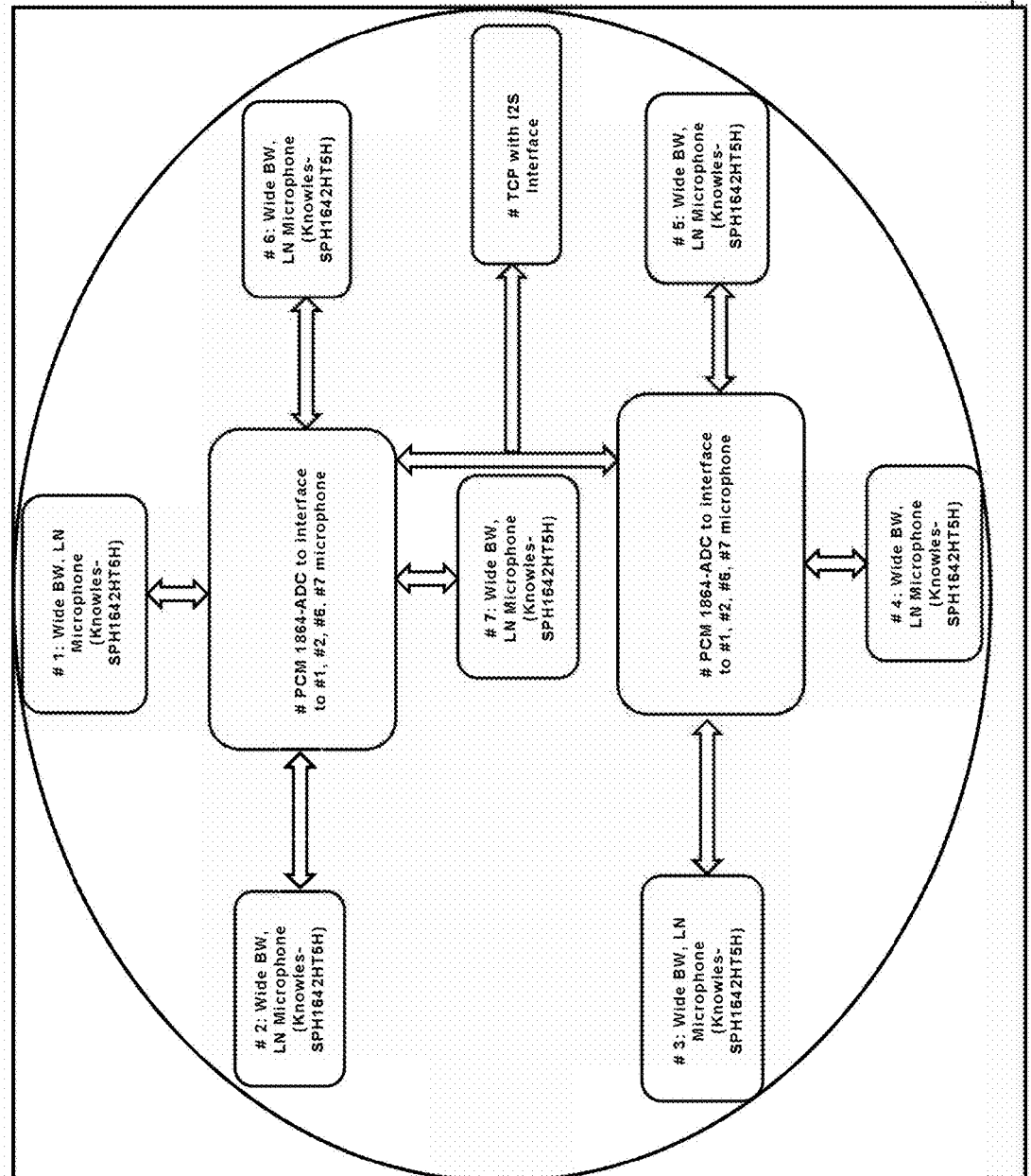

FIGS. 22 and 23 are respectively a simplified circuit diagram and microphone array arrangement according to an example of the present invention. As shown, microphone arrays 1-3 couple to an audio analog to digital converter (ADC), which acts as a master, and is coupled to a reference clock. As shown, the ADC can be a PCM1864 circular microphone board (CMB) from Texas Instruments Incorporated. The ADC is a low-cost easy-to-use reference design for applications that require clear-spoken audio, such as voice triggering and speech recognition. The ADC design uses a microphone array to capture a voice signal, and converts it to a digital stream that can be used by DSP systems to extract clear audio from noisy environments. Microphone arrays 4-6 are coupled to slave ADC device, which is coupled to the master ADC device. In an example, digital audio outputs are included and feed digital audio signals into a bus, such as the I2S interface, among others. The I2S interface couples to a computing system, which includes audio output to an audio driver, and speakers.

Figure 24:
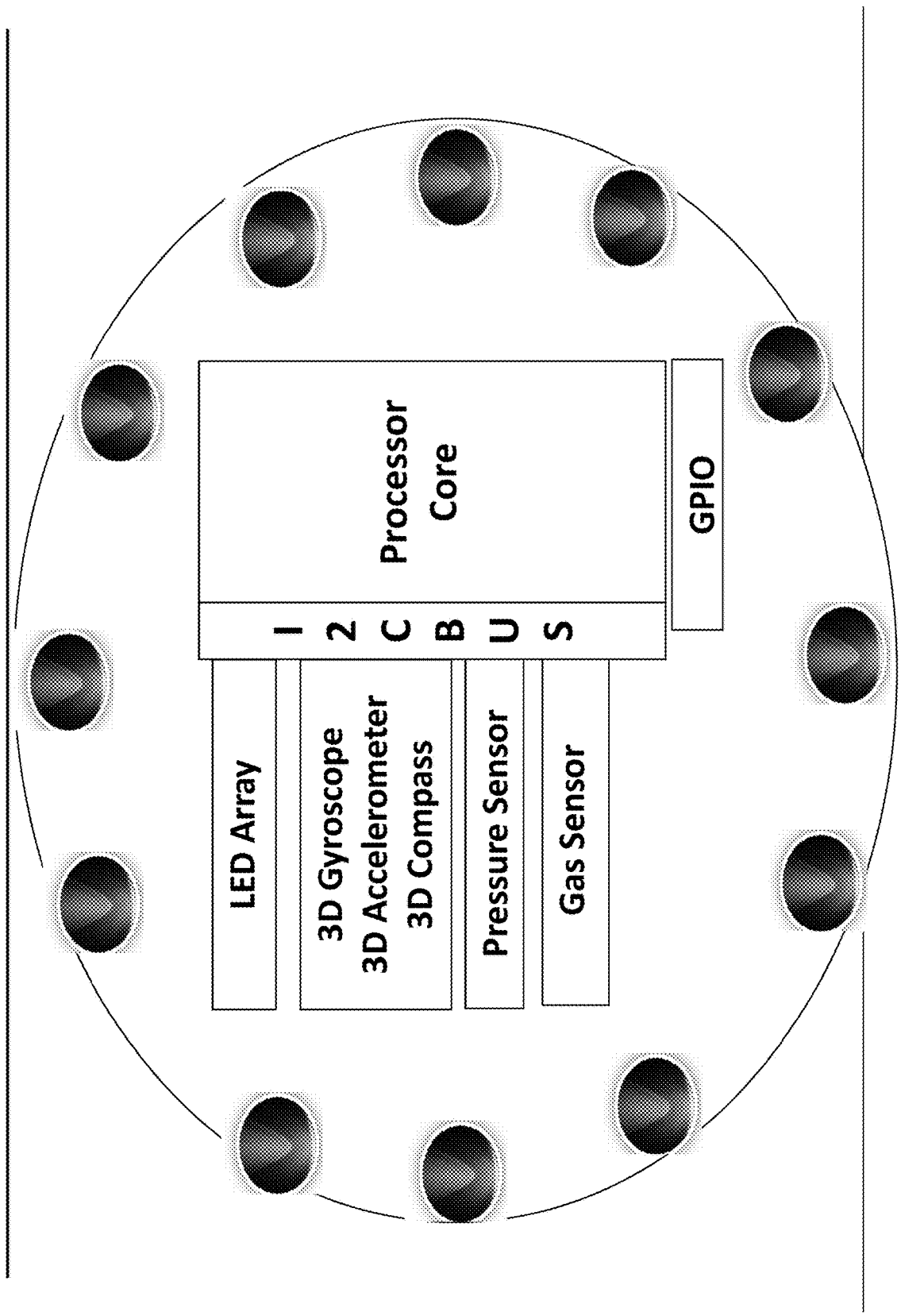
FIG. 24 is a simplified top-view diagram of an inertial sensing module according to an example of the present invention.

FIG. 24 is a simplified top-view diagram of an inertial sensing module according to an example of the present invention. In an example, the apparatus has an inertial motion and sensing module. In an example, the module has a multi-axis motion sensor. In an example, the sensor can be a part listed under TDK-ICM20948 that provides a 9-axis motion sensor including a three (3) axis accelerometer, a magnetometer, a gyroscope and a digital motion processor. In an example, the module has an interface that has a slave I2C communication interface to the processing system. The module has a master I2C interface to connect to an auxiliary pressure sensor (e.g., Bosch-BMP 180) to perform similar to a ten (10) axis motion sensor.

In an example, the module has an accelerometer, a gyroscope, a magnetometer to form 9-axis inertial motion unit sensor. In an example, these sensors are important to detect the accurate positioning of the apparatus. In an example, the module also provides for additional information regarding the displacement of the apparatus from one spatial location to other spatial location.

In an example, the module has a pressure sensor to provide additional information of pressure changes in the surroundings or ambient area. In an example, the pressure sensor can be configured with the processing to detect opening and/or closing of a door or other building structure.

In an example the module has a gas sensor. In an example, the gas sensor is configured with the processor to detect the amount of carbon monoxide and other toxic gases that can be present in the surroundings where our device is located. In an example, the gas sensor is one sold under the part number ICM 10020 from TDK or other manufacturers.

In an example, the module has an LED array. In an example, the LED array can be a twelve (12) RGBW LED Ring for the Lighting Purposes. LED Driver used such as the one sold under part number LP5569. As shown, the LED array is configured spatially around a peripheral region of the substrate member, which is circular in this example.

As shown, each of the sensors communicates using the I2C bus, which communicates to various input/output devices on the processing system, as will be described in more detail below. Also shown is a general purpose input and output interface coupled to the processing system.

FIG. 25 is a simplified diagram of a user interface according to an example of the present invention. In an example, the module also has a user interface. An example of an easy to use interface includes buttons such as the general purpose input and output (GPIO) buttons configured on an outer region of the housing. In an example, 4 GPIO push buttons are placed for multi-purpose applications and configured to the housing, and coupled to the processing device. As shown, the buttons include (1) make outgoing call; (2) receive incoming call or mute the A/C audio CODEC; (3) volume up for the A/C audio CODEC; and (3) volume down for the A/C audio CODEC. Of course, there can be other configurations for the GPIO buttons.

Figure 26:
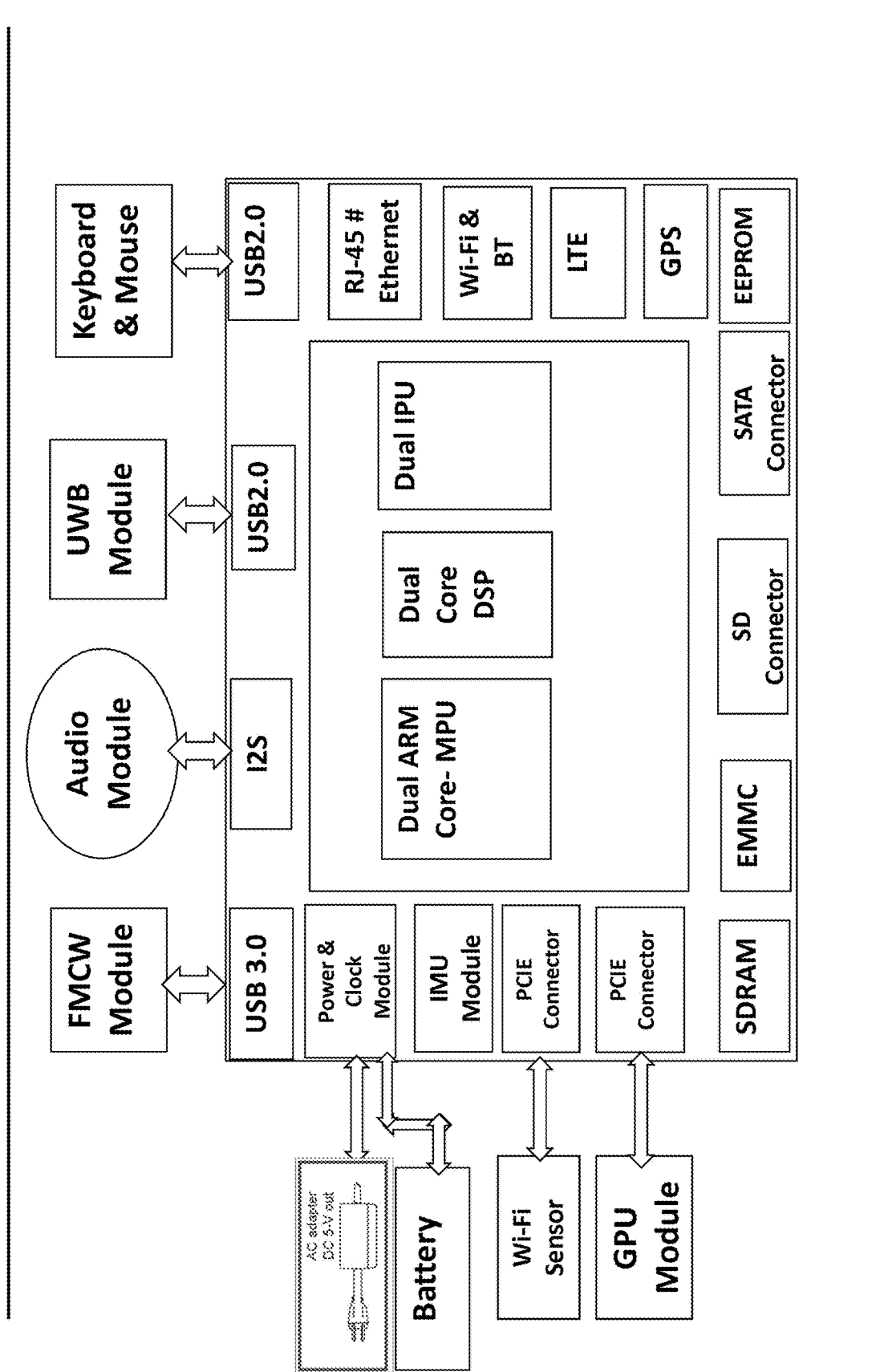
FIG. 26 is a simplified diagram of a processing system according to an example of the present invention.

FIG. 26 is a simplified diagram of a processing system according to an example of the present invention. As shown, the processing system has a system on a chip processing platform, that is a single integrated circuit chip, including a dual ARM core micro-processing unit, a dual core digital signal processor, and a dual core image processing unit, among related firmware, interconnections, power management, and other features. Each of the processing resource is coupled to a bus or multiple buses.

In an example, the system has multiple interfaces. A USB 3.0 interface communicates to the FMCW module. The I2S interface communicates to the audio module. A USB 2.0 interface communicates to the UWB module. Another USB 2.0 interface communicates to a user interface, such as a keyboard and a mouse. Other types of serial interfaces can also be included. The system also has an RJ-45 and Ethernet interface, a Wi-Fi and Bluetooth interface, a cellular interface, such as LTE, among others. The system has a global positioning sensor interface. The system has a power and clock module for power and clocking functions. The system has an inertial measurement unit connector and module. The system has multiple PCIE connector interfaces, one of which is coupled to a Wi-Fi sensor device. Other features include dynamic random access memory interface, embedded multi-media card connection and module, a solid disk drive connector, and a serial advanced technology attachment connector, among others.

An example of the processing system can be a single integrated circuit chip manufactured by Texas Instruments Incorporated sold as AM572x Sitara Arm applications processors. In a datasheet by for the Sitara Arm by Texas Instruments, "AM572x devices bring high processing performance through the maximum flexibility of a fully integrated mixed processor solution. The devices also combine programmable video processing with a highly integrated peripheral set. Cryptographic acceleration is available in every AM572x device. Programmability is provided by dual-core Arm Cortex-A15 RISC CPUs with Neon™ extension, and two TI C66x VLIW floating-point DSP cores. The Arm allows developers to keep control functions separate from other algorithms programmed on the DSPs and coprocessors, thus reducing the complexity of the system software. Additionally, TI provides a complete set of development tools for the Arm and C66x DSP, including C compilers, a DSP assembly optimizer to simplify programming and scheduling, and a debugging interface for visibility into source code execution."

In an example, the processing system is coupled to an energy source, including a battery and a plug connection. The system also has a graphical processing module or artificial intelligence module for performing processing functions from data received from the interfaces. An example of the processing unit is one sold under the Movidius™ brand by Intel Corporation.

In an example, Movidius provides the ultimate in low-power vision processing solutions, which include the Myriad 2 family of vision processing units (VPUs) plus a comprehensive Myriad Development Kit (MDK), a reference hardware EVM and optional Machine Vision Application Packages. In an example, The Myriad 2 MA2x5x family of system-on-a-chip (SoC) devices offers significant computation performance and image processing capability with a low-power footprint. The Myriad 2 lineup includes the following product configurations: MA2150: 1 Gbit DDR MA2155: 1 Gbit DDR and secure boot MA2450: 4 Gbit DDR MA2455: 4 Gbit DDR and secure boot.

In an example, the Myriad 2 VPUs offer TeraFLOPS (trillions of floating-point operations per second) of performance within a nominal 1 Watt power envelope. The Myriad 2 architecture includes enough performance to support multiple cameras with flexible image signal processing pipelines for each camera, and software programmable vision processing with fixed- and floating-point datatypes supported. A robust overall dataflow design ensures mitigation of processing bottlenecks.

In an example, Myriad 2 MA2x5x incorporates an innovative approach to combine image signal processing with vision processing. A set of imaging/vision hardware accelerators supports a world-class ISP pipeline without any round trips to memory; at the same time they are repurposed to accelerate developers' vision processing algorithms in conjunction with a set of special purpose vision processor cores. All processing elements are tied together with a multi-ported memory that enables implementation of demanding applications with high efficiency. Further details can be found in a datasheet for Myriad 2 by Intel Corporation. Of course, other processing units can also be suitable for the processing applications.

Figure 27:
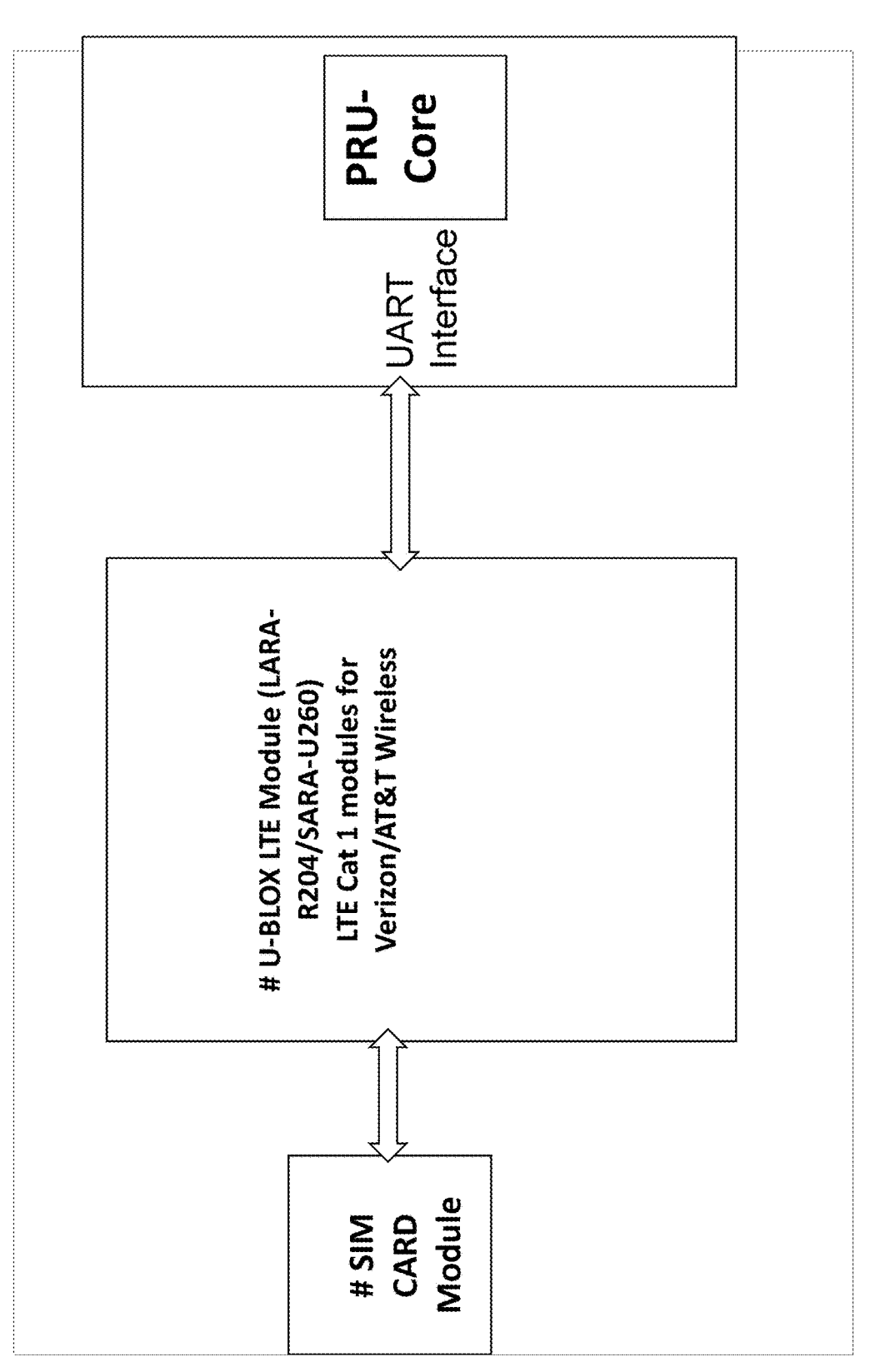
FIG. 27 is a simplified block diagram of a cellular module coupled to the processing system.

FIG. 27 is a simplified block diagram of a cellular module coupled to the processing system. In an example, the cellular module can be any suitable design, such as one called the U-BLOX LTE Module sold under part number LARA-R204/SARA-U260, among others. The module can be configured to service providers such as AT&T Wireless, Sprint, Verizon, and others. In an example, the module communicates via a universal asynchronous receiver-transmitter (UART) configured for asynchronous serial communication in which the data format and transmission speeds are configurable. The module is also coupled to a removable phone number SIM card for configuring the system. Of course, there can be other variations, modifications, and alternatives.

In an example, the present invention provides a system for capturing information from a spatial region to monitor human activities. In an example, the system has a housing, the housing having a maximum length of six to twenty four inches and width of no longer than six inches, but can be other dimensions. In an example, the housing has sufficient structural strength to stand upright and protect an interior region within the housing, but can include variations. In an example, the housing has a height characterizing the housing from a bottom region to a top region and a plurality of levels within the housing numbered from 1 to N, each of the levels configured with one or more modules.

In an example, the system has an audio module comprising a substrate member and a plurality of peripheral microphone devices spatially disposed along a peripheral region of the substrate member. In an example, each of the peripheral microphone devices has an analog output. In an example, the module has a center microphone device spatially disposed within a center region of the substrate member. In an example, the center microphone device has an analog output. In an example, the module has an analog to digital converter coupled to each of the analog outputs. The module has a spatial configuration comprising a circularly shaped region for the peripheral region to provide a 360 degrees field of view for the plurality of peripheral microphone devices. A bus device is coupled to each of the analog to digital converters. In an example, the bus device communicates with each of the plurality of peripheral microphone devices and the center microphone device. The module is coupled to a signal processor coupled to the bus device. The module is coupled to a processor device coupled to the signal processing device and is configured to process an audio information comprising an audio event from the plurality of microphone devices using the signal processors without transferring the audio information to the processing device to achieve a faster selection process of at least one milliseconds to select one of the microphone devices that has a strongest audio signal, and then transfers the audio information from the selected microphone devices. The system also has a cellular network module comprising an interface, which is coupled to the processing device. The system has a user interface configured on an exterior portion of the housing, and coupled to the processor. The user interface allows for a user to initiate and make external calls via the cellular network when desirable or also receive external calls from the network.

In an example, the system has other elements. That is, a speaker device is coupled to the processor device; and an audio driver device is coupled to drive the speaker device. In an example, an LED array is coupled to the processor device. In an example, a plurality of MEMS devices are coupled to the processor device. In an example, a gas sensor device is coupled to the processor device. In an example, a pressure sensor device is coupled to the processor device. In an example, the user interface can be a general purposes input and output device.

In an example, the system has an inertial measurement module comprising an LED array, an accelerometer device, a gas sensor device, and a pressure sensor device configured to detect a pressure within an environment of the housing. In an example, the inertial measurement module comprising a gas sensor to detect a presence of carbon dioxide and coupled to the processor device configured to send out an alert based upon a level of carbon dioxide. In an example, the system has a plurality of LED devices configured spatially around a periphery of the substrate member to allow for illumination of electromagnetic radiation. In an example, the inertial measurement module comprising a i2C bus coupled to a plurality of LED devices, a gyroscope device, an accelerometer device, a compass device, a pressure device, and a gas sensor, the i2C bus coupled to the processing device. In an example, the processing unit comprises an ARM processing unit coupled to a digital signal processor and an image processing unit.

Optionally, the system has a network module comprising an interface, which is coupled to the processing device. In an example, the system has a speaker device coupled to the processor device, and an audio driver device coupled to the speaker device, the processer device being configured with the network module to communicate audio information to output acoustic energy from the speaker device. The system has a user interface configured on an exterior portion of the housing, and coupled to the processor.

In an example, the present invention provides a method of capturing information from a spatial region to monitor human activities. In an example, the method uses an apparatus comprising a housing within a spatial region of a living quarter, which is occupied by a human user or users. In an example, the housing has sufficient structural strength to stand upright and protect an interior region within the housing, the housing having a plurality of levels within the housing numbered from 1 to N. Each of the levels configured with one or more modules, which can include any of the ones described herein and others.

In an example, the housing has an audio module comprising: a substrate member; a plurality of peripheral microphone devices spatially disposed along a peripheral region of the substrate member, each of the peripheral microphone devices having an analog output; a spatial configuration using an edge region for the peripheral region to provide a 360 degrees field of view from the plurality of peripheral microphone devices; a bus device coupled to each of the analog to digital converters, the bus device communicating with each of the plurality of peripheral microphone devices; a signal processor coupled to the bus device; and a microprocessor device coupled to the signal processing device.

In an example, the method includes sensing a plurality of audio signals comprising an audio event from each of the plurality of microphone devices. Each of the plurality of microphone device can be receiving an audio signal of a different signal strength based upon a spatial location of each of the microphone devices. The method includes converting each of the audio signals from each of the microphone devices into a plurality of digital signals in a first format using an analog to digital converter. In an example, the method includes processing the digital signals in the first format to a second format, which can be compressed or other form to be transported via an interface. The method includes transferring the digital signals in the second format using a dedicated interface device from each of the plurality of microphone devices into a receive interface device coupled to the signal processing device without transferring the digital signals in the second format to the micro processing device. The method processes information associated with the digital signals using the signal processing device to select one of the microphone devices that has a strongest audio signal as compared to any of the other microphone devices; and transfers information associated with the digital signals from the selected microphone device to an outgoing interface device. In a preferred example, the method includes processing the digital signals from the selected microphone device using an artificial intelligence process to identify the event.

In an example, the technique transfers learned information and activity information to third parties. The technique teaches itself to learn high level behavior that are indicative of a person's welfare using artificial intelligence techniques. In an example, the present technique will then generate summary of such activities and send it out to the human's loved ones, caretaker or even emergency response team depending on the urgency of the situation. For example for regular days, the technique can simply send short summary like "your mom had a routine activity today", or "She was much less active today." In an example, where the human has a care taker visiting few times a week, the technique can send a notification to them, "It seems she struggles more on yesterday", so that the care taker can pay a visit to make sure everything is fine. Alternatively, the technique can be more acute events like fall, shortness of breathing, or others, that needs quick attention. In these scenarios, the technique can notify medical response team to provide immediate help. Of course, there can be other variations, modifications, and alternatives.

In an example, the present technique can categorize a human target with the listed ADLs, among others. Examples of ADLs including among others, bathing, brushing teeth, dressing, using toilet, eating and drinking, and sleeping. Other ADLs include preparing meals, preparing drinks, resting, housekeeping, using a telephone, taking medicine, and others. Ambulatory activities including among others walking, doing exercise (e.g., running, cycling), transitional activities (e.g., sit-to-stand, sit-to-lie, stand-to-sit, lie-to-sit in and out of bed or chair), and stationary activities (e.g., sits in sofa, stand for a while, lie in bed or sofa). Of course, there can be other variations, modifications, and alternatives.

In an alternative example, the present technique can determine activities of a human target with any one of the activities listed. The listed activities, including among others, and combinations of going out, preparing breakfast, having breakfast, preparing lunch, having lunch, preparing dinner, having dinner, washing dishes, having snack, sleeping, watching TV, studying, having a shower, toileting, having a nap, using the Internet, reading a book, shaving, brushing teeth, telephone, listening to music, doing house cleaning, having a conversation, entertain guest, among others.

In an example, the present technique can also identify a rare event. In an example, the technique identifies when a senior human falls inside a home with no one around. In an example, the technique is robust, without any false negatives. In an example, the technique uses looking at sequence of events that are before to the potential fall and after a potential fall. In an example, the technique combines the contextual information to robustly determine if a fall has occurred. Of course, there can be other variations, modifications, and alternatives.

In an example, the technique also detects and measures vital signs of each human target by continuous, non-intrusive method. In an example, the vital signs of interest include a heart rate and a respiratory rate, which can provide valuable information about the human's wellness. Additionally, the heart rate and respiratory rate can also be used to identify a particular person, if more than two target humans living in a home. Of course, there can be other variations, modifications, and alternatives.

By understanding the context of how the target human (e.g., elderly) is doing, the technique can also provide valuable feedback directly to the elderly using a voice interface. For example, the technique can sense a mood of the human based on sequence of activities and vital signs of the human and then ask, "Hi do you want me to call your son". Based upon the feedback from the human, the technique can help connect to a third party (or loved one) if their answer is positive. Of course, there can be other alternatives, variations, and modifications.

Techniques for Improving Sleep

In an example, the present technique provides a method for processing signals from a human user in connection with a sleep state. Preferably, the method includes using information from the signals for digital cognitive behavioral therapy to improve a sleep state of the human user. In an example, the method generally includes sensing of human activities, processing information from such sensing, outputting a task to the user, monitoring a reaction from the user, and adjusting any one of the aforementioned, to improve a sleep state of the user.

In an example, the method detecting, using a plurality of sensing devices configured within a vicinity of the human user, a plurality of signals associated with an event, associating with a sleep stage of the human user at a predetermined time. In an example, the method includes receiving the plurality of signals into an input device,. In an example, the input device is coupled to an engine device, which can include artificial intelligence techniques. The method includes processing, using the engine, by parsing information associated with the plurality of signals; and determining using the engine, a classification associated with the event; and storing the classification associated with the event at the predetermined time. The method then includes continuing the steps of detecting, receiving, processing, and storing for a plurality of other predetermined times from a first time to a second time to create a history of sleep data for the human user. In an example, the first time corresponds to a beginning of a first process and the second time corresponds to an ending of a second process. In an example, the method incudes processing, using an engage engine, the historical data to identify a task to be outputted to the human user, the task being one of a plurality of tasks stored in memory of a computing device and generating, using a logic therapy block, an output based upon the task.

In an example, the task is associated with a content, the content being configured to transmit to the human user by one of a plurality of transmission events selected from a text message, a voice message, a light notification, or a mechanical vibration.

In an example, the method further comprising inputting data from the human user into the memory of the computing device, the data associated with a total sleep time, a time to fall asleep, a wake up time, and a wake episodes between the first time and the second time; and transferring the data into the engine to update the history of the sleep data.

In an example, the plurality of sensing devices include an rf sensor, a light sensor, one or more microphones, a mechanical motion sensor, a temperature sensor, a humidity sensor, an image sensor, a pressure sensor, a depth sensor, or an optical sensor.

In an example, the engine includes various features. As an example, the engine comprises a pre-trained model composed of a plurality of statistical signatures. Each of the plurality of statistical signatures is associated with a different sleep stage. In an example, each of the plurality of statistical signatures is associated with a selected group of sensors and is associated with the classification. In an example, the engine also includes a detector module configured to receive an incoming stream of information from the plurality of signals from the select group of sensors and configured to perform a statistical inference based upon a plurality of current observed signals and the pre-trained model, the pre-trained model being provided for the history of the sleep.

In an example, the engage engine has various features. As an example, the engage engine comprises a plurality of pre-trained therapies configured from a user age, sex, BMI, and one or more sleep quality metrics. Each of the pre-trained therapies is configured to provide the task to the human user and configured to be adjusted in a frequency and an intensity based upon the feedback and one or more objective sleep metrics being monitored. In an example, the engage engine is configured to perform statistical inference to adjust the task by correlating the sleep metrics with the feedback.

In an example, the method comprises performing steps of continuing for third time to a fourth time, and performing the steps of continuing for an Nth time to an Mth time to form a plurality of historical data corresponding to a four week period. In an example, the output comprises a digital cognitive behavioral therapy output. In an example, the output can be selected from an audio message transmitted to the human user, a mechanical vibration to the human user, a light emitted on the human user, on-screen instructions for the user, or changing an environmental setting like light or temperature, among others.

In an example, the output comprises an audio conversation between the engine and the human user in an interactive manner. In an example, the output is provided interactively with the human user or at a designated time. In an example, the output is automatically generated using the logic therapy block.

In an example, the plurality of signals comprise a motion signal, a vital organ signal, a heart rate, a breathing rate, a spatial location of the human user, or a spatial configuration of the human user.

In other examples, the method includes initiating a wind down routine for the human user based upon processing the historical data using the engage engine. In an example ,the historical data includes at least information on a heart rate and a breathing rate. In an example, the output comprising information regarding a sleep window for the human user. In an example, the output comprising information related to a stimulus control for the human user. In an example, the output is related to an emotional state of the human user. These and other features include variations, modifications, and alternatives.

In an example, the present techniques provide one or more benefits, and/or advantages. In an example, the present techniques achieve behavioral changes through an interventions-sensing feedback framework using a combination of sensing techniques, artificial intelligence techniques, and active feedback mechanisms. In an example, the present techniques can be achieved using conventional hardware, software, and systems. These and other benefits are described throughout the present specification and more particularly below.

Definition of Sleep Terms:

In an example, to understand the present techniques, we have provided the following terms, although there can be variations, modifications, and alternatives.

Cognitive Behavioral Therapy (CBT) is a therapy designed to improve mental health using "action-oriented" external stimulation or interventions. CBT has been effective in treating depression, anxiety, insomnia, obesity and many other related mental conditions.

Cognitive Behavioral Therapy for Insomnia (CBTI) is a particular therapy of CBT that is focused on treating sleep habits and behaviors to improve sleep, ease falling asleep and staying asleep.

CBTI therapy process is often guided by a therapist that uses initially a screening questionnaire of the subject, then followed by a guidance of a specific set of tasks the subject is to be performing on their own, mostly around habit forming to achieve better sleep. Follow-up therapy meetings with the therapist occur on following occurrences where the therapy can be adjusted according to the input given by the subject on their ability to execute and the impact of the tasks they conducted on their sleep outcome.

Sleep sensing is a process of using sensors on a sleep subject to classify their sleep into stages, such as: Wake, Deep sleep, Light Sleep, REM (Rapid Eye Movement). In an example, the classification can be done manually by an experienced sleep technician or automatically using a machine computerized model trained for this task using artificial intelligence according to an example of the present invention. Additional statistics that are based on such a sleep analysis can provide the whole night metrics. For example Total sleep time (TST), Wake after sleep onset (WASO), Sleep efficiency (SE), Sleep onset latency (SOL), and others.

Deep Engage is a novel concept of sleep improvement technique such as CBTI, that is using sensing of the sleep subject to improve the success of the sleep therapy outcome. The concept is comprised of the following functional blocks, although there may be modifications, variations, and alternatives.

Sleep sensing/staging block: The sleep sensing/staging block provides an automated sleep stages analysis and generates the whole night statistics. It also improves over time by using feedback from the user surveying block that helps personalize the model of the sleep to represent that user sleep better in future nights. It also performs a post-night processing to tweak the sleep sensing model to be more sensitive/less sensitive for missed episodes of wake during the night.

CBTI block: The CBTI block provides the interface to the user, where suggested tasks are offered to the user. This can be fully automated using machine generated content (through text, voice messages or light notifications such as LEDs blinking pattern) or partially-automated using information and insights provided to a therapist.

User surveying block: The user surveying block makes requests by asking the user on their last night experience and ask their estimation to sleep parameters, such as total sleep time, time to fall asleep, wake up time, wake episodes during the night etc. This feedback from the user is being fed to the Sleep sensing block for re-calibration and tweaking of the model to provide a better personalized sleep model. The innovation here is the ability to automate this data collection by text message, using app notification, over conversational chatbot or other means.

Logic therapy block: The logic therapy block is where the offered tasks are being selected based on analysis of previous analyzed nights of that subject, latest sleep related activities, success or impact of previous tried therapy suggestions etc. The outcome of this block is a guided plan of CBTI tasks interaction to be run in the next nights with adjusted selection, intensity, different triggering activation (specific times or following specific events detected by the system). The technique conducts a long engagement with the user that learns and adapt to the user patterns, habits around sleep over time. By measuring the therapy outcomes a personalized therapy can be adjusted to be more impactful over time.

Sensing of the sleep of a subject and the sleep environment is conducted by a multitude of sensors, including, but not limited to, a wireless sensor, light level sensor, motion sensors, acoustic sensors, microphones in an example. In an example, sensing can occur using any of the sensing techniques described herein or outside of the present specification. Further details of the present techniques can be described below in refence to the following Figures.

Figure 28:
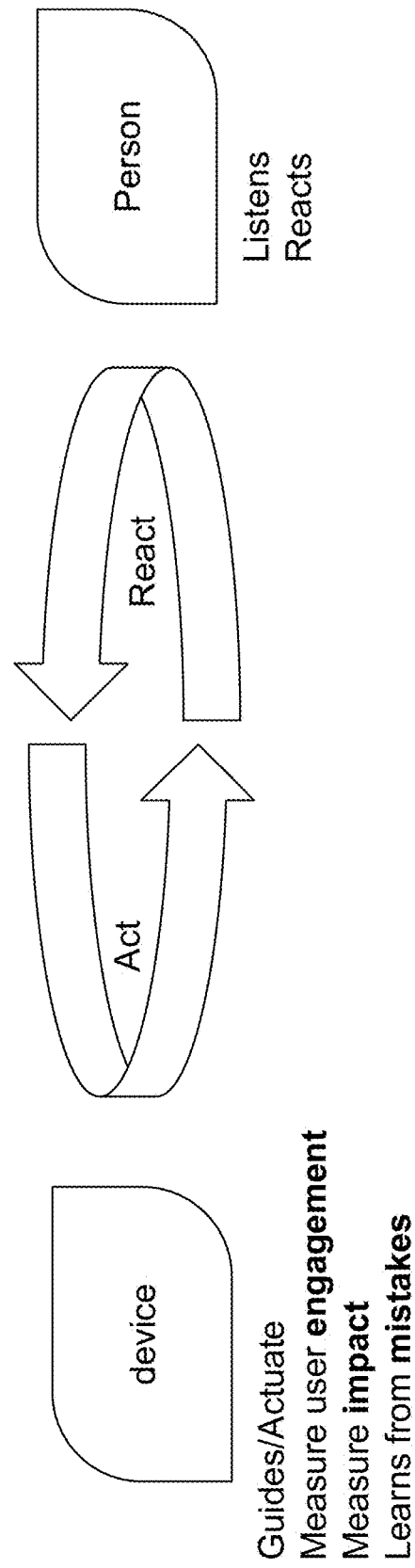
FIG. 28 is a simplified diagram of a process to deep engage with a human user sensing signals associated with sleep and active feedback according to an example of the present invention.

FIG. 28 is a simplified diagram of a process to deep engage with a human user sensing signals associated with sleep and active feedback according to an example of the present invention. As shown, the process includes devices, which can be used to guide/actuate, measure user engagement, measure impact, and includes information for learning. The method incudes an engine to process information for creating historical information, and signatures of a plurality of sleep related states (whether the user is sleeping or not sleeping), and provides a task or reaction to a person. In an example, the process uses active feedback to adjust the actions and reactions to help optimize the sleep process.

Figure 29:
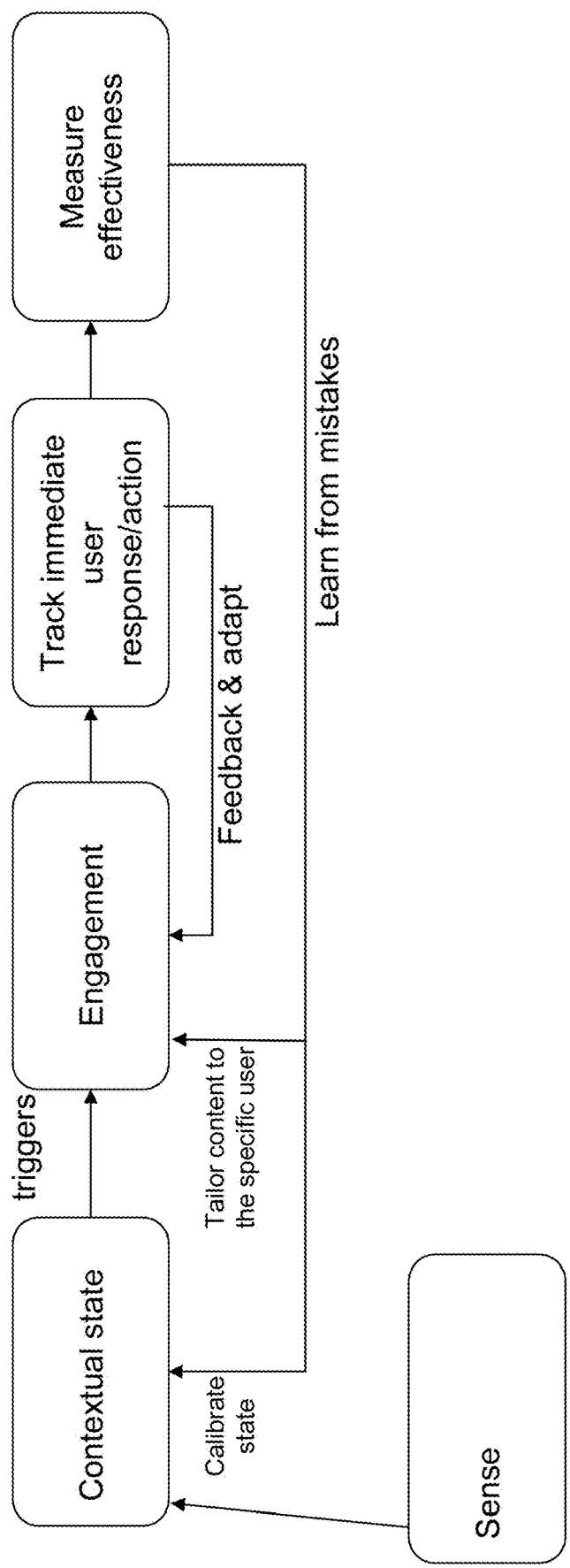
FIG. 29 is a more detailed diagram of the process to deep engage according to an example of the present invention.

FIG. 29 is a more detailed diagram of the process to deep engage according to an example of the present invention. As shown, the process includes, among others, a sense block, a contextual state block, an engagement block, a user response block, a measurement block, and feedback loops including "Learn from mistakes," "Feedback & adapt", and "Calibrate state", and "tailor content to the specific user.

In an example, the sense block includes hardware and software to detect (intensity and frequency) and spatial characteristics based upon time or other frequency a variety of activities including ambient light level, temperature, and other information. In an example, the sense block also keeps track of the time of day, day in the week, calendar, weather, or other external information. In an example, the sense block includes a contextual tracker, bounding box tracker, and vital signs, tracker, among others.

In an example, the process includes a process for learning, including a contextual state via the contextual tracker. The learning process maintains historical patterns from sensed information. The historical patterns can be spatial "Microlocation". The patterns can also include schedule, sleep/stress, and action. The learning process also includes an engagement process and related block. Further details of the learning process are described below.

As shown, contextual state is determined using an engine that processes the sensed information. In an example, the contextual state can include "Trying to fall asleep," "Asleep", among other. Other contextual states include trying to get up from bed, abnormal, taking a shower, getting dressed, among others.

In an example, the process includes an engagement block. The block provides for an output to the user. The output can include an automated night light, personal insights, a positive presence signa, an alert, guided breathing or other activities, and guided start of day exercise routine, each of which can be output via audio and/or audio video. Of course, there can be other variations, modifications, and alternatives.

Figure 30:
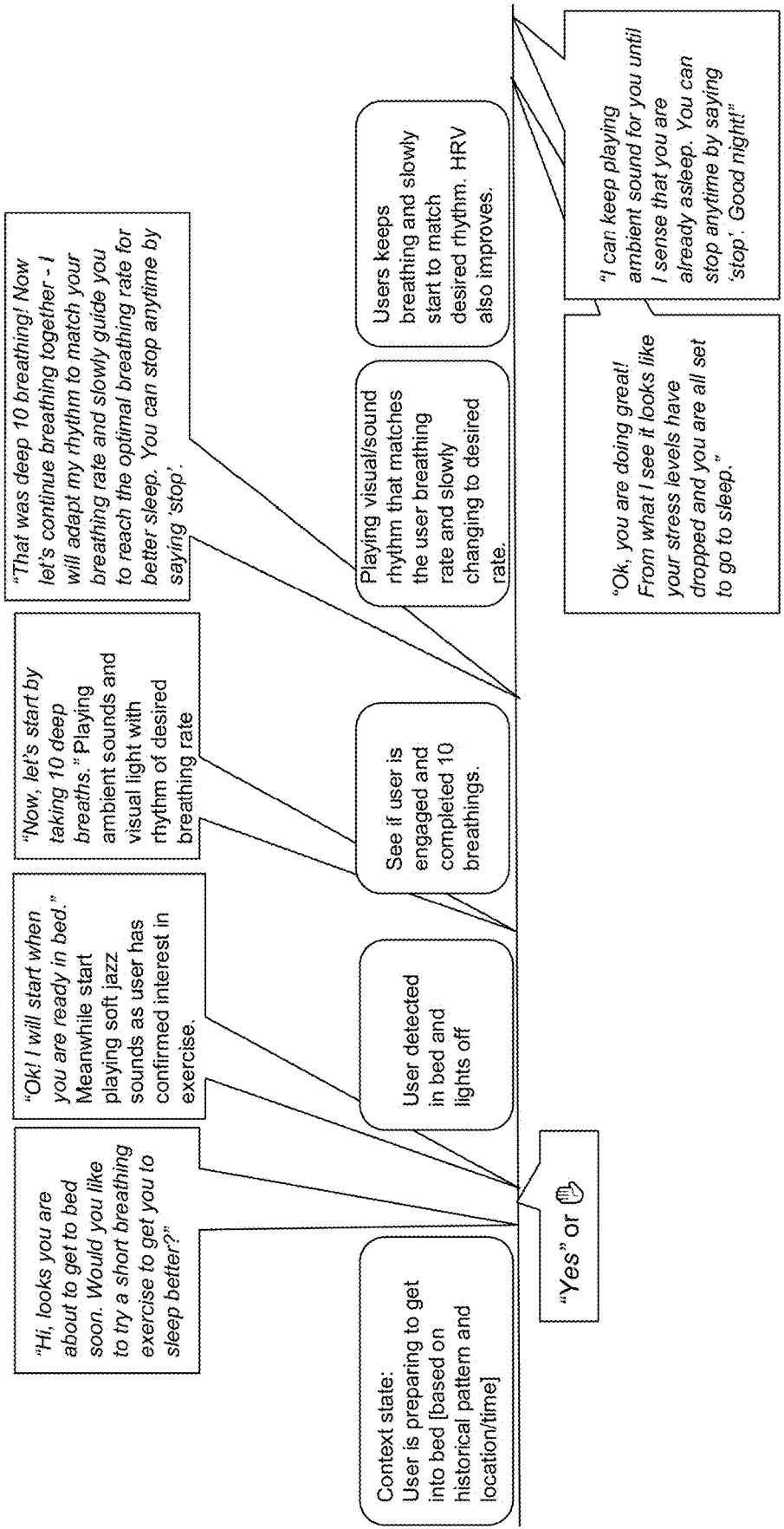
FIG. 30 is a simplified diagram illustrating breathing exercises as feedback for the process to deep engage according to an example of the present invention.

FIG. 30 is a simplified diagram illustrating breathing exercises as feedback for the process to deep engage according to an example of the present invention. As shown is a horizontal line representing a time line from an earlier time, which is on the left, to a later time, which is on the right. In an example, the method includes sensing a targeted region using a plurality of sensors, processing information from the sensors, and determining the "Context state" as shown. Once the context state is determined, the method includes processing with an engage to output audio information such as "Hi, looks you are about to get to bed . . . ". The output is designed to provide feedback to the user, based upon historical information, to help the user have improved sleep.

Figure 31:
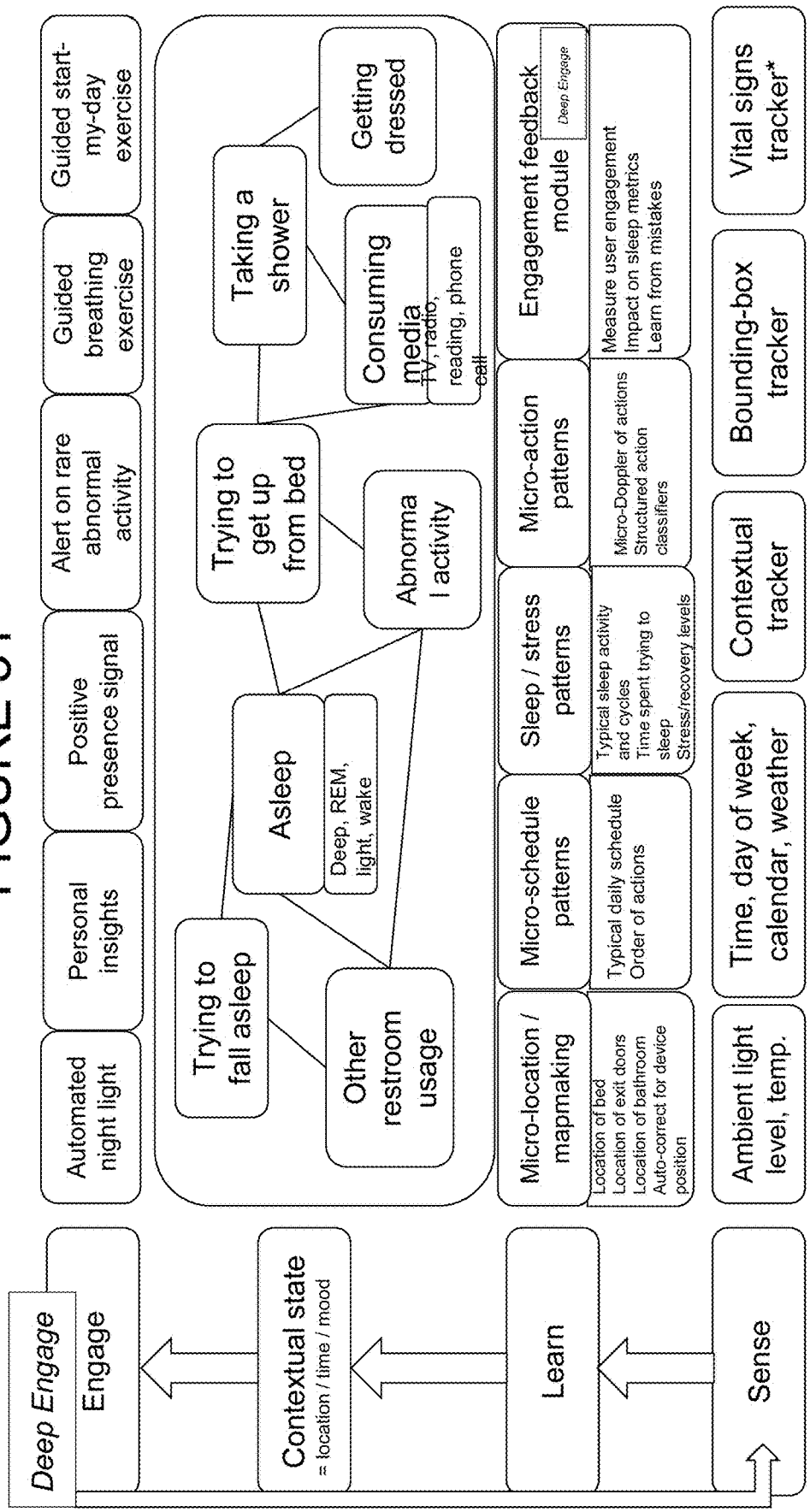
FIG. 31 is a simplified diagram illustrating details of the process to deep engage according to an example of the present invention.

FIG. 31 is a simplified diagram illustrating details of the process to deep engage according to an example of the present invention. As shown, the present process includes stages for sensing, learning, determining a contextual state, and engaging with the user. Further details of such process are shown by way of an example below.

Figure 32:
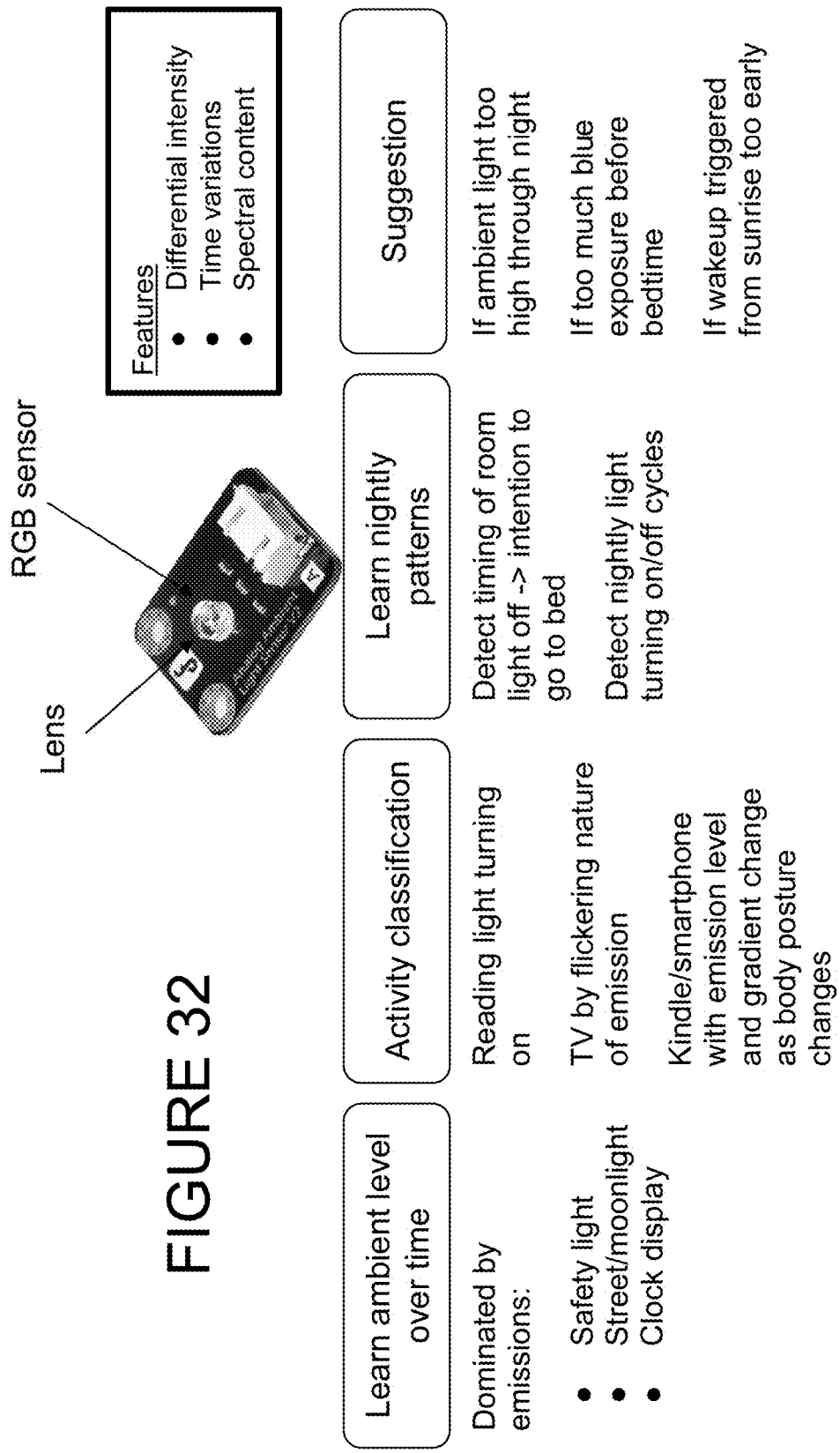
FIG. 32 is a detailed diagram illustrating a process to deep engage using ambient lighting according to an example of the present invention.

FIG. 32 is a detailed diagram illustrating a process to deep engage using ambient lighting according to an example of the present invention. In an example, the present process includes techniques for learning ambient levels over time, activity classification, learning nightly patterns, and providing outputs or suggestions. Further details of such process are shown by way of an example below.

EXAMPLES

To prove the principles and operation of the present techniques, we provided examples of implementing the present techniques in hardware and software. Such examples are merely illustrative, and one of ordinary skill in the art would recognize other variations, modifications, and alternatives.

How the present technique detects bed presence?

During the initial installation of the device inside a user bedroom, the device RF sensor records a signature of the radar signal when a person is inside the bed. Similarly, the device records a signature of the radar signal when a person is in the bedroom outside of the bed. After this initial training, the device from that point onwards will keep comparing in real-time the current observed signature of the radar signal and compare it against the pre-recorded signatures of the "in-bed" and "out-of-bed" scenarios. The device then uses statistical methods to compare the signatures' resemblance and determines what is the most likely scenario observed in the bedroom—"in-bed" or "out-of-bed". This information about the user gives, in real-time, the ability to monitor if the user is entering the bed, or leaving the bed, and create interventions that are based on this user's state/scenario.

How the present technique tracks sleep stages?

The present technique has accumulated many recorded and monitored nights of sleep of many people using an RF sensor. The recorded nights were recorded alongside third-party sleep monitoring devices that provided estimated stages of sleep (e.g. "REM", "deep sleep", "light sleep", "wake state"). Using a statistical model that learns from the third-party devices labeling of the sleep stages, a new statistical model was generated that creates the necessary correlation between the observed signal from the RF sensor and the sleep stages labels. Such correlation is used to generate for each sleep stage the reciprocal set of signal signatures associated with that sleep stage. For example, REM stage is distinct from other sleep stages due to rapid body movement, elevated heart rate and elevated breathing. These patterns are all generating small amounts of vibrations, an RF signature, that are captured with the RF sensor and observed by the device. The trained model is then used to generate in real-time the sleep stage estimates of newly recorded night using the RF sensor in real-time.

In an example, the present technique uses a model that is performing a correlation between the pre-recorded signatures of the sleep stages and compares it against the pre-trained signatures of the sleep stages. The device then uses statistical methods to compare the signatures' resemblance and determines what is the most likely sleep stage observed currently. This information about the user gives, in real-time, the ability to monitor if the user is awake or asleep, and creates interventions that are based on this user's sleep state—e.g., sounds, lights or text/recorded messages.

In an example, the present technique provides for in-time stimulus, triggered by sensing of the bed room and location and activities of the user at precise time periods. In an example, the technique provides for an ability to measure the particular stimulus (including intensity, choice) effect on that user and given the particular circumstances (environmental conditions, history of users)—quantify the impact for the combo of stimulus-environment-user state. In an example, the present technique provides for an ability to learn and adapt the stimulus based on previous interactions with that user.

In an example, the present method and system can also provide for a predictive model to allow for the following:

Emotion Prediction:

The ability to predict user's emotional state (anxiety, valence) and use it to provide personalized cognitive therapy. Emotional state is estimated based on a few signals. The research literature has indicated a strong correlation between emotional stress and the heart rate, heart rate variability and sleep movement. All of these signals are being monitored using the RF sensor, and allow to create an indication when they become elevated and could indicate a stress level.

Intention Prediction:

The ability to predict a user's action before it actually happens. This is done by first training a machine learning model with the RF signal that leads to a particular user action of interest. The model focuses on the preceding user observed signal and creates an estimator to give an estimate of this action to happen soon. For example, the user leaving the bed during the night is an action of interest. During the minutes prior to that, the user is exhibiting movement restlessness, changes in vital signs and sleep stages. The device then estimates the user's intention to leave bed soon, before it happens.

Personalized Sleep Tracking:

The sleep tracking is estimating sleep stages of the user based on a pre-trained machine learning model. The model is generic and applies to the user profile (based on age, sex, BMI etc.). Personalization of the sleep tracking is happening when the sleep stages estimates are also based on historical monitored sleep from previous nights of a particular user. The information contained in previously monitored night of a user gives the ability to self-correct and adjust to model to better reflect an individual unique sleep pattern. For example, the generic sleep stages model estimates someone being asleep in the beginning of the night, while understaging from a user feedback that that was a wrong estimation. The model takes the feedback and adjust the model to be prepared better for the next observed night, for being more sensitive to wake state associated signal to be more likely to detect the wake phase at the beginning of the night.

Personalized Therapy:

Therapy can be automated or partially automated. The automated part of the therapy is considering the user scenario and analysis of previous nights' sleep. However, once a therapy is offered, a user feedback should measure the success of the suggested therapy. The personalization of the therapy is done by adjusting the therapy to the individual personal impact of previous suggested therapy steps and intensity, and mainly focusing on what is providing the impact for that user. For example, a user is given an instruction to change the time they go to bed by 2 hours. If after a week no improvement is registered by monitoring the sleep quality metrics, an alternative therapy method can be suggested, or increase of the time from 2 to 4 or 5 hours can be suggested.

Detecting Menopause Hot Flashes:

Hot flashes appear along others rapid changes in user hear and breathing signal. Using the signals coming from the rf sensor, the device is monitoring appearance of such rapid changes and indicate a detection of the hot flashes episodes.

Having described various embodiments, examples, and implementations, it should be apparent to those skilled in the relevant art that the foregoing is illustrative only and not limiting, having been presented by way of example only. Many other schemes for distributing functions among the various functional elements of the illustrated embodiment or example are possible. The functions of any element may be carried out in various ways in alternative embodiments or examples.

Also, the functions of several elements may, in alternative embodiments or examples, be carried out by fewer, or a single, element. Similarly, in some embodiments, any functional element may perform fewer, or different, operations than those described with respect to the illustrated embodiment or example. Also, functional elements shown as distinct for purposes of illustration may be incorporated within other functional elements in a particular implementation. Also, the sequencing of functions or portions of functions generally may be altered. Certain functional elements, files, data structures, and so one may be described in the illustrated embodiments as located in system memory of a particular or hub. In other embodiments, however, they may be located on, or distributed across, systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures of files may be used and various described data structures of files may be combined or otherwise arranged.

In other examples, combinations or sub-combinations of the above disclosed invention can be advantageously made. The block diagrams of the architecture and flow charts are grouped for ease of understanding. However, it should be understood that combinations of blocks, additions of new blocks, re-arrangement of blocks, and the like are contemplated in alternative embodiments of the present invention.

The specification and drawings are, accordingly, to be regarded in an illustrative rather than a restrictive sense. It will, however, be evident that various modifications and changes may be made thereunto without departing from the broader spirit and scope of the invention as set forth in the claims.

The invention claimed is:

1. A method for processing signals from a human user in connection with a sleep state, the method comprising:
    detecting, using a plurality of sensing devices configured within a vicinity of the human user, a plurality of signals associated with an event associated with a sleep stage of the human user at a predetermined time;
    receiving the plurality of signals into an input device, the input device being coupled to an engine device;
    processing, using the engine device, by parsing information associated with the plurality of signals; and determining using the engine device, a classification associated with the event;
    storing the classification associated with the event at the predetermined time;
    continuing the steps of detecting, receiving, processing, and storing for a plurality of other predetermined times from a first time to a second time to create a history of sleep data for the human user, the first time corresponding to a beginning of a first process and the second time corresponding to an ending of a second process;
    processing, using an engage engine, the historical sleep data to identify a task to be outputted to the human user, the task being one of a plurality of tasks stored in memory of a computing device;
    generating, using a logic therapy block, an output based upon the task; and
    initiating a wind down routine for the human user based upon processing the historical sleep data using the engage engine, the historical sleep data including at least information on a heart rate and a breathing rate.

2. The method of claim 1 wherein the task is associated with a content, the content being configured to transmit to the human user by one of a plurality of transmission events selected from a text message, a voice message, a light notification, or a mechanical vibration.

3. The method of claim 1 further comprising inputting data from the human user into the memory of the computing device, the data associated with a total sleep time, a time to fall asleep, a wake up time, and a wake episodes between the first time and the second time; and transferring the data into the engine to update the history of the sleep data.

4. The method of claim 1 wherein the plurality of sensing devices includes an rf sensor, a light sensor, one or more microphones, a mechanical motion sensor, a temperature sensor, a humidity sensor, an image sensor, a pressure sensor, a depth sensor, or an optical sensor.

5. The method of claim 1 wherein the engine device comprises a pre-trained model composed of a plurality of statistical signatures, each of the plurality of statistical signatures being associated with a different sleep stage, each of the plurality of statistical signatures associated with a selected group of sensors and associated with the classification, and a detector configured to receive an incoming stream of information from the plurality of signals from the select group of sensors and configured to perform a statistical inference based upon a plurality of current observed signals and the pre-trained model, the pre-trained model being provided for the history of the sleep.

6. The method of claim 1 wherein the engage engine comprises a plurality of pre-trained therapies configured from a user age, sex, BMI, and one or more sleep quality metrics, the pre-trained therapies configured to provide the task to the human user and configured to be adjusted in a frequency and an intensity based upon the feedback and one or more objective sleep metrics being monitored.

7. The method of claim 6 wherein the engage engine is configured to perform statistical inference to adjust the task by correlating the sleep metrics with the feedback.

8. The method of claim 1 wherein the logic therapy block is configured to determine the task based upon the historical data.

9. The method of claim 1 wherein the plurality of sensing devices comprises one or more rf sensors.

10. The method of claim 1 further comprising performing steps of continuing for third time to a fourth time, and performing the steps of continuing for an Nth time to an Mth time to form a plurality of historical data corresponding to a four week period.

11. The method of claim 1 wherein the output is selected from initiation of an automated night light, an output with personal insight, a positive presence signal, an alert, a guided breathing exercise, or a guided start of day exercise.

12. The method of claim 1 wherein the output comprises a digital cognitive behavioral therapy output, the output selected from an audio message transmitted to the human user, a mechanical vibration to the human user, a light emitted on the human user, on-screen instructions for the user, or changing an environmental setting like light or temperature.

13. The method of claim 1 wherein the output comprises an audio conversation between the engine and the human user.

14. The method of claim 1 wherein the output is provided interactively with the human user at a designated time.

15. The method of claim 11 wherein the output is automatically generated using the logic therapy block.

16. The method of claim 1 wherein the plurality of sensing devices comprises at least one rf sensor and an audio sensor.

17. The method of claim 1 wherein the plurality of signals comprise a motion signal, a vital organ signal, a heart rate, a breathing rate, a spatial location of the human user, or a spatial configuration of the human user.

18. The method of claim 1 wherein the output comprises information regarding a sleep window for the human user.

19. The method of claim 1 wherein the output comprises information related to a stimulus control for the human user.

20. The method of claim 1 wherein the output is related to an emotional state of the human user.

21. The method of claim 1 wherein the plurality of sensing devices comprises an rf sensor, an image capturing device, a microphone, a motion sensor, a temperature sensor, a humidity sensor, an image sensor, a pressure sensor, a depth sensor, or an optical sensor.

22. A method for processing signals from a human user in connection with a sleep state and using information from the signals for digital cognitive behavioral therapy, the method comprising:
   detecting, using a plurality of sensing devices configured within a vicinity of the human user, a plurality of signals associated with an event associated with a sleep stage of the human user at a predetermined time;
   receiving the plurality of signals into an input device, the input device being coupled to an engine device;
   processing, using the engine device, by parsing information associated with the plurality of signals;
   determining using the engine device, a classification associated with the event;
   storing the classification associated with the event at the predetermined time;
   continuing the steps of detecting, receiving, processing, and storing for a plurality of other predetermined times from a first time to a second time to create a history of sleep data for the human user, the first time corresponding to a beginning of a first process and the second time corresponding to an ending of a second process;
   capturing using one or more of the plurality of sensing devices a plurality of current signals associated with a current event at a current time;
   processing the plurality of current signals using an engage engine and the historical sleep data to identify a current task to be outputted to the human user, and generating, using a logic therapy block, an output based upon the task; and
   initiating a wind down routine for the human user based upon processing the historical sleep data using the engage engine, the historical sleep data including at least information on a heart rate and a breathing rate.

23. The method of claim 22 wherein the task is associated with a content, the content being configured to transmit to the human user by one of a plurality of transmission events selected from a text message, a voice message, a light notification, or a mechanical vibration.

24. The method of claim 22 further comprising inputting data from the human user into a memory of a computing device, the data associated with a total sleep time, a time to fall asleep, a wake up time, and a wake episodes between the first time and the second time; and transferring the data into the engine device to update the history of the sleep data.

25. The method of claim 22 wherein the plurality of sensing devices includes an rf sensor, a light sensor, a microphone, a mechanical motion sensor, a temperature sensor, and a humidity sensor.

26. The method of claim 22 wherein the engine device comprises a pre-trained model composed of a plurality of statistical signatures, each of the plurality of statistical signatures being associated with a different sleep stage, each of the plurality of statistical signatures associated with a selected group of sensors and associated with the classification, and a detector configured to receive an incoming stream of information from the plurality of signals from the select group of sensors and configured to perform a statistical inference based upon a plurality of current observed signals and the pre-trained model, the pre-trained model being provided for the history of the sleep.

27. The method of claim 22 wherein the engage engine comprises a plurality of pre-trained therapies configured from a user age, sex, BMI, and one or more sleep quality metrics, the pre-trained therapies configured to provide the task to the human user and configured to be adjusted in a frequency and an intensity based upon the feedback and one or more objective sleep metrics being monitored.

28. The method of claim 24 wherein the engage engine is configured to perform statistical inference to adjust the task by correlating the sleep metrics with the feedback.

29. The method of claim 22 wherein the logic therapy block is configured to determine the task based upon the historical data.

30. The method of claim 22 wherein the plurality of sensing devices comprises one or more rf sensors.

31. The method of claim 22 further comprising performing steps of continuing for third time to a fourth time, and performing the steps of continuing for an Nth time to an Mth time to form a plurality of historical data corresponding to a four week period.

32. The method of claim 22 wherein the output is selected from initiation of an automated night light, an output with personal insight, a positive presence signal, an alert, a guided breathing exercise, or a guided start of day exercise.

33. The method of claim 22 wherein the output comprises a digital cognitive behavioral therapy output, the output selected from an audio message transmitted to the human user, a mechanical vibration to the human user, a light emitted on the human user, on-screen instructions for the user, or changing an environmental setting like light or temperature.

34. The method of claim 22 wherein the output is automatically generated using the logic therapy block.

35. The method of claim 22 wherein the plurality of sensing devices comprises at least one rf sensor and an audio sensor.

36. The method of claim 22 wherein the plurality of signals comprise a motion signal, a vital organ signal, a heart rate, a breathing rate, a spatial location of the human user, or a spatial configuration of the human user.

37. The method of claim 22 wherein the output comprises information regarding a sleep window for the human user.

38. The method of claim 22 wherein the output comprises information related to a stimulus control for the human user.

39. The method of claim 22 wherein the output is related to an emotional state of the human user.

* * * * *